(12) United States Patent
Bennani et al.

(10) Patent No.: US 7,423,056 B2
(45) Date of Patent: Sep. 9, 2008

(54) TRICYCLIC HETEROARYL PIPERAZINES, PYRROLIDINES AND AZETIDINES AS SEROTONIN RECEPTOR MODULATORS

(75) Inventors: Youssef L. Bennani, Shaker Heights, OH (US); David C. Bom, Broadview Heights, OH (US); Michael J. Robarge, Burton, OH (US)

(73) Assignee: Athersys, Inc., Cleveland, OH (US)

( * ) Notice: Subject to any disclaimer, the term of this patent is extended or adjusted under 35 U.S.C. 154(b) by 549 days.

(21) Appl. No.: 11/217,991

(22) Filed: Sep. 1, 2005

(65) Prior Publication Data

US 2006/0079567 A1 Apr. 13, 2006

Related U.S. Application Data

(60) Provisional application No. 60/607,142, filed on Sep. 3, 2004.

(51) Int. Cl.
*A61K 31/40* (2006.01)
*C07D 209/56* (2006.01)
*C07D 495/02* (2006.01)

(52) U.S. Cl. .................. 514/411; 548/416; 548/427; 548/429; 548/430; 514/410

(58) Field of Classification Search .......... 514/410, 514/411; 548/416, 427, 429, 430
See application file for complete search history.

(56) References Cited

FOREIGN PATENT DOCUMENTS

WO  WO 9965911 A1  12/1999
WO  WO 2003 051883 A1  6/2003

OTHER PUBLICATIONS

Von Siavosh Mahboobi et al. "Synthesis of Carbazole Derivatives 1. Reaction of 3- 2(-Nitroethenyl) indole-2-malonic Acid Esters With Michael-Acceptors" Archiv der Pharmazie, Weinheim, Germany 1995 vol. 328(1) pp. 29-38.

Siavosh Mahboobi et al. "Carbazole DerivativeS With Antimycobacterial Activity" Archiv der Pharmazie, Weinheim, Germany 1994 vol. 327(10) pp. 611-617.
Atul Agarwal et al. "Three-Dimensional Quantitative Structure-Activity Relationships Of 5-HT Receptor Binding Data For Tetrahydropyridinylindole Derivatives: A Comparison Of The Hansch And CoMFA Methods" Journal of Medicinal Chemistry, Athen, Georgia, USA 1993, vol. 36(25) pp. 4006-4014.
M Herslof et al. "Synthesis Of A New Conformationally Defined Serotonin Homolog By Intramolecular [4+2] Cycloaddition" Tetrahedron Letter Tucson, Arizona 1987, pp. 3423-3426.
Sydney Archer et al "Synthesis And Biological Properties Of Some 6H-pyrido [4, 3-b] carbazoles" Journal of Medicinal Chemistry Troy, NY 1987, vol. 30(7) pp. 1204-1210.
Silvio J Martinez et al. "Cyclic Allylamine/Enamine Systems—6. Some Reactions of 4- (indol-3-ylcarbonyl) and 4-indole-3-ylmethyl) -1, 2, 5, 6-tetrahydro-1-methylpyridines" Tetrahedron Letters Manchester, UK 1984, vol. 40(17) pp. 3339-3343.
David L Coffen et al. "Syntheses Of An Antipsychotic Pyrrolo [2,3-g]isoquinoline From Areca Alkaloids" Journal of Organic Chemistry Nutley, NJ 1984, vol. 49(26) pp. 5109-5113.
Gary L Olson "Dopamine Receptor Model And Its Application In The Design Of A New Class Of Rigid Pyrrolo [2,3-g]isoquinoline Antipsychotics" Journal of Medicinal Chemistry Nutley, NJ 1981, vol. 24(9) pp. 1026-1034.
Lionel Chevolot et al. "Studies In The Indole Series. XII. Synthesis Of Indole Alkaloids And Structural Analogs Via 5, 6-dihydropyridinium Salts" Bulletin de la Societe Chimique de France Gif-suf-Yvette, France 1976, pp. 1222-1226.
L G Rashidyan et al "Isoindoline Derivatives. I. Synthesis Of Some Diamines Of The Isoindoline Series" Armyanskii Khimicheskii Zhurnal Erevan, USSR 1968, vol. 21(9) pp. 793-807.

*Primary Examiner*—Golam M Shameem
(74) *Attorney, Agent, or Firm*—Wood Phillips et al.

(57) ABSTRACT

The present invention generally relates to a series of compounds, to pharmaceutical compositions containing the compounds, and to use of the compounds and compositions as therapeutic agents. More specifically, compounds of the present invention are hexahydroazepinoindole and octahydroazepinoindole compounds. These compounds are serotonin receptor (5-HT) ligands and are useful for treating diseases, disorders, and conditions wherein modulation of the activity of serotonin receptors (5-HT) is desired (e.g. anxiety, depression and obesity).

4 Claims, No Drawings

TRICYCLIC HETEROARYL PIPERAZINES, PYRROLIDINES AND AZETIDINES AS SEROTONIN RECEPTOR MODULATORS

CROSS-REFERENCE TO RELATED APPLICATIONS

This application claims the priority of Provisional Application No. 60/607,142, filed Sep. 3, 2004.

FIELD OF THE INVENTION

The present invention generally relates to a series of compounds, to pharmaceutical compositions containing the compounds, and to use of the compounds and compositions as therapeutic agents. More specifically, compounds of the present invention are tricyclic heteroaryl piperazine, pyrrolidine and azetidine compounds. These compounds are serotonin receptor (5-HT) ligands and are useful for treating diseases, disorders, and conditions wherein modulation of the activity of serotonin receptors (5-HT) is desired (e.g. addiction, anxiety, depression and obesity).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory, and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting.

The major classes of serotonin receptors ($5\text{-}HT_{1\text{-}7}$) contain one to seven separate receptors that have been formally classified. See Glennon, et al., *Neuroscience and Behavioral Reviews*, 1990, 14, 35; and D. Hoyer, et al. *Phannacol. Rev.* 1994, 46,157-203.

For example, the $5\text{-}HT_2$ family of receptors contains $5\text{-}HT_{2a}$, $5\text{-}HT_{2b}$, and $5\text{-}HT_{2c}$ subtypes, which have been grouped together on the basis of primary structure, secondary messenger system, and operational profile. All three $5\text{-}HT_2$ subtypes are G-protein coupled, activate phospholipase C as a principal transduction mechanism, and contain a seven-transmembrane domain structure. There are distinct differences in the distribution of the three $5\text{-}HT_2$ subtypes in a mammal. The $5\text{-}HT_{2b}$ and $5\text{-}HT_{2a}$ receptors are widely distributed in the peripheral nervous system, with $5\text{-}HT_{2a}$ also found in the brain. The $5\text{-}HT_{2c}$ receptor has been found only in the central nervous system, being highly expressed in many regions of the human brain. See G. Baxter, et al. *Trends in Pharmacol. Sci.* 1995, 16, 105-110.

Subtype $5\text{-}HT_{2a}$ has been associated with effects including vasoconstriction, platelet aggregation, and bronchoconstriction, as well as certain CNS effects, while subtype $5\text{-}HT_{2c}$ has been associated with diseases that include depression, anxiety, obsessive compulsive disorder, addiction, panic disorders, phobias, psychiatric syndromes, and obesity. Very little is known about the pharmocologic role of the $5\text{-}HT_{2b}$ receptor. See F. Jenck, et al., *Exp. Opin. Invest. Drugs*, 1998, 7, 1587-1599; M. Bos, et al., *J. Med. Chem.*, 1997, 40, 2762-2769; J. R. Martin, et al., *The Journal of Pharmacology and Experimental Therapeutics*, 1998, 286, 913-924; S. M. Bromidge, et al., 1. *Med. Chem.*, 1998, 41, 1598-1612; G. A. Kennett, *Drugs*, 1998, 1, 4, 456-470; and A. Dekeyne, et al., *Neuropharmacology*, 1999, 38, 415-423.

WO 93/13105 discloses thiophene derivatives; U.S. Pat. No. 4,414,225 discloses thiophene, furan and pyrrole derivatives and WO 96/12201 discloses furan derivatives.

SUMMARY OF THE INVENTION

The present invention is directed to compounds of the formula:

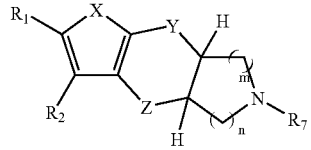

where
X is S or O;
m is 1 or 2;
n is 1 or 2;
m+n is $\geq 2$;
Y is $CR_3R_{3a}$ and Z is a covalent bond or $CR_4R_{4a}$,
Y is a covalent bond and Z is $CH_2CH_2$ or $CR_4R_{4a}$ or
Y or $CH_2CH_2$ and Z is a covalent bond;
$R_1$ and $R_2$ are independently selected from the group consisting of H, halogen, $C_{1\text{-}10}$ alkyl, $C_{2\text{-}10}$alkenyl, $C_{2\text{-}10}$alkynyl, perhaloalkyl, CN, $OR_5$, $SR_5$, $N(R_5)_2$, $COOR_5$, $COR_6$, $CON(R_5)_2$, $NR_5COR_6$, $NR_5CO_2R_6$, $NR_5SO_2R_6$, aryl, heteroaryl, $C_{1\text{-}10}$alkylaryl, and $C_{1\text{-}10}$alkylheteroaryl, wherein said aryl or heteroaryl can be optionally substituted;
$R_1$ and $R_2$ taken together can form a 5- or 6-member aryl or heteroaryl ring that is optionally substituted;
$R_3$ is selected from the group consisting of H, halogen, $C_{1\text{-}10}$alkyl, $C_{2\text{-}10}$alkenyl, $C_{2\text{-}10}$ alkynyl, perhaloalkyl, CN, $OR_5$, $SR_5$, $N(R_5)_2$, $OCOR_6$, $COOR_5$, $COR_6$, $CON(R_5)_2$, $NR_5COR_6$, $NR_5CO_2R_6$, $NR_5SO_2R_6$, aryl, heteroaryl, $C_{1\text{-}10}$alkylaryl, and $C_{1\text{-}10}$ alkylheteroaryl, wherein said aryl or heteroaryl can be optionally substituted;
$R_{3a}$ is H or $R_3$ and $R_{3a}$ taken together are —$CH_2CH_2$— or carbonyl;
$R_4$ is selected from the group consisting of H, halogen, $C_{1\text{-}10}$alkyl, $C_{2\text{-}10}$alkenyl, $C_{2\text{-}10}$ alkynyl, perhaloalkyl, CN, $OR_5$, $SR_5$, $N(R_5)_2$, $OCOR_6$, $COOR_5$, $COR_6$, $CON(R_5)_2$, $NR_5COR_6$, $NR_5CO_2R_6$, $NR_5SO_2R_6$, aryl, heteroaryl, $C_{1\text{-}10}$alkylaryl, and $C_{1\text{-}10}$ alkylheteroaryl, wherein said aryl or heteroaryl can be optionally substituted;
$R_{4a}$ is H or $R_4$ and $R_{4a}$ taken together are —$CH_2CH_2$— or carbonyl;
$R_5$ is selected from the group consisting of H, $C_{1\text{-}10}$alkyl, $C_{2\text{-}10}$alkenyl, $C_{2\text{-}10}$alkynyl, perhaloalkyl, $C_{1\text{-}10}$alkyl-O—$C_{1\text{-}10}$alkyl, aryl, heteroaryl, $C_{1\text{-}10}$alkyl-O-aryl, $C_{1\text{-}10}$alkyl-O-heteroaryl, $C_{1\text{-}10}$alkylaryl, and $C_{1\text{-}10}$alkylheteroaryl, wherein said aryl or heteroaryl can be optionally substituted;

$R_6$ is selected from the group consisting of $C_{1-10}$alkyl, $C_{2-10}$alkenyl, $C_{2-10}$alkynyl, perhaloalkyl, $C_{1-10}$alkyl-O—$C_{1-10}$alkyl, aryl, heteroaryl, $C_{1-10}$alkyl-O-aryl, $C_{1-10}$alkyl-O-heteroaryl, $C_{1-10}$alkylaryl, and $C_{1-10}$alkylheteroaryl, wherein said aryl or heteroaryl can be optionally substituted, and $R_7$ is selected from the group consisting of H, $C_{1-10}$alkyl, $C_{2-10}$alkenyl, $C_{2-10}$alkynyl, $C_{1-10}$alkyl-O—$C_{1-10}$alkyl, $COOR_5$, $COR_6$, $CON(R_5)_2$, aryl, heteroaryl, $C_{1-10}$alkyl-O-aryl, $C_{1-10}$alkyl-O-heteroaryl, $C_{1-10}$alkylaryl, and $C_{1-10}$alkylheteroaryl, wherein said aryl or heteroaryl can be optionally substituted, and the pharmaceutically acceptable salts thereof.

Preferably, X is S; Y is a bond or $CR_3R_{3a}$; Z is $CR_4R_{4a}$ or a bond; $R_1$, and $R_2$ are halogen, $C_{1-10}$alkyl, O—$C_{1-10}$alkyl or $CF_3$; $R_3$ is $C_{1-10}$alkyl; $R_{3a}$ is H; $R_4$ is $C_{1-10}$ alkyl; $R_{4a}$ is H and $R_7$ is H.

Another embodiment of the present invention provides a pharmaceutical composition comprising a compound of Formula (I), or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-$HT_{2c}$ receptor is implicated and modulation of a 5-$HT_{2c}$ function is desired. The method comprises administering a therapeutically effective amount of a compound of Formula (I), or a pharmaceutically acceptable salt thereof, to the mammal.

Yet another embodiment of the present invention comprises a method of modulating 5-HT receptor function with an effective amount of compound of Formula (I), or a pharmaceutically acceptable salt thereof.

A further embodiment of the present invention provides a method of treating or preventing diseases, disorders, and/or conditions of the central nervous system. The method comprises administering a therapeutically effective amount of a compound of Formula (I), or a pharmaceutically acceptable salt thereof, to the mammal.

Specific diseases, disorders and/or conditions for which compounds of the Formula (I) may have activity include obesity, depression, schizophrenia, anxiety, obsessive compulsive disorder, addiction, panic disorders, sleep disorders, migraine, Type II diabetes, epilepsy, phobias and psychiatric syndromes.

DETAILED DESCRIPTION OF THE INVENTION

The following definitions are used, unless otherwise described:

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

The term "alkenyl" as used herein, alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl radical containing from 2 to 10 carbon atoms. Examples of such radicals include, but are not limited to, ethynyl, propynyl, propargyl, butynyl, hexynyl, decynyl and the like.

The term "alkoxy" as used herein, alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "halo" is defined herein to include fluoro, chloro, bromo, or iodo. Similarly, the term "halogen" is defined herein to include fluorine, chlorine, bromine, and iodine.

The term "amino", alone or in combination, includes the group —$NH_2$ or —$NR_aR_b$ wherein $R_a$ and $R_b$ are independently hydrogen, alkyl, alkylaryl, or aryl.

The term "aryl," alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of H, halo; CN, $NO_2$, $CF_3$, $N_3$, $C_{1-6}$alkyl, OH, $NR^aR^b$, $OC_{1-6}$alkyl, $OR^a$, $C(=O)NR^aR^b$, $C(=S)NR^aR^b$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, 13-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, $OC_{1-4}$alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "Het" generally represents a heterocyclic group, saturated or partially unsaturated, containing at least one heteroatom selected from the group consisting of oxygen, nitrogen, and sulfur, and optionally substituted with $C_{1-6}$alkyl or $C(=O)OR^6$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

Presently preferred compounds include 5-Chloro-1,2,3,3a,7,7a-hexahydro-4-thia-2-aza-cyclopenta[α]pentalene-6-carbonitrile, 5-Bromo-1,2,3,3a,7,7a-hexahydro-4-thia-2-aza-cyclopenta[α]pentalene-6-carbonitrile, 6-Chloro-5-methyl-1,2,3,3a,7,7a-hexahydro-4-thia-2-aza-cyclopenta[α]pentalene, 6-Bromo-5-methyl-3,3a,7,7a-tetrahydro-1H-4-thia-2-aza-cyclopenta[α]pentalene, 5-Chloro-6-methyl-1,2,3,3a,7,7a-hexahydro-4-thia-2-aza-cyclopenta[α]pentalene, 5-Bromo-6-methyl-1,2,3,3a,7,7a-hexahydro-4-thia-2-aza-cyclopenta[α]pentalene, 2-Bromo-3b,4,5,6,6a,7-hexahydro-1-thia-5-aza-cyclopenta[α]pentalene, 5-Chloro-6,7-dimethyl-1,2,3,3a,7,7a-hexahydro-4-thia-2-aza-cyclopenta[α]pentalene, 6-Bromo-1,2,3,3a,7,7a-hexahydro-4-thia-2-aza-cyclopenta[α]pentalene, 5-Bromo-1,2,3,3a,7,7a-hexahydro-4-thia-2-aza-cyclopenta[α]pentalene, 6-Bromo-5-trifluoromethyl-1,2,3,3a,7,7a-hexahydro-4-thia-2-aza-cyclopenta[α]pentalene, 6-Methyl-5-trifluoromethyl-1,2,3,3a,7,7a-hexahydro-4-thia-2-aza-cyclopenta[α]pentalene, 6-Methoxy-5-trifluoromethyl-1,2,3,3a,7,7a,-hexahydro-4-thia-2-aza-cyclopenta[α]pentalene and 4-Benzo[b]-1,2,3,3a,7,7a-Hexahydro-4-thia-2-aza-cyclopenta[α]-pentalene.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, farmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The compounds of the present invention may be prepared by the procedures set forth in Schemes 1 through 9. The general analytical conditions set forth after the Schemes were utilized in all examples.

Scheme 1: Scaffold diversification through the Gewald thiopene synthesis.

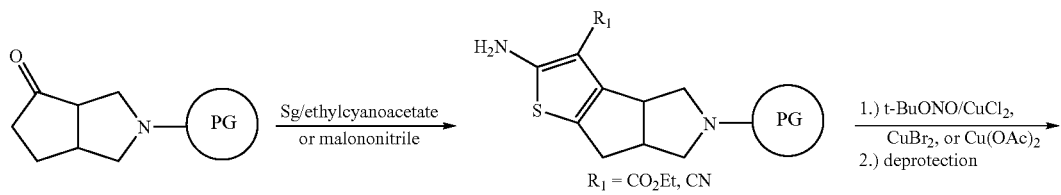

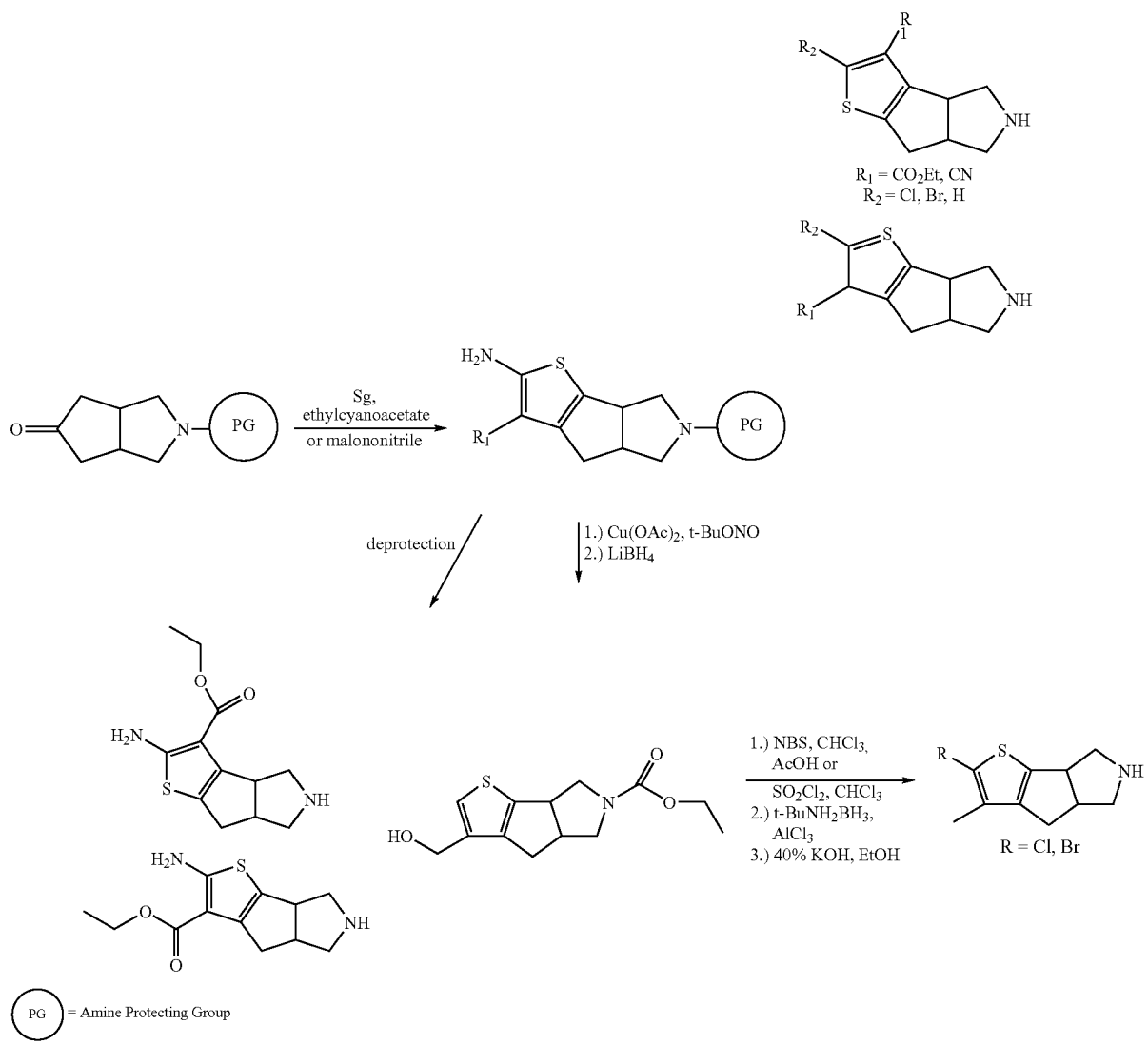
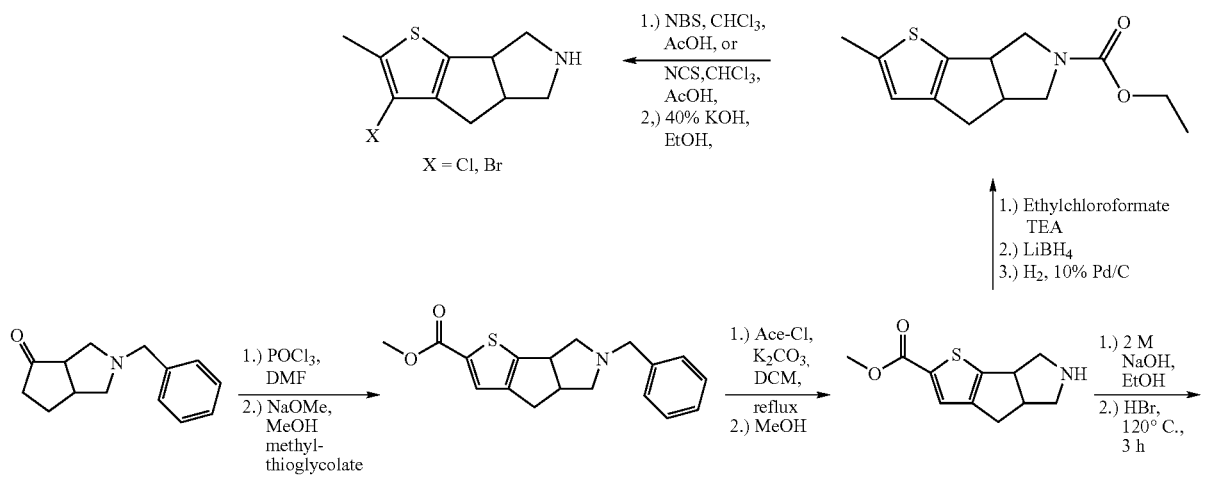
Scheme 2: Perkin condensation approach to the synthesis of select thiopene tricyclic-5, 5, 5 analogs.

-continued
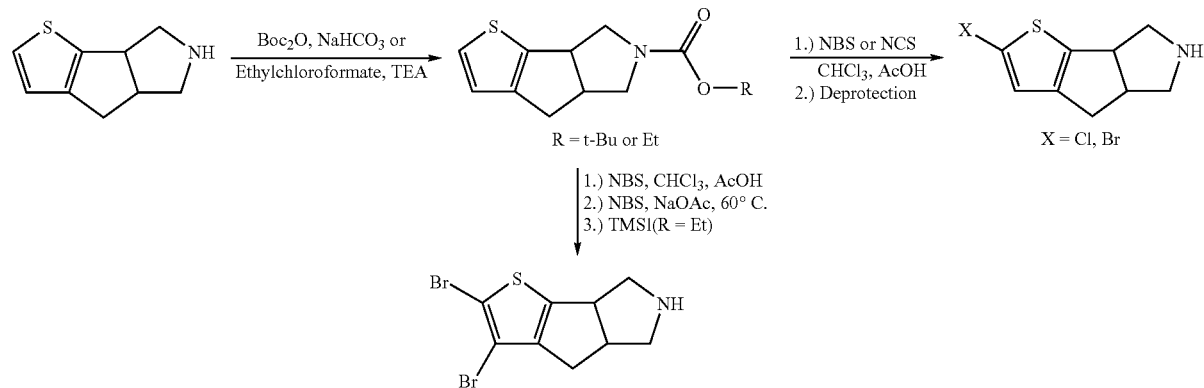
Scheme 3: Friedel-Crafts approach to the synthesis of substituted thiopene tricyclic-5, 5, 5 scaffold.
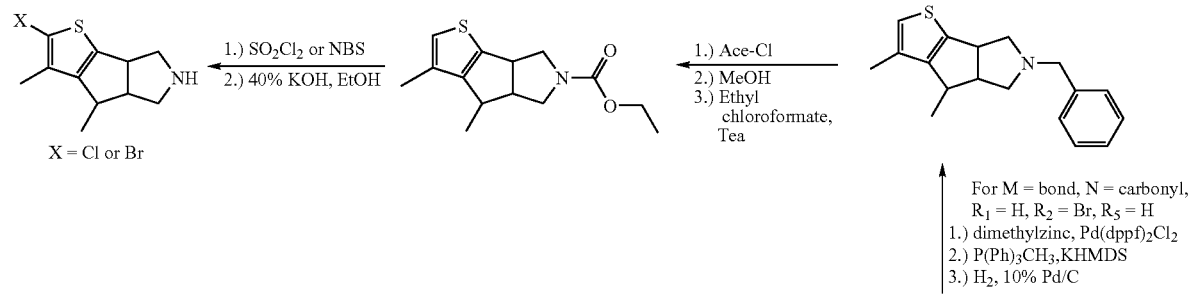
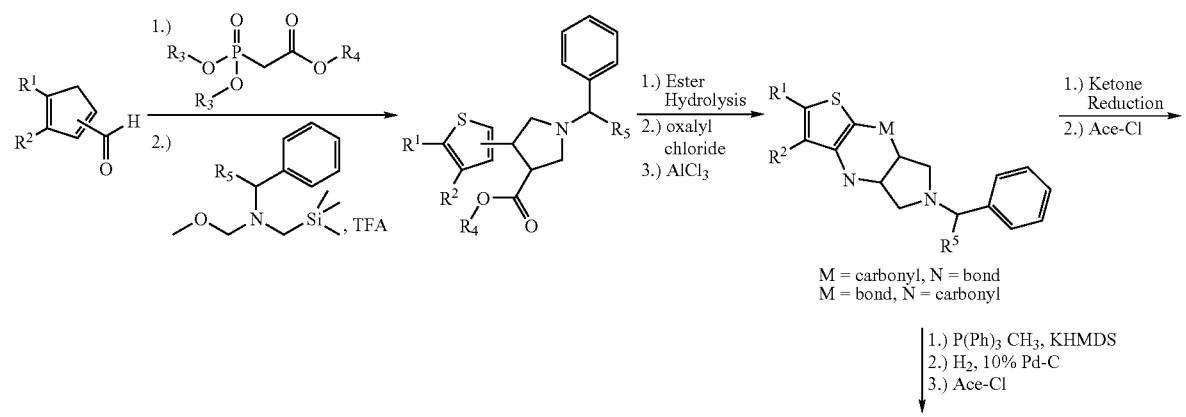

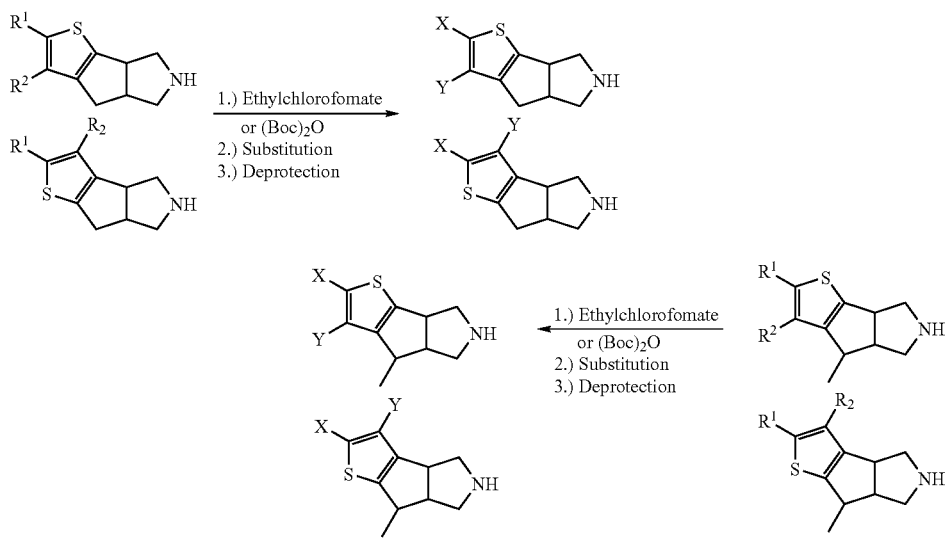
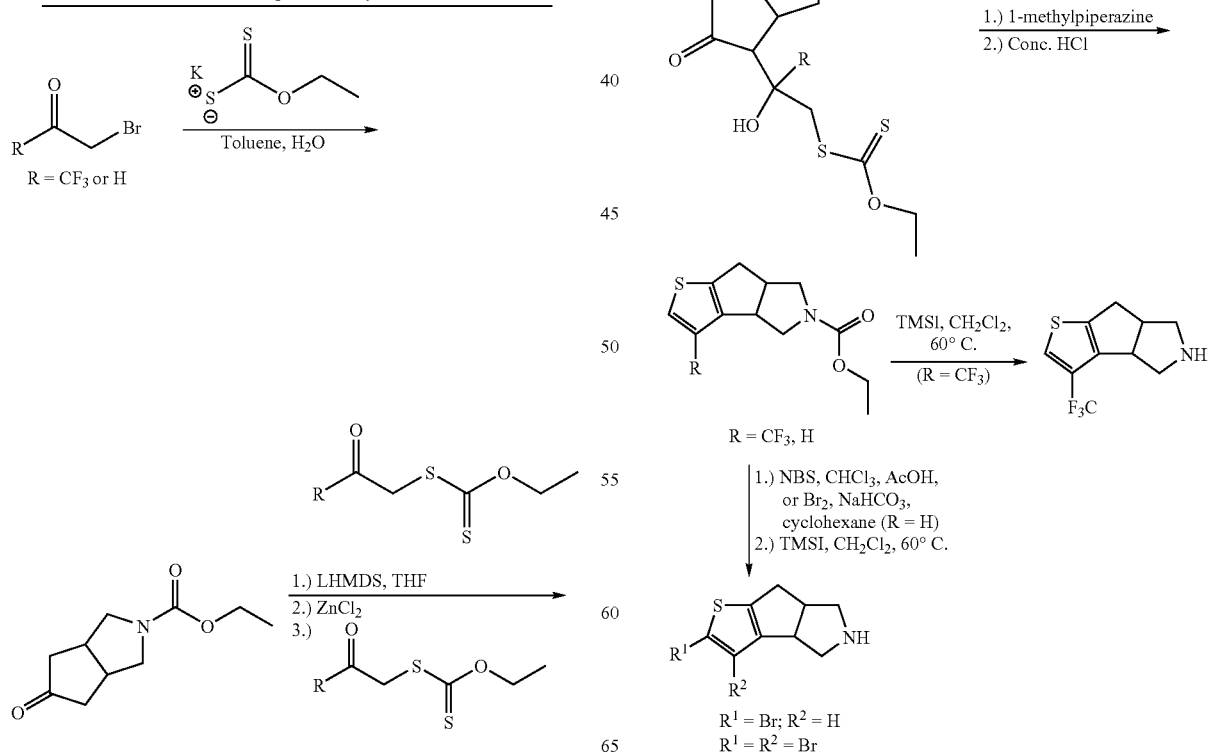
Scheme 4: Synthesis of tricyclic thiophene scaffold using modified Waldvogel chemistry.

Scheme 5: Synthesis of keto-thiophene tricyclic-5,5,6 ring system.
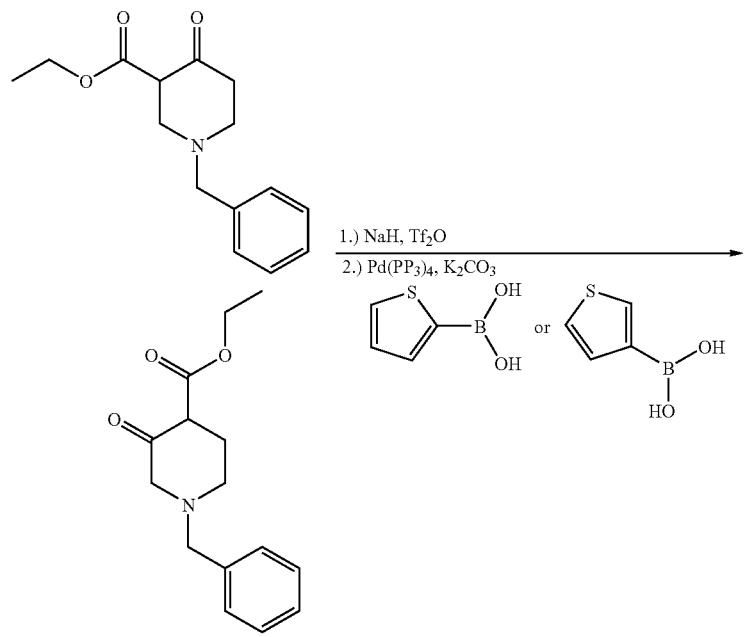
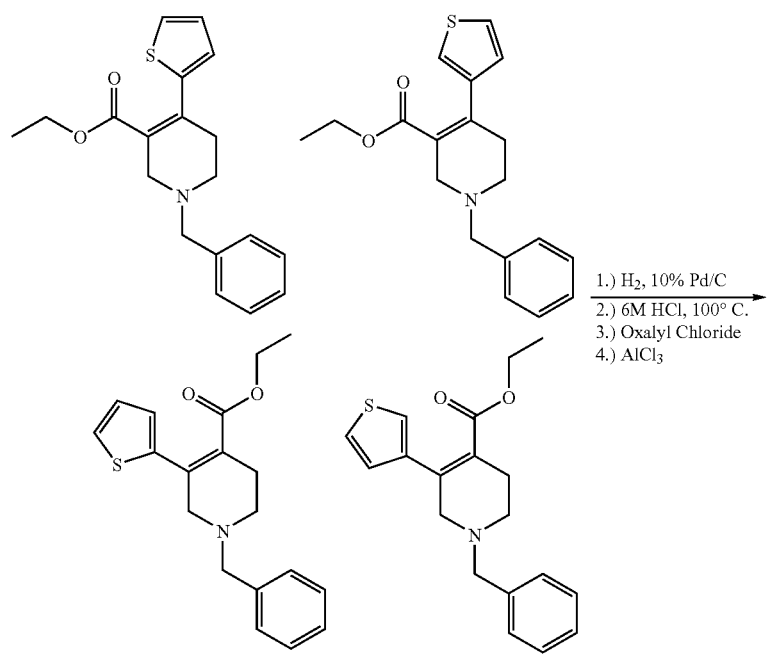

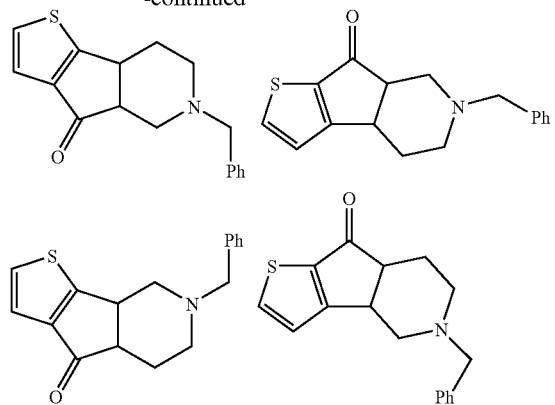
Scheme 6: Elaboration of keto-thiophene tricyclic-5,5,6 ring system into brominated final products.
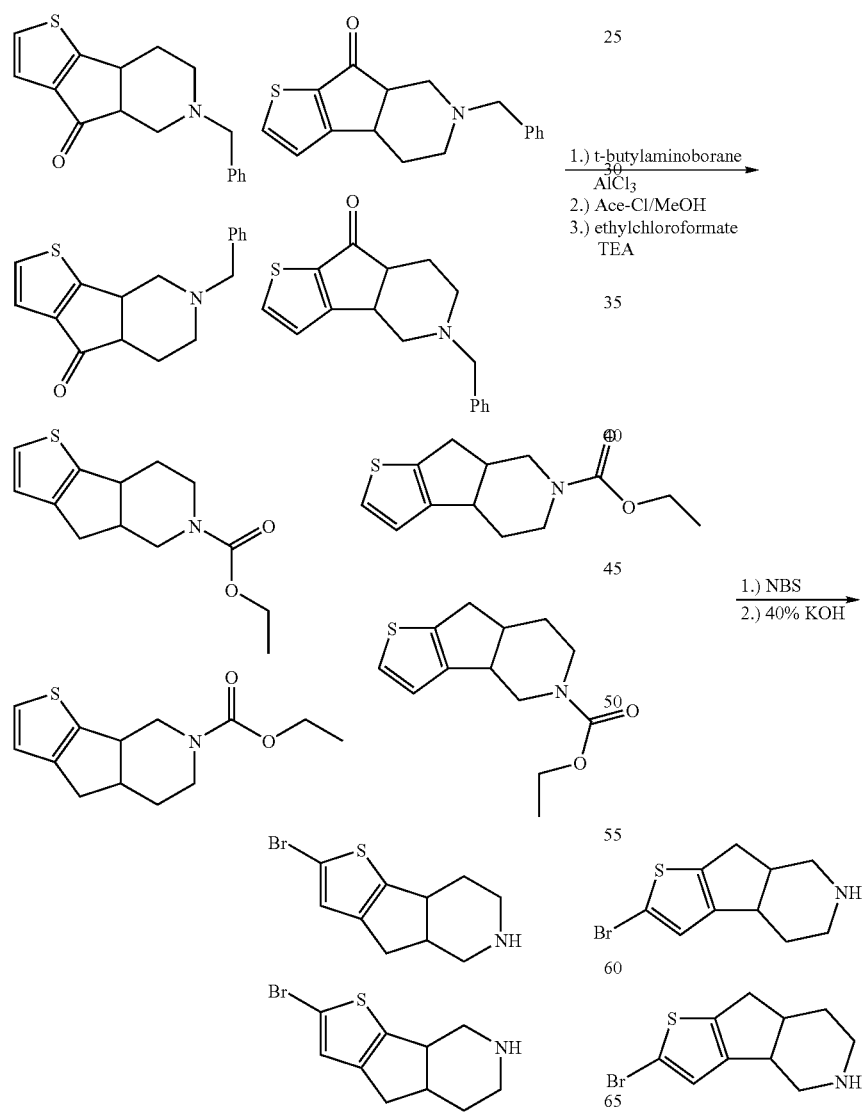

Scheme 7: Conversion of 2-Bromo 5,5,6 thiophene intermediates into 2-methyl-3-bromo analogs.
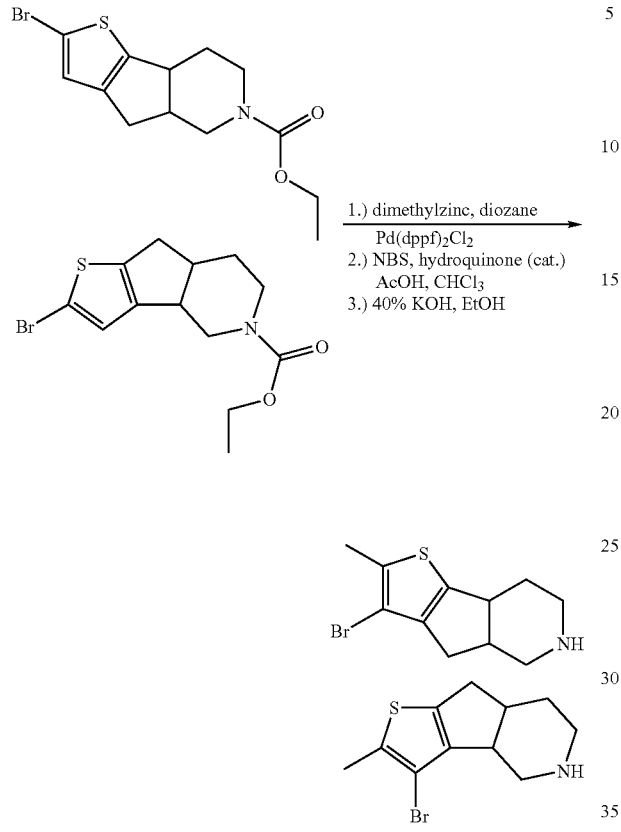
Scheme 8: Synthesis of the thiophene tricyclic-5,6,5 ring system (regioisomer 1) and associated analogs.
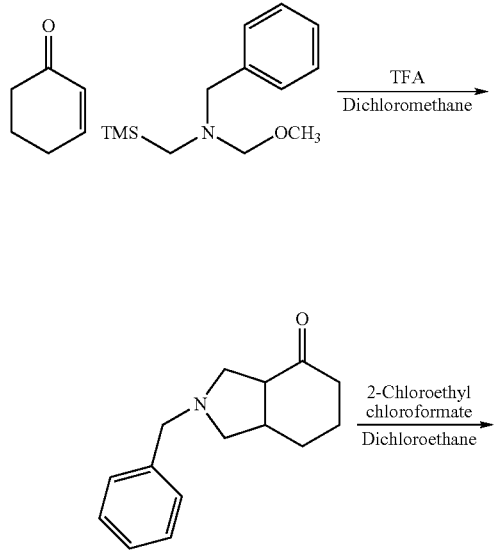
-continued
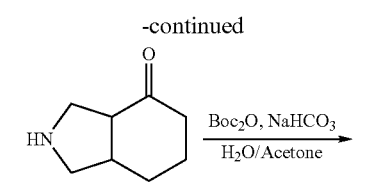
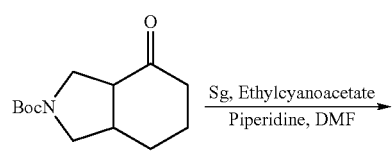
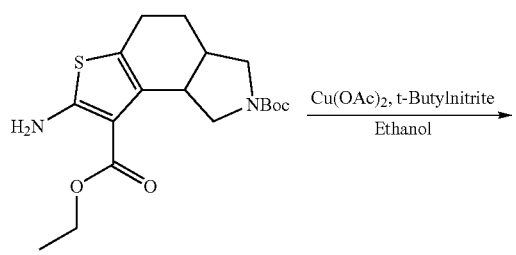
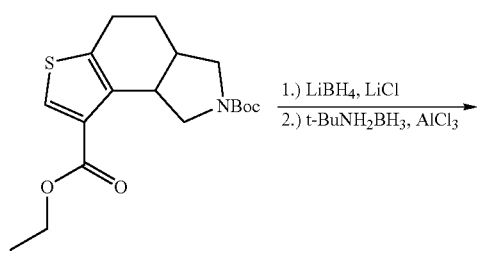
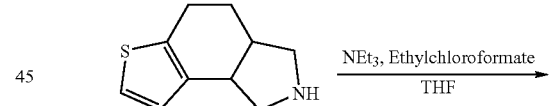
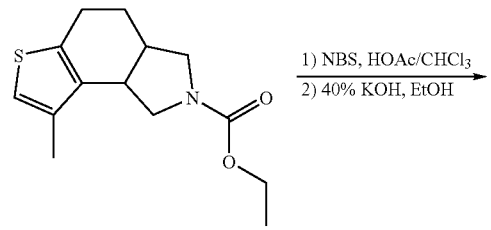
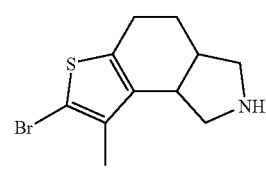

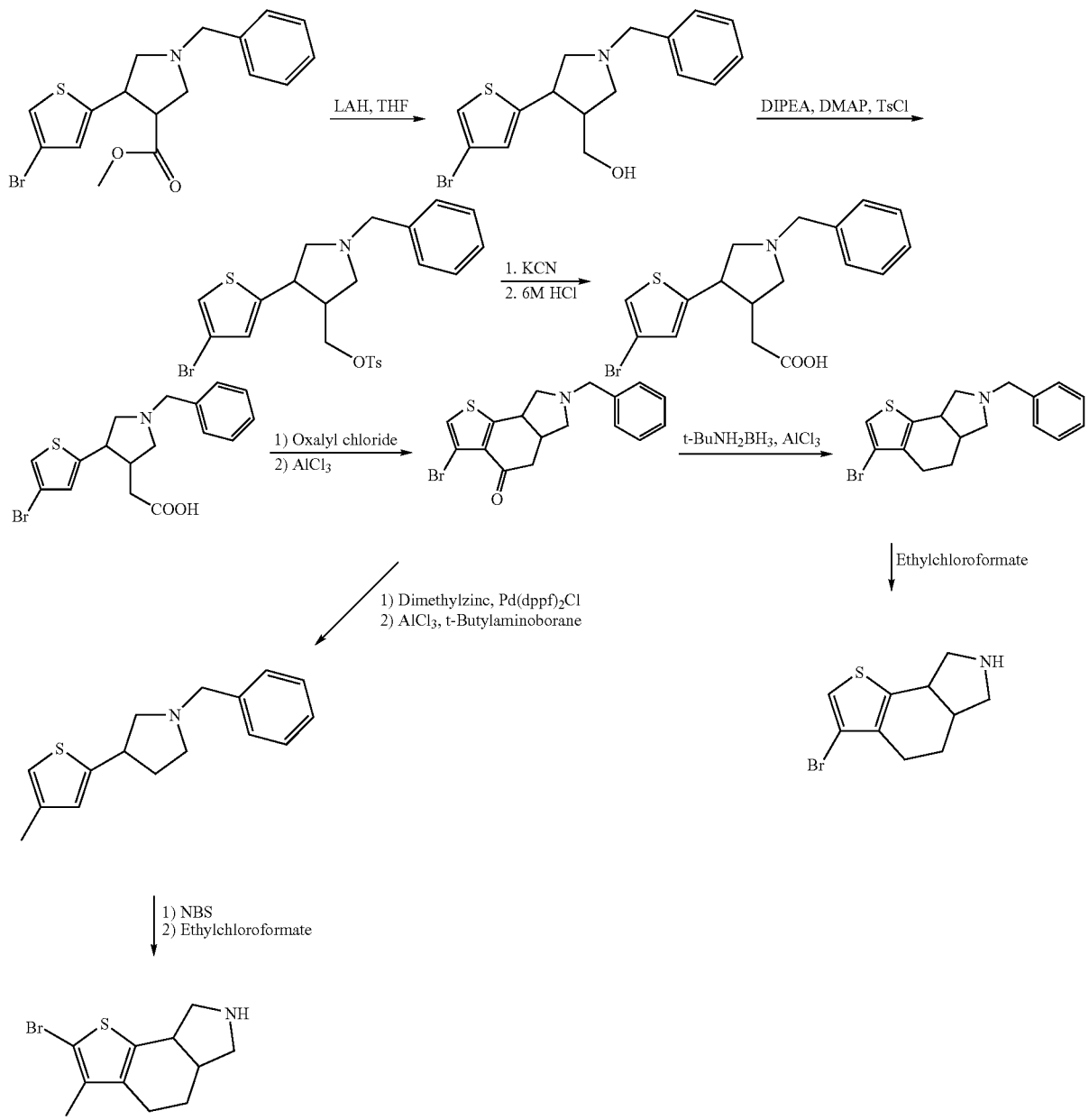

Scheme 9: Synthesis of the thiophene tricyclic-5,6,5 ring system (regioisomer 2) and associated analogs.

General Analytical Conditions

HPLC analysis and purification was performed using a Waters 2525 binary gradient pump, Waters 2767 sample manager, waters 2487 UV detector (220 and 254 nM), and Waters Micromass ZQ electrospray mass spec detector. The Micromass ZQ was set for both positive and negative ionization (cone voltage=25 and 50, respectively). Analytical HPLC analysis was performed as follows:

Waters XTerra MS C18 50×4.6 mm 3.5 μm column
Mobile Phase: 10 mM Ammonium Acetate buffer at pH 5.75 and Acetonitrile Acetonitrile: 10 to 75% at 3.5 minutes, 75 to 99% at 3.9 minutes, 99% hold to 4.2 minutes, 99 to 10% at 4.5 minutes, re-equilibrate.

Preparative HPLC was performed as follows:
Waters XTerra Prep MS C18 50×19 mm 5 μm column
Mobile Phase: 10 mM Ammonium Acetate buffer at pH 5.75 and Acetonitrile Acetonitrile: 10 to 99% at 8 minutes, 99% hold to 9 minutes, 99 to 10% at 9.5 minutes, re-equilibrate NMR analysis was performed using a Bruker BioSpin UltraShield NMR (300 MHz)

EXAMPLES

Example 1

5-Amino-1,2,3,3a,7,7a-hexahydro-4-thia-2-aza-cyclopenta[α]pentalene-6-carboxylic acid ethyl ester

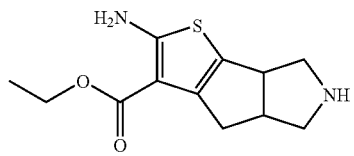

a.) 5-Amino-3,3a,7,7a-tetrahydro-1H-4-thia-2-aza-cyclopenta[α]pentalene-2,6-dicarboxylic acid 2-tert-butyl ester 6-ethyl ester (Scheme 1)

To a solution of 5-oxo-hexahydro-cyclopenta[c]pyrrole-2-carboxylic acid tert-butyl ester (2.87 g, 12.7 mmol) in anhydrous DMF (64 ml) was added sulfur (406 mg, 12.7 mmol), ethylcyanoacetate (1.43 g, 12.7 mmol), and piperidine (1.08 g, 12.7 mmol). The reaction mixture was stirred at 60° C. for 12 hours and then allowed to cool to room temperature. The reaction mixture was poured into brine (100 ml) and extracted with EtOAc (2×100 ml). The combined EtOAc layers were washed with brine (2×100 ml), dried (MgSO$_4$), and concentrated to give the subtitled compound as a brown solid. The crude product was purified by column chromatography (SiO$_2$) using a 0-100% ethyl acetate-hexanes gradient to afford the subtitled compound (4.28 g, 96%). $^1$H NMR (300 MHz, CDCl$_3$, ppm) 1.32 (t, J=7 Hz, 3H), 1.43 (s, 9H), 2.73 (br d, J=16 Hz, 1H), 2.98 (br dd, J$_1$=16 Hz, J$_2$=7 Hz, 1H), 3.18-3.32 (m, 2H), 3.38-3.63 (br m, 2H), 3.65-3.82 (br m, 2H), 4.24 (q, J=7 Hz, 2H), 5.93 (br s, 2H). MS calculated for C$_{17}$H$_{24}$N$_2$O$_4$S+H 353, observed 353.

b.) 5-Amino-1,2,3,3a,7,7a-hexahydro-4-thia-2-aza-cyclopenta[α]pentalene-6-carboxylic acid ethyl ester A solution of product from step a) (50 mg, 0.14 mmol) was stirred in HCl/dioxane (2 ml, 4.0 M) for 12 hours. The solvent was evaporated and the crude solid was purified by preparative HPLC to give the titled compound, which was converted to its hydrochloride salt and isolated. $^1$H NMR (300 MHz, CD$_3$OD, ppm) 1.31 (t, J=7 Hz, 3H), 2.79 (br d, J=16 Hz, 1H), 3.08-3.16 (m, 2H), 3.21-3.39 (m, 2H), 3.40-3.56 (m, 2H), 3.85-3.95 (br s, 1H), 4.20 (q, J=7 Hz, 2H). MS calculated for C$_{12}$H$_{16}$N$_2$O$_2$S+H 253, observed 253.

Example 2 and Example 3

5-Bromo-1,2,3,3a,7,7a-hexahydro-4-thia-2-aza-cyclopenta[α]pentalene-6-carboxylic acid ethyl ester and 1,2,3,3a,7,7a-Hexahydro-4-thia-2-aza-cyclopenta[α]pentalene-6-carboxylic acid ethyl ester

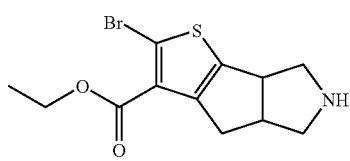

Example 2

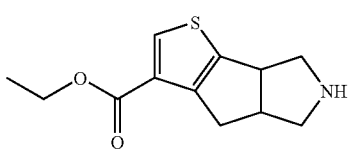

Example 3 a.) 5-Bromo-3,3a,7,7a-tetrahydro-1H-4-thia-2-aza-cyclopenta[a]pentalene-2,6-dicarboxylic acid 2-tert-butyl ester 6-ethyl ester and 3,3a,7,7a-Tetrahydro-1H-4-thia-2-aza-cyclopenta[α]pentalene-2,6-dicarboxylic acid 2-tert-butyl ester 6-ethyl ester (Scheme 1)

To a solution of tert-butylnitrite (1.01 ml, 8.52 mmol) in acetonitrile (28.4 ml) at 0° C. was added CuBr$_2$ (1.51 g, 6.82 mmol) and a solution of product from Example 1, step a) (2.0 g, 5.68 mmol) in acetonitrile (56 ml) dropwise over 30 minutes. The reaction mixture was stirred an additional 1 hour at 0° C. and then allowed to warm to room temperature. The reaction mixture was poured into brine (100 ml) and extracted with EtOAc (2×100 ml). The combined EtOAc layer was dried (MgSO$_4$), filtered, and concentrated providing a dark oil. The crude product was purified by column chromatography (SiO$_2$) using a 0-100% ethyl acetate-hexanes gradient to afford the subtitled compounds as an inseparable mixture in a 1:1 ratio based on the HPLC (629 mg, 29%).

b.) 5-Bromo-1,2,3,3a,7,7a-hexahydro-4-thia-2-aza-cyclopenta[α]pentalene-6-carboxylic acid ethyl ester and 1,2,3,3a,7,7a-Hexahydro-4-thia-2-aza-cyclopenta[α]pentalene-6-carboxylic acid ethyl ester The title compounds were prepared by the method of Example 1, step b utilizing the products from step a). Example 2: $^1$H NMR (300 MHz, DMSO, ppm) 1.29 (t, J=7 Hz, 3H), 2.86 (br d, J=16 Hz, 1H), 2.99-3.28 (m, 3H), 3.32-3.59 (m, 3H), 3.95-4.05 (m, 1H), 4.25 (q, J=7 Hz, 2H), 9.0-9.3 (br s, 1H), 9.8-10.0 (br s, 1H), MS calculated for C$_{12}$H$_{14}$BrNO$_2$S+H 317, observed 317. Example 3: $^1$H NMR (300 MHz, DMSO, ppm) 1.27 (t, J=7 Hz, 3H), 2.77 (br m, 1H), 2.99-3.25 (m, 3H), 3.35-3.49 (m, 3H), 3.53-3.68 (m, 1H), 3.95-4.05 (m, 1H), 4.22 (q, J=7 Hz, 2H), 8.26 (s, 1H), 9.05-9.2 (br s, 1H), 9.55-9.70 (br s, 1H), MS calculated for C$_{12}$H$_{15}$NO$_2$S+H 238, observed 238.

Example 4

5-Chloro-1,2,3,3a,7,7a-hexahydro-4-thia-2-aza-cyclopenta[α]pentalene-6-carboxylic acid ethyl ester

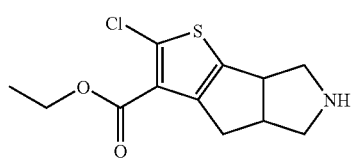

a.) 5-Chloro-3,3a,7,7a-tetrahydro-1H-4-thia-2-aza-cyclopenta[α]pentalene-2,6-dicarboxylic acid 2-tert-butyl ester 6-ethyl ester (Scheme 1)

The subtitled compound was prepared by the method of Example 2, step a utilizing the product of Example 1, step a) and CuCl$_2$.

b.) 5-Chloro-1,2,3,3a,7,7a-hexahydro-4-thia-2-aza-cyclopenta[α]pentalene-6-carboxylic acid ethyl ester The title compound was prepared by the method of Example 1, step b) utilizing the product from step a: $^1$H NMR (free base) (300 MHz, CDCl$_3$, ppm) 1.48 (t, J=7 Hz, 3H), 2.80-2.90 (br d, 1H), 2.92-2.99 (m, 1H), 3.08-3.28 (m, 2H), 3.32-3.52 (m, 3H), 3.85-3.96 (br m, 1H), 4.32 (q, J=7 Hz, 2H), 5.20 (br s, 1H), MS calculated for C$_{12}$H$_{14}$ClNO$_2$S+H 272, observed 272.

Example 5

(5-Amino-1,2,3,3a,7,7a-hexahydro-4-thia-2-aza cyclopenta[α]-pentalen-6-yl)-(3-trifluoromethyl-phenyl)-methanone

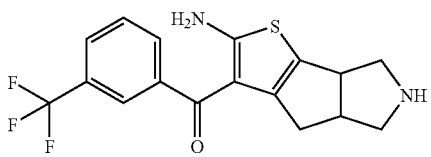

a.) 5-Amino-6-(3-trifluoromethyl-benzoyl)-3,3a,7,7a-tetrahydro-1H-4-thia-2-aza-cyclopenta[α]pental-ene-2-carboxylic acid tert-butyl ester (Scheme 1)

The subtitled compound was prepared by the method of Example 1, step a) utilizing 5-oxo-hexahydro-cyclopenta[c]pyrrole-2-carboxylic acid tert-butyl ester, sulfur, and 3-(trifluoromethyl)benzoylacetonitrile: (48.1 mg, 12%), $^1$H NMR (300 MHz, CDCl$_3$, ppm) 1.43 (s, 9H), 1.65-1.81 (br m, 1H), 2.37 (ddd, J$_1$=16 Hz, J$_2$=7 Hz, J$_3$=2 Hz, 1H), 2.82-3.0 (br m, 1H), 3.05-3.2 (br m, 1H), 3.42-3.7 (br m, 4H), 7.10 (br s, 1H), 7.20 (br s, 1H), 7.52-7.60 (m, 1H), 7.62-7.77 (m, 3H), MS calculated for C$_{22}$H$_{23}$F$_3$N$_2$O$_3$S–H 451, observed 451.

b.) (5-Amino-1,2,3,3a,7,7a-hexahydro-4-thia-2-aza cyclopenta[α]-pentalen-6-yl)-(3-trifluoromethyl-phenyl)-methanone hydrochloride The title compound was prepared by the method of Example 1, step b) utilizing the product from step a. MS calculated for C$_{17}$H$_{15}$F$_3$N$_2$OS+H 353, observed 353.

Example 6

(5-Amino-1,2,3,3a,7,7a-hexahydro-4-thia-2-aza-cyclopenta[α]-pentalen-6-yl)-p-tolyl-methanone

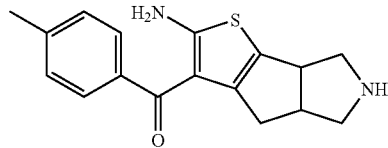

a.) 5-Amino-6-(4-methyl-benzoyl)-3,3a,7,7a-tetrahydro-1H-4-thia-2-aza cyclopenta[α]pentalene-2-carboxylic acid tert-butyl ester (Scheme 1)

The subtitled compound was prepared by the method of Example 1, step a) utilizing 5-oxo-hexahydro-cyclopenta[c]pyrrole-2-carboxylic acid tert-butyl ester, sulfur, and 4-methylbenzoylacetonitrile: (99.1 mg, 28%), $^1$H NMR (300 MHz, CDCl$_3$, ppm) 1.43 (s, 9H), 1.77-1.98 (br m, 1H), 2.38-2.52 (m, 4H), 2.79-3.04 (br m, 1H), 3.04-3.18 (br m, 1H), 3.40-3.70 (br m, 4H), 6.90 (br s, 1H), 7.01 (br s, 1H), 7.21 (d, J=8 Hz, 1H), 7.42 (d, J=8 Hz, 1H), MS calculated for C$_{22}$H$_{26}$N$_2$O$_3$S–H 397, observed 397.

b.) (5-Amino-1,2,3,3a,7,7a-hexahydro-4-thia-2-aza-cyclopenta[α]pentalen-6-yl)-p-tolyl-methanone The title compound was prepared by the method of Example 1, step b) utilizing the product from step a. MS calculated for C$_{17}$H$_{18}$N$_2$OS+H 299, observed 299.

Example 7

(5-Amino-1,2,3,3a,7,7a-hexahydro-4-thia-2-aza-cyclopenta[α]-pentalen-6-yl)-(4-chloro-phenyl)-methanone

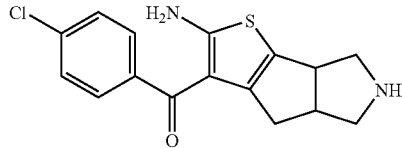

a.) 5-Amino-6-(4-chloro-benzoyl)-3,3a,7,7a-tetrahydro-1H-4-thia-2-aza-cyclopenta[α]pentalene-2-carboxylic acid tert-butyl ester (Scheme 1)

The subtitled compound was prepared by the method of Example 1, step a) utilizing 5-oxo-hexahydro-cyclopenta[c]pyrrole-2-carboxylic acid tert-butyl ester, sulfur, and 4-chlorobenzoylacetonitrile: (28.2 mg, 7.6%), MS calculated for C$_{21}$H$_{23}$ClN$_2$O$_3$S–H 417, observed 417.

b.) (5-Amino-1,2,3,3a,7,7a-hexahydro-4-thia-2-aza-cyclopenta[α]-pentalen-6-yl)-(4-chloro-phenyl)-methanone hydrochloride The title compound was prepared by the method of example 1, step b) utilizing the product from step a. MS calculated for C$_{17}$H$_{18}$N$_2$OS+H 299, observed 299.

Example 8

1,2,3,3a,7,7a-Hexahydro-4-thia-2-aza-cyclopenta[α]pentalene-5-carboxylic acid methyl ester

a.) 2-Benzyl-6-chloro-1,2,3,3a,4,6a-hexahydro-cyclopenta[c]pyrrole-5-carbaldehyde (Scheme 2)

To an anhydrous solution of DMF (20 ml) at 0° C. was added phosphorusoxychloride (POCl$_3$) (29.8 mmol, 2.77 ml) dropwise over 5 minutes. The solution was warmed to room temperature and stirred for 30 minutes. The mixture was cooled to 0° C. and a solution of 2-benzyl-hexahydro-cyclopenta-[c]pyrrol-4-one[i] (4 g, 18.6 mmol) in anhydrous DMF (5 ml) was added dropwise over 5 minutes. After the addition was complete, the reaction mixture was warmed to room temperature and stirred for 1 hour. The crude reaction mixture was poured into ice water (200 ml) and neutralized carefully with solid NaHCO$_3$ to pH 8. The mixture was extracted with EtOAc (2×200 ml). The combined EtOAc layers were washed with brine (100 ml), dried (MgSO$_4$), filtered, and concentrated providing the subtitled compound as a brown oil (4.55 g, 93%). This oil was used immediately without further purification. $^1$H NMR (300 MHz, CDCl$_3$, ppm) 2.30-2.50 (br m, 4H), 2.60-2.75 (m, 2H), 3.40-3.75 (m, 4H), 7.30 (s, 5H), 9.98 (s, 1H).

[i] Flynn et al., Tetrahedron Lett., 33, 1992, 7281.
[j] Miyajima et al., Chem. Pharm. Bull., 39, 1991, 3175.

b.) 2-Benzyl-1,2,3,3a,7,7a-hexahydro-4-thia-2-aza-cyclopenta[α]pentalene-5-carboxylic acid methyl ester To a solution of the product from step a) (4.55 g, 17.4 mmol) in anhydrous MeOH (46 ml) was added methylthioglycolate (1.63 ml, 18.27 mmol) and sodium methoxide (990 mg, 18.34 mmol). The reaction mixture was stirred at room temperature for 18 hours. The solvent was evaporated in vacuo and the crude residue was dissolved in EtOAc (200 ml) and washed with H$_2$O (2×75 ml), dried (MgSO$_4$), filtered, and evaporated. The crude product was purified by column chromatography (SiO$_2$) using a 0-35% ethyl acetate-hexanes gradient to afford the subtitled compound as a clear oil (2.88 g, 53%). MS calculated for C$_{18}$H$_{19}$NO$_2$S+H 314, observed 314.

c.) 1,2,3,3a,7,7a-Hexahydro-4-thia-2-aza-cyclopenta[α]pentalene-5-carboxylic acid methyl ester To a solution of the product from step b) (100 mg, 0.32 mmol) in DCE (1.6 ml) was added powdered K$_2$CO$_3$ (176 mg, 1.28 mmol) and ACE-Cl (183 mg, 1.28 mmol). The reaction mixture was heated to 80° C. and stirred for 18 hours. The reaction was cooled to room temperature, filtered, and concentrated in vacuo. The crude oil was dissolved in anhydrous MeOH (2.5 ml) and stirred at room temperature for 3 hours. The solvent was evaporated and the product triturated with anhydrous ether to give a white solid, which was filtered to give the titled compound as its hydrochloride salt: (42.3 mg, 51%), $^1$H NMR (300 MHz, DMSO, ppm) 2.68 (br d, J=16 Hz, 1H), 2.98-3.06 (m, 2H), 3.19-3.28 (m, 1H), 3.35-3.50 (m, 2H), 3.52-3.62 (m, 1H), 3.80 (s, 3H), 4.00-4.11 (m, 1H), 7.56 (s, 1H), 9.05 (br s, 1H), 9.31 (br s, 1H). MS calculated for C$_{11}$H$_{13}$NO$_2$S+H 224, observed 224.

Example 9

1,2,3,3a,7,7a-Hexahydro-4-thia-2-aza-cyclopenta[α]pentalene

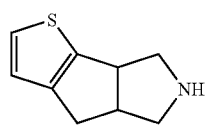

a.) 1,2,3,3a,7,7a-Hexahydro-4-thia-2-aza-cyclopenta[α]pentalene-5-carboxylic acid (Scheme 2)

To a solution of the product from example 8, step c) (222 mg, 0.99 mmol) in MeOH (5 ml) was added KOH (0.5 ml). The reaction mixture was stirred for 2 hours at room temperature and evaporated to dryness. The residue was dissolved in HCl (2.5 M, 10 ml) and extracted with EtOAc (1×30 ml). The aqueous layer was separated and evaporated to dryness to give the subtitled compound as a salt mixture. MS calculated for C$_{10}$H$_{11}$NO$_2$S+H 210, observed 210.

b.) 1,2,3,3a,7,7a-Hexahydro-4-thia-2-aza-cyclopenta[α]pentalene

The product of step a) was dissolved in hydrobromic acid (48%, 20 ml) and heated to 106° C. for 3 hours. The reaction mixture was cooled to room temperature and extracted with ether (20 ml). The aqueous layer was cooled to 0° C. and carefully brought to pH 12 by dropwise addition of concentrated KOH. The basic aqueous layer was extracted with EtOAc (2×50 ml). The combined organic extracts were dried (MgSO$_4$), filtered, and evaporated to give the titled compound (106 mg, 64%). MS calculated for C$_9$H$_{11}$NS+H 166, observed 166.

Example 10

2-Chloro-3b,4,5,6,6a,7-hexahydro-1-thia-5-aza-cyclopenta[α]pentalene-3-carbonitrile

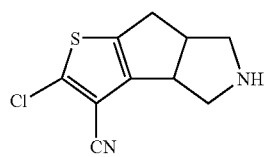

a.) Hexahydro-cyclopenta[c]pyrrol-4-one hydrochloride (Scheme 1)

The subtitled compound was prepared by treatment of 2-Benzyl-hexahydro-cyclopenta[c]pyrrol-4-one under the conditions described in Example 8, step c) gave 278 mg (74%) of the subtitled compound as a white foam.

b.) 4-Oxo-hexahydro-cyclopenta[c]pyrrole-2-carboxylic acid tert-butyl ester

The subtitled compound was prepared from the product of step a) (278 mg, 1.72 mmol) in acetone (3 ml) and H$_2$O (3 ml) was added NaHCO$_3$ (290 mg, 3.45 mmol) and di-tert-butyl dicarbonate (412 mg, 1.89 mmol). The reaction mixture was stirred for 1 hour at room temperature. The reaction mixture was diluted with EtOAc (100 ml) and washed with brine (50 ml), dried (MgSO$_4$), filtered, and concentrated to give the crude product that was passed through a silica gel plug eluting with ethyl acetate (100 ml) to give 211 mg (54%) of the subtitled product as a clear oil.

c.) 2-Amino-3-cyano-3b,6,6a,7-tetrahydro-4H-1-thia-5-aza-cyclopenta[α]pentalene-5-carboxylic acid tert-butyl ester Following the method of Example 1, step a) 4-Oxo-hexahydro-cyclopenta[c]pyrrole-2-carboxylic acid tert-butyl ester (211 mg, 0.94 mmol) was combined with malononitrile (62 mg, 0.94 mmol), S$_8$ (30.1 mg, 0.94 mmol), DMF (4.7 ml) and piperidine (80 mg, 0.94 mmol). The contents were heated to 60° C. for 3 hours and then worked up as previously described in Example 1, step a. The crude oil was dissolved in hexanes:EtOAc (7:3) and passed through a plug of silica gel providing the subtitled compound as a dark orange oil (181 mg, 63%). MS calculated for C15H19N3O2S–H 304, observed 304.

d.) 2-Chloro-3-cyano-3b,6,6a,7-tetrahydro-4H-1-thia-5-aza-cyclopenta[α]pentalene-5-carboxylic acid tert-butyl ester The subtitled compound was prepared by the method of Example 2, step a) utilizing the product of step c) and CuCl$_2$.

e.) 2-Chloro-3b,4,5,6,6a,7-hexahydro-1-thia-5-aza-cyclopenta[α]pentalene-3-carbonitrile The title compound was prepared as its HCl salt by the method of Example 1, step b) utilizing the product of step d). $^1$H NMR (300 MHz, CDCl$_3$, ppm) 2.75-2.82 (m, 1H); 2.92-3.05 (m, 1H); 3.12-3.45 (m, 4H); 3.50-3.62 (m, 1H); 3.82-3.95 (m, 1H); 7.10-7.30 (br s, 2H); MS calculated for C10H9ClN2S+H 225, observed 225.

Example 11

2-Bromo-3b,4,5,6,6a,7-hexahydro-1-thia-5-aza-cyclopenta[α]pentalene-3-carbonitrile

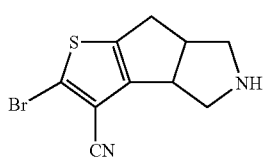

a.) 2-Bromo-3-cyano-3b,6,6a,7-tetrahydro-4H-1-thia-5-aza-cyclopenta[α]pentalene-5-carboxylic acid tert-butyl ester (Scheme 1)

The subtitled compound was prepared by the method of Example 2, step a) utilizing the product of example 10, step c) and CuBr$_2$.

b.) 2-Bromo-3b,4,5,6,6a,7-hexahydro-1-thia-5-aza-cyclopenta[α]pentalene-3-carbonitrile The title compound was prepared as its HCl salt by the method of Example 1, step b) utilizing the product of step a) $^1$H NMR (300 MHz, CDCl$_3$, ppm) 2.75-2.82 (m, 1H); 2.95-3.05 (m, 1H); 3.15-3.45 (m, 4H); 3.50-3.70 (m, 1H); 3.85-3.98 (m, 1H); 7.60-7.80 (br s, 2H); MS calculated for C10H9BrN2S+H 269, observed 269, 271.

Example 12

5-Chloro-1,2,3,3a,7,7a-hexahydro-4-thia-2-aza-cyclopenta[α]pentalene-6-carbonitrile

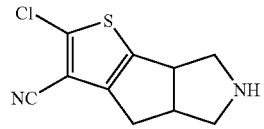

a.) 5-Amino-6-cyano-3,3a,7,7a-tetrahydro-1H-4-thia-2-aza-cyclopenta[α]pentalene-2-carboxylic acid ethyl ester (Scheme 1)

Following the method of Example 1, step a) 5-Oxo-hexahydro-cyclopenta[c]pyrrole-2-carboxylic acid ethyl ester (500 mg, 2.54 mmol) was combined with malononitrile (168 mg, 2.54 mmol), S$_8$ (81.3 mg, 2.54 mmol), DMF (12.7 ml) and piperidine (216 mg, 2.54 mmol). The contents were heated to 60° C. for 3 hours and then worked up as previously described. The crude oil was dissolved in hexanes:EtOAc (1:1) and passed through a plug of silica gel providing 560 mg (80%) of the subtitled product as a dark orange oil. MS calculated for C13H15N3O2S–H 276, observed 276.

b.) 5-Chloro-6-cyano-3,3a,7,7a-tetrahydro-1H-4-thia-2-aza-cyclopenta[α]pentalene-2-carboxylic acid ethyl ester The subtitled compound was prepared by the method of Example 2, step a) utilizing the product of step a) and CuCl$_2$.

c.) 5-Chloro-1,2,3,3a,7,7a-hexahydro-4-thia-2-aza-cyclopenta[α]pentalene-6-carbonitrile The product of step b) (13.9 mg, 0.047 mmol) was treated with iodotrimethylsilane (10 μl, 0.07 mmol) in CH$_2$Cl$_2$ (235 μl) at 50° C. for 16 hours. The solvent was concentrated and the residue was dissolved in MeOH and purified by preparative LC/MS providing the title compound as a white solid. $^1$H NMR (300 MHz, CD$_3$OD, ppm) 2.80-2.90 (m, 1H); 3.10-3.50 (m, 5H); 3.55-3.70 (m, 1H); 4.00-4.21 (m, 1H); MS calculated for C10H9ClN2S+H 225, observed 225.

Example 13

5-Bromo-1,2,3,3a,7,7a-hexahydro-4-thia-2-aza-cyclopenta[α]pentalene-6-carbonitrile

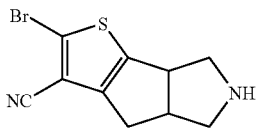

a.) 5-Bromo-6-cyano-3,3a,7,7a-tetrahydro-1H-4-thia-2-aza-cyclopenta[α]pentalene-2-carboxylic acid ethyl ester (Scheme 1)

The subtitled compound was prepared by the method of Example 2, step a) utilizing the product of example 12, step a) and CuBr$_2$.

b.) 5-Bromo-1,2,3,3a,7,7a-hexahydro-4-thia-2-aza-cyclopenta[α]pentalene-6-carbonitrile The title compound was prepared by the method of Example 12, step c) utilizing the product of step a). $^1$H NMR (300 MHz, CDCl$_3$, ppm) 2.73-2.83 (m, 1H); 2.97-3.05 (m, 1H); 3.12-3.22 (m, 2H); 3.32-3.45 (m, 2H); 3.52-3.65 (m, 1H); 3.90-4.00 (m, 1H) 7.50-7.70 (br s, 2H); MS calculated for C10H9BrN2S+H 269, observed 269, 271.

Example 14

1,2,3,3a,7,7a-Hexahydro-4-thia-2-aza-cyclopenta[α]pentalene-6-carbonitrile

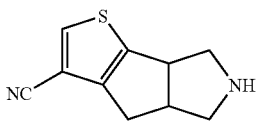

a.) 6-Cyano-3,3a,7,7a-tetrahydro-1H-4-thia-2-aza-cyclopenta[α]pentalene-2-carboxylic acid ethyl ester (Scheme 1)

The product from Example 12, step a) (105 mg, 0.38 mmol) was dissolved in EtOH (1.9 ml) and treated with t-butyl nitrite (59 mg, 0.57 mmol) followed by Cu(OAc)$_2$ (103 mg, 0.57 mmol). The contents were heated to 60° C. for 1 hour and then the reaction mixture was cooled and the EtOH was concentrated. The residue was partitioned between brine (5 ml) and EtOAc (10 ml). The brine layer was washed with EtOAc (4×10 ml) and the combined organic layers were dried (MgSO$_4$), filtered and concentrated. The crude residue was passed through a plug of silica gel (7:3) hexanes:EtOAc (150 ml) providing the subtitled product as an orange oil (26.7 mg, 27%). MS calculated for C13H14N2O2S+H 263, observed 263.

b.) 1,2,3,3a,7,7a-Hexahydro-4-thia-2-aza-cyclopenta[α]pentalene-6-carbonitrile

The title compound was prepared following the procedure outlined in Example 12, step c) utilizing the product of step a). MS calculated for C10H10N2S+H 191, observed 191.

Example 15

6-Chloro-5-methyl-1,2,3,3a,7,7a-hexahydro-4-thia-2-aza-cyclopenta[α]pentalene

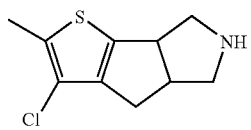

a.) 3,3a,7,7a-Tetrahydro-1H-4-thia-2-aza-cyclopenta[α]pentalene-2,5-dicarboxylic acid 2-ethyl ester 5-methyl ester (Scheme 2)

The hydrochloride salt of Example 8, step c) (2.21 g, 8.5 mmol) was dissolved in CH$_2$Cl$_2$ (42 ml) and treated with triethylamine (3.55 ml, 25.5 mmol) and ethyl chloroformate (1.11 g, 10.2 mmol) at 0° C. for 1 hour. The reaction mixture was poured into water (100 ml) and extracted with EtOAc (2×50 ml). The combined organic extracts were washed with 10% citric acid (25 ml), sat. NaHCO$_3$ (25 ml) and dried (MgSO$_4$). The crude product was passed through a plug silica gel using 50:50 hexanes:EtOAc providing the subtitled product as a clear oil (2.2 g, 90%). MS calculated for C14H17NO4S+H 296, observed 296.

b.) 5-Hydroxymethyl-3,3a,7,7a-tetrahydro-1H-4-thia-2-aza-cyclopenta [α]pentalene-2-carboxylic acid ethyl ester The product of step a) (500 mg, 1.69 mmol) was dissolved in THF (9 ml) and treated with a 2.0 M solution of LiBH$_4$ in THF (5.07 mmol, 10.1 mmol) followed by LiCl (213 mg, 5.07 mmol) and the mixture was refluxed for 16 hours. Next, the mixture was cooled to 0° C. and quenched with two drops of AcOH followed by dropwise addition of water. After the effervescence subsided the contents were extracted with EtOAc (2×40 ml). The combined organic layers were washed sat. NaHCO$_3$ (30 ml), brine (30 ml) and dried (MgSO$_4$) providing the crude subtitled product as an oil. MS calculated for C14H17NO4S+H 268, observed M—H$_2$O 250.

c.) 5-Methyl-3,3a,7,7a-tetrahydro-1H-4-thia-2-aza-cyclopenta[α]pentalene-2-carboxylic acid ethyl ester The product of step b) was dissolved in EtOAc (50 ml) and 10% Pd/C (1 gram) was added. The flask was evacuated and purged four times with N$_2$ and then a balloon of H$_2$ was added and the reaction was stirred for 24 hours at room temperature. Next, the mixture was passed through a pad of celite and the solvent was concentrated providing the subtitled product that was used without further purification.

d.) 6-Chloro-5-methyl-3,3a,7,7a-tetrahydro-1H-4-thia-2-aza-cyclopenta[α]pentalene-2-carboxylic acid ethyl ester The product of step c) (74.2 mg, 0.30 mmol) was placed in a vial and diluted with CHCl$_3$ (740 μl) and AcOH (740 μl). Next, hydroquinone (~5 mg) was added followed by NCS (41.3 mg, 0.31 mmol) and the contents were heated to 40° C. for 6 hours. The crude reaction mixture was diluted with water (2 ml) and extracted with EtOAc (3×3 ml). The organic layer was dried (MgSO$_4$) and purified by preparative TLC using hexanes/EtOAc 50:50 providing subtitled product. MS calculated for C$_{13}$H$_{16}$ClNO2S+H 286, observed 286.

e.) 6-Chloro-5-methyl-1,2,3,3a,7,7a-hexahydro-4-thia-2-aza-cyclopenta[α]pentalene The product of step d) was treated with 40% aqueous KOH in EtOH at 105° C. for 16 hours. The reaction was cooled, diluted with CH$_2$Cl$_2$ and passed through an extrelut column to remove the water. The organic layer was concentrated and the residue purified by preparative LC/MS to give the title compound. MS calculated for C10H12ClNS+H 214, observed 214.

Example 16

6-Bromo-5-methyl-1,2,3,3a,7,7a-hexahydro-4-thia-2-aza-cyclopenta[α]pentalene

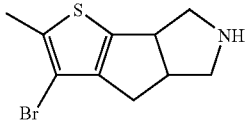

a.) 6-Bromo-5-methyl-3,3a,7,7a-tetrahydro-1H-4-thia-2-aza-cyclopenta[α]pentalene-2-carboxylic acid ethyl ester (Scheme 2)

The product of Example 15, step c) (69.1 mg, 0.30 mmol) was placed in a vial and diluted with CHCl$_3$ (740 μl) and AcOH (740 μl). Next, hydroquinone (~5 mg) was added followed by NBS (51.4 mg, 0.31 mmol) and the contents were heated to 40° C. for 6 hours. The crude reaction mixture was carefully poured into saturated NaHCO$_3$ (10 ml) and extracted with EtOAc (3×5 ml). The organic layer was dried (MgSO$_4$) and purified by preparative TLC using hexanes/EtOAc 50:50 providing the subtitled product. MS calculated for C13H16BrNO2S+H 330, observed 330, 332.

b.) 6-Bromo-5-methyl-1,2,3,3a,7,7a-hexahydro-4-thia-2-aza-cyclopenta[α]pentalene The product of step a) was treated with 40% aqueous KOH (1 ml) in EtOH (1 ml) at 105° C. for 16 hours. The reaction was cooled, diluted with CH$_2$Cl$_2$, and passed through an extrelut column to remove the water. The organic layer was concentrated and the residue purified by preparative LC/MS to give the subtitled compound. MS calculated for C10H12BrNS+H 258, observed 258, 260.

Example 17

5-Chloro-6-methyl-1,2,3,3a,7,7a-hexahydro-4-thia-2-aza-cyclopenta[α]pentalene

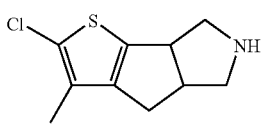

a.) 5-Amino-3,3a,7,7a-tetrahydro-1H-4-thia-2-aza-cyclopenta[α]pentalene-2,6-dicarboxylic acid diethyl ester (Scheme 1)

5-Oxo-hexahydro-cyclopenta[c]pyrrole-2-carboxylic acid ethyl ester (1.19 g, 6.03 mmol) was dissolved in DMF (30 ml) and treated with S$_8$ (193 mg, 6.03 mmol), ethylcyanoacetate (642 μl, 6.03 mmol) and piperidine (595 μl, 6.03 mmol). The contents were heated to 600C for 3 hours followed by dilution with brine (100 ml) and extraction with EtOAc (3×50 ml). The organic layer was dried (MgSO$_4$), concentrated and any residual DMF was removed by rotavap under high vacuum at 50° C. The crude residue was passed through a plug of silica gel using hexanes:EtOAc (50:50) providing the subtitled product (1.68 g, 86%). MS calculated for C15H20N2O4S+H 325, observed 325.

b.) 3,3a,7,7a-Tetrahydro-1H-4-thia-2-aza-cyclopenta[α]pentalene-2,6-dicarboxylic acid diethyl ester The product from step a) (1.68 g, 5.18 mmol) was dissolved in EtOH (26 ml) and treated with tert-butylnitrite (800 mg, 7.77 mmol) and Cu(OAc)$_2$ (1.41 g, 7.77 mmol) followed by heating at 600C for 1 hour. Next, the reaction mixture was cooled, diluted with EtOAc (150 ml) and extracted with water (100 ml). The organic layer was dried (MgSO$_4$) and concentrated providing a dark oily residue that was passed through a plug of silica gel using hexanes:EtOAc (50:50) to provide 601 mg (37%) of the subtitled product. MS calculated for C15H19NO4S+H 310, observed 310.

c.) 6-Hydroxymethyl-3,3a,7,7a-tetrahydro-1H-4-thia-2-aza-cyclopenta[α]pentalene-2-carboxylic acid ethyl ester The method of Example 15, step b) utilizing the product from step b) (601 mg, 1.94 mmol) gave the subtitle product (478 mg, 92%). MS calculated for C13H17NO3S+H 268, observed M—H$_2$O 250.

d.) 5-Chloro-6-hydroxymethyl-3,3a,7,7a-tetrahydro-1H-4-thia-2-aza-cyclopenta[α]pentalene-2-carboxylic acid ethyl ester The product of step c) (185 mg, 0.74 mmol) was dissolved in CHCl$_3$ (2.7 ml) and a solution of SO$_2$Cl$_2$ (59.5 μl, 0.74 mmol) in CHCl$_3$ (1 ml) was added dropwise over 10 minutes and the contents were stirred for 1 hour. Next, the mixture was diluted with CH$_2$Cl$_2$ (10 ml), washed with H$_2$O (2×25 ml), sat. NaHCO$_3$ (25 ml) and dried (MgSO$_4$). The crude residue was purified by preparative TLC (hexanes/EtOAc-1:3) to give the subtitle compound (99.7 mg, 45%). $^1$H NMR (300 MHz, CDCl$_3$, ppm) 1.20 (t, J=7 Hz, 3H); 2.37 (br s, 1H); 2.65-2.71 (m, 1H); 2.90-3.05 (m, 1H); 3.08-3.18 (br m, 1H); 3.28-3.42 (br m, 1H); 3.52-3.72 (br m, 2H); 3.75-3.88 (m, 2H); 4.09 (q, J=7 Hz, 2H); 4.54 (s, 2H).

e.) 5-Chloro-6-methyl-3,3a,7,7a-tetrahydro-1H-4-thia-2-aza-cyclopenta[α]pentalene-2-carboxylic acid ethyl ester Aluminum chloride (131.7 mg, 0.990 mmol) was added to a round bottom flask, cooled to 0° C. and diluted with anhydrous CH$_2$Cl$_2$ (3.3 ml). Next, tert-butylaminoborane (172 mg, 1.98 mmol) was added and the contents were stirred for 30 minutes. A solution of 5-Chloro-6-hydroxymethyl-3,3a,7,7a-tetrahydro-1H-4-thia-2-aza-cyclopenta[α]pentalene-2- carboxylic acid ethyl ester (99.7 mg, 0.33 mmol) in CH$_2$Cl$_2$ (330 μl) was added to the AlC13/t-butylaminoborane complex. The reaction mixture slowly warmed to room temperature and stirred for 16 hours. Next, the contents were carefully poured into 15% NaOH and extracted with CH$_2$Cl$_2$ (2×50 ml). The organic layer was dried (MgSO$_4$), solvent evaporated in vacuo, and the residue purified by preparative TLC (hexanes:EtOAc-7:3) to give the subtitle compound. MS calculated for C13H16ClNO2S+H 286, observed 286.

f.) 5-Chloro-6-methyl-1,2,3,3a,7,7a-hexahydro-4-thia-2-aza-cyclopenta[α]pentalene The title compound was prepared by the method of Example 16, step b) using the the product from step e). $^1$H NMR (300 MHz, CD$_3$OD, ppm) 2.07 (s, 3H); 2.62-2.70 (m, 1H); 3.20-3.12 (m, 1H); 3.13-3.21 (m, 1H); 3.35-3.43 (m, 2H); 3.45-3.58 (m, 2H); 3.60-3.68 (m, 1H); 4.08-4.18 (br m, 1H); MS calculated for C10H12ClNS+H 214, observed 214.

Example 18

5-Bromo-6-methyl-1,2,3,3a,7,7a-hexahydro-4-thia-2-aza-cyclopenta[α]pentalene

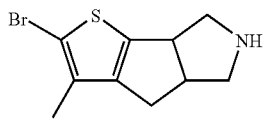

a.) 5-Bromo-6-hydroxymethyl-3,3a,7,7a-tetrahydro-1H-4-thia-2-aza-cyclopenta[α]pentalene-2-carboxylic acid ethyl ester (Scheme 1)

To a solution of the product from Example 17, step c) (199 mg, 0.79 mmol) in CHCl$_3$ (3 ml) and AcOH (3 ml) was added NBS (156 mg, 0.88 mmol). The reaction mixture was stirred for 30 minutes, quenched with saturated NaHCO$_3$ (10 ml), and extracted with EtOAc (20 ml). The EtOAc layer was dried (MgSO$_4$), filtered, and solvent evaporated in vacuo to give the crude product that was purified by silica-gel preparative TLC (hexanes:EtOAc-3:1) providing the subtitle compound (99.6 mg, 36%). $^1$H NMR (300 MHz, CDCl$_3$, ppm) 1.22 (t, J=7 Hz, 3H); 2.42 (br s, 1H); 2.63-2.78 (m, 1H); 2.95-3.18 (m, 2H); 3.30-3.48 (br m, 1H); 3.50-3.72 (br m, 2H); 3.75-3.88 (br m, 2H); 4.08 (q, J=7 Hz, 2H); 4.52 (s, 2H).

b.) 5-Bromo-6-methyl-3,3a,7,7a-tetrahydro-1H-4-thia-2-aza-cyclopenta[α]pentalene-2-carboxylic acid ethyl ester The subtitle compound was prepared by the method of Example 17, step e) using the product from step a) (99.6 mg, 0.29 mmol). MS calculated for C13H16BrNO2S+H 330, observed 330, 332.

c.) 5-Bromo-6-methyl-1,2,3,3a,7,7a-hexahydro-4-thia-2-aza-cyclopenta[α]pentalene The subtitle compound was prepared by the method of Example 16, step b) using the product from step b). $^1$H NMR (300 MHz, CD$_3$OD, ppm) 2.07 (s, 3H); 2.59-2.71 (m, 1H); 3.01-3.20 (m, 3H); 3.45-3.71 (m, 3H); 4.05-4.18 (br m, 1H); MS calculated for C10H12BrNS+H 258, observed 258, 260.

Example 19

5,6-Dibromo-1,2,3,3a,7,7a-hexahydro-4-thia-2-aza-cyclopenta[α]pentalene

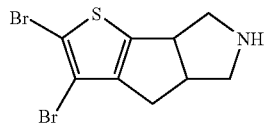

a.) cis-3-(4,5-Dibromo-thiophen-2-yl)-acrylic acid tert-butyl ester (Scheme 3)

(Diphenoxy-phosphoryl)-acetic acid tert-butyl ester (8.49 g, 24.4 mmol) was dissolved in THF (519 ml) and cooled to −78° C. followed by the addition of triton B (13.3 ml, 40% by wt. in MeOH). After 15 minutes a solution of 4,5-Dibromo-thiophene-2-carbaldehyde (7.0 g, 25.9 mmol) in THF (20 ml) was added and the reaction was stirred for 1 hour. Next, the reaction mixture was quenched with sat. NH$_4$Cl (250 ml), diluted with H$_2$O (500 ml), and extracted with EtOAc (2×300 ml). The organic layers were washed with water (2×200 ml), brine (100 ml), and dried (MgSO$_4$). The crude was passed through a plug of silica gel with EtOAc providing the desired product 9.2 g (96%) as a 4:1 mixture of cis:trans. MS calculated for C$_{10}$H$_{12}$BrNS−H 367, observed M-tBu 309, 311, 313.

b.) 1-Benzyl-4-(4,5-dibromo-thiophen-2-yl)-pyrrolidine-3-carboxylic acid tert-butyl ester The product of step a) was dissolved in CH$_2$Cl$_2$ (41 ml) and benzyl-methoxymethyl-trimethylsilanylmethyl-amine (2.32 g, 9.78 mmol) was added and the mixture was cooled to 0° C. Finally, trifluoroacetic acid (10 mol %, 92.9 mg, 0.81 mmol) was added and the reaction mixture was warmed to 22° C. and stirred for 16 hours. The reaction was washed with sat. NaHCO$_3$ (10 ml), brine (10 ml) and dried (MgSO$_4$). The crude was purified by silica-gel chromatography using a gradient of ethyl acetate/hexanes (0% to 25% ethyl acetate) to give the subtitle product (2.6 g, 64%).

c.) 1-Benzyl-4-(4,5-dibromo-thiophen-2-yl)-pyrrolidine-3-carboxylic acid trifluoroacetate The product of step b) (2.6 g, 5.2 mmol) in CH$_2$Cl$_2$ (25 ml) and trifluoroacetic acid (TFA) (75 ml) was stirred at 220C for 16 hours. Next, the solvent was evaporated and toluene (50 ml) was added and subsequently evaporated in vacuo at 40° C. to remove residual TFA. The crude subtitle product was used without further purification.

d.) 1-Benzyl-4-(4,5-dibromo-thiophen-2-yl)-pyrrolidine-3-carbonyl chloride hydrochloride The product from step c) (2.3 g, 5.18 mmol) in CH$_2$Cl$_2$ (26 ml) was treated with oxalyl chloride (2.3 ml, 26.3 mmol) followed by DMF (4 drops) and the mixture was stirred for 1 hour at 22° C. The solvent was evaporated in vacuo to give the crude subtitle compound as pink solid that was used without further purification.

e.) 2-Benzyl-5,6-dibromo-2,3,3a,7a-tetrahydro-1H-4-thia-2-aza-cyclopenta[α]pentalen-7-one A slurry of AlCl₃ (2.38 g, 18 mmol) in CH₂Cl₂ (21 ml) was cooled to 0° C. under N₂. Next, a solution of the product from step d) (3.0 g, 6 mmol) in CH₂Cl₂ (9 ml) was added dropwise over 5 minutes and the reaction mixture was stirred for an additional 45 minutes at 0° C. The reaction was poured into ice cold 2M NaOH (100 ml) and extracted with CH₂Cl₂ (2×100 ml). The organic layer was dried (MgSO₄), evaporated, and purified by silica-gel chromatography using a gradient of 0-50% ethyl acetate in hexane to give the subtitle product (696 mg, 27%). ¹H NMR (300 MHz, CDCl₃, ppm) 2.39-2.49 (m, 2H); 2.92 (br d, J=9 Hz, 1H); 3.24 (br d, J=9 Hz, 1H); 3.34-3.40 (m, 1H); 3.54 (d, J=13 Hz, 1H); 3.60 (d, 13 Hz, 1H); 3.76-3.81 (m, 1H); 7.13-7.32 (m, 5H); MS calculated for C16H13Br2NOS+H 428, observed 426, 428, 430.

f.) 2-Benzyl-5,6-dibromo-1,2,3,3a,7,7a-hexahydro-4-thia-2-aza-cyclopenta[α]pentalen-7-ol The product of step e) (325 mg, 0.76 mmol) was dissolved in MeOH (10 ml) and treated with NaBH₄ (289 mg, 7.6 mmol) at 0° C. Next, the reaction was warmed to 22° C. and, after 2 hours, AcOH was added dropwise until gas evolution ceased. The quenched reaction mixture was slowly poured saturated NaHCO₃ (100 ml). The aqueous mixture was extracted with EtOAc (2×50 ml), dried (MgSO₄) and concentrated providing the subtitle product (298 mg, 91%). MS calculated for C16H15Br2NOS+H 430, observed 428, 430, 432.

g.) 2-Benzyl-5,6-dibromo-1,2,3,3a,7,7a-hexahydro-4-thia-2-aza-cyclopenta[α]pentalene The product from step f) (300 mg, 0.69 mmol) in dichloroethane (2.6 ml) was treated with InCl₃ (153 mg, 0.69 mmol) and chlorodiphenylsilane (457 mg, 2.08 mmol). The contents were heated to 60° C. for 16 hours. The reaction mixture was cooled to 22° C., poured into sat. NaHCO₃ and diluted with EtOAc (75 ml); producing a white emulsion. The emulsion was passed through celite and the organic layer was separated, washed with brine (25 ml) and dried (MgSO₄). The crude product was dissolved in 7:3 hexanes:EtOAc and passed through a plug of silica gel to give the subtitle compound. MS calculated for C16H15Br2NS+H 414, observed 412, 414, 416.

h.) 5,6-Dibromo-1,2,3,3a,7,7a-hexahydro-4-thia-2-aza-cyclopenta[α]pentalene

The product from step g) (605 mg, 1.46 mmol) in dichloroethane (7 ml) was treated with powdered K₂CO₃ (806 mg, 5.84 mmol) and 1-chloroethyl chloroformate (Ace-Cl) (632 µl, 5.84 mmol) at 80° C. for 16 hours. Next, the reaction was cooled, filtered and concentrated providing an oily residue. This oily residue was diluted with anhydrous MeOH (15 ml) and stirred for 1 hour at 22° C. The solvent was concentrated and the crude residue was purified by preparative LC/MS providing title compound. ¹H NMR (300 MHz, CD₃OD, ppm) 2.65-2.75 (m, 1H); 3.05-3.30 (m, 2H); 3.32-3.80 (m, 4H); 4.10-4.28 (br m, 1H); MS calculated for C9H9Br2NS+H 324, observed 322, 324, 326.

Example 20

6-Methoxy-1,2,3,3a,7,7a-hexahydro-4-thia-2-aza-cyclopenta[α]pentalene

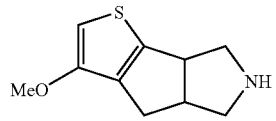

a.) 5,6-Dibromo-3,3a,7,7a-tetrahydro-1H-4-thia-2-aza-cyclopenta[α]pentalene-2-carboxylic acid ethyl ester (Scheme 3)

The subtitle compound was prepared by the method of Example 15, step a) using the product from Example 19, step h) (378 mg, 1.05 mmol) to give 87.7 mg (21%) of the product. MS calculated for C12H13Br2NO2S+H 396, observed 394, 396, 398.

b.) 6-Bromo-3,3a,7,7a-tetrahydro-1H-4-thia-2-aza-cyclopenta[α]pentalene-2-carboxylic acid ethyl ester The product of step a) (87.7 mg, 0.223 mmol) in AcOH (244 µl) and H₂O (244 µl) was treated with Zn dust (29 mg, 0.45 mmol) at 105° C. for 1 hour. The contents were cooled, poured into sat. NaHCO₃ (5 ml) and extracted with EtOAc (3×3 ml). The organic layer was dried (MgSO₄) and concentrated to give the subtitle compound that was used without further purification.

c.) 6-Methoxy-1,2,3,3a,7,7a-hexahydro-4-thia-2-aza-cyclopenta[α]pentalene

The product of step b) (57.8 mg, 0.183 mmol) in MeOH (51 µl) was treated with CuO (7 mg, 0.09 mmol), a 25% solution of sodium methoxide in MeOH (129 µl) and tetra-butylammonium iodide (TBAI) (10 mg) at 100° C. for 12 hours. The reaction mixture was cooled and purified by preparative LC/MS to give the title compound. ¹H NMR (300 MHz, CDCl₃, ppm) 2.40-2.60 (m, 1H); 2.82-3.01 (m, 2H); 3.05-3.63 (br m, 4H); 3.77 (s, 3H); 3.81-3.98 (br s, 1H); 6.17 (s, 1H); MS calculated for C10H13NOS+H 196, observed 196.

Example 21

2-Bromo-3b,4,5,6,6a,7-hexahydro-1-thia-5-aza-cyclopenta[α]pentalene

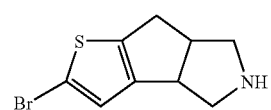

a.) 4-(2-Ethoxythiocarbonylsulfanyl-1-hydroxy-ethyl)-5-oxo-hexahydro-cyclopenta-[c]pyrrole-2-carboxylic acid ethyl ester (Scheme 4)

A 1M solution of Lithium bis(trimethylsilyl)amide in THF (LHMDS) (6.08 ml, 6.08 mmol) was added to anhydrous THF (4 ml) and the mixture was cooled to −30° C. under N₂. Next, a solution of 5-Oxo-hexahydro-cyclopenta[c]pyrrole-2-carboxylic acid ethyl ester (1.0 g, 5.07 mmol) in THF (10 ml) was added dropwise over 15 minutes and the mixture was stirred for an additional 15 minutes. Next, a 0.5M solution of ZnCl₂ (15.2 ml, 7.6 mmol) was added over 15 minutes and the reaction mixture was stirred for an additional 30 minutes. The reaction temperature was lowered to −70° C. and a solution of dithiocarbonic acid O-ethyl ester S-(2-oxo-ethyl) ester (913 mg, 5.57 mmol) in THF (1 ml) was added dropwise over 25-30 minutes. After 3 hours at −70° C., a solution of acetic acid (2.5 ml) in toluene (7.5 ml) was added and the reaction mixture was warmed to 0° C. The reaction mixture was diluted with H₂O (7.5 ml) and the organic layer separated, dried (MgSO₄), and concentrated providing oily brown residue that was purified by silica-gel chromatography using a ethyl acetate/hexanes gradient (0% ethyl acetate to 100% ethyl acetate) to give the subtitle product as an oil (756 mg, 41%).

b.) 3b,6,6a,7-Tetrahydro-4H-1-thia-5-aza-cyclopenta[α]pentalene-5-carboxylic acid ethyl ester Deoxygenated (N₂ sparge for 15 minutes) N-methylpiperazine (3.5 ml) was placed in a 25 ml flask and cooled to 0° C. Next, a solution of the product from step a) (756 mg, 2.09 mmol) in CH₂Cl₂ (1.05 ml) was added dropwise over 30 minutes. After 3 hours at 0° C., 12M HCl (10 ml) was added dropwise to pH 1-2. The reaction was warmed to 22° C. and stirred for 1 hour. The reaction mixture was diluted with H₂O (30 ml) and extracted with CH₂Cl₂ (3×20 ml). The combined organic layers were dried (MgSO₄) and the crude oil was purified by silica-gel chromatography (hexanes:EtOAc-7:3) providing the subtitle product as a clear oil (203 mg, 41%). MS calculated for C12H15NO2S+H 238, observed 238.

c.) 2-Bromo-3b,6,6a,7-tetrahydro-4H-1-thia-5-aza-cyclopenta[α]pentalene-5-carboxylic acid ethyl ester The product of step b) (25.3 mg, 0.11 mmol) was treated by the method of Example 18, step a) to give 20.9 mg (62%) of the crude subtitle compound that was used in the next step without purification. MS calculated for C12H14BrNO2S+H 316, observed 316, 318.

d.) 2-Bromo-3b,4,5,6,6a,7-hexahydro-1-thia-5-aza-cyclopenta[α]pentalene

The product of step c) (20.9 mg, 0.07 mmol) in CH₂Cl₂ (330 µl) was treated with iodotrimethylsilane (19.8 mg, 0.099 mmol) at 50° C. for 16 hours. The solvent was evaporated in vacuo leaving a brown residue that was dissolved in MeOH and a portion purified by preparative LC/MS to give the title compound. ¹H NMR (300 MHz, CDCl₃, ppm) 2.76-2.81 (m, 1H); 2.95-3.03 (m, 1H); 3.12-3.22 (m, 2H); 3.44-3.61 (m, 3H); 3.81-3.85 (m, 1H); 6.78 (s, 1H); 9.20-9.4 (br s, 2H); MS calculated for C9H10BrNS+H 244, observed 244, 246.

Example 22

2,3-Dibromo-3b,4,5,6,6a,7-hexahydro-1-thia-5-aza-cyclopenta[α]pentalene

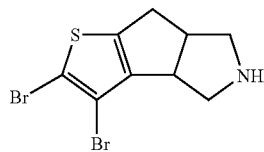

a.) 23-Dibromo-3b,6,6a,7-tetrahydro-4H-1-thia-5-aza-cyclopenta[α]pentalene-5-carboxylic acid ethyl ester (Scheme 4)

A solution of the product from Example 21, step b) (25.6 mg, 0.11 mmol) in cyclohexane (540 µl) was treated with NaHCO₃ (54.4 mg, 0.65 mmol) and Br₂ (16.6 µl, 0.324 mmol). After 30 minutes, the reaction was quenched with a 10% solution of NaSO₃ (500 µl) and diluted with EtOAc (4 ml). The EtOAc layer was dried (MgSO₄) and concentrated giving the subtitle product that was used without further purification. MS calculated for C12H13Br2NO2S+H 394, observed 392, 394, 396.

b.) 2,3-Dibromo-3b, 4,5,6,6a,7-hexahydro-1-thia-5-aza-cyclopenta[α]pentalene

The title compound was prepared by the method of Example 21, step d) using the product from step a) (10.5 mg, 0.03 mmol). ¹H NMR (300 MHz, CDCl₃, ppm) 2.70-2.78 (m, 1H); 2.82-2.94 (m, 1H); 3.15-3.28 (m, 3H); 3.41-3.55 (m, 2H); 3.65-3.78 (m, 1H); MS calculated for C9H9Br2NS+H 324, observed 322, 324, 326.

Example 23

3-Trifluoromethyl-3b,4,5,6,6a,7-hexahydro-1-thia-5-aza-cyclopenta[α]pentalene

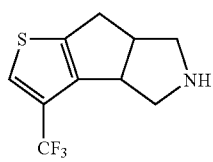

a.) 4-(1-Ethoxythiocarbonylsulfanylmethyl-2,2,2-trifluoro-1-hydroxy-ethyl)-5-oxo-hexahydro-cyclopenta[c]pyrrole-2-carboxylic acid ethyl ester (Scheme 4)

A 1M solution of Lithium bis(trimethylsilyl)amide in THF (LHMDS) (6.10 ml, 6.10 mmol) was added to anhydrous THF (4 ml) and the mixture was cooled to −30° C. under N₂. Next, a solution of 5-Oxo-hexahydro-cyclopenta[c]pyrrole-2-carboxylic acid ethyl ester (1.0 g, 5.07 mmol) in THF (1 ml) was added dropwise over 15 minutes and the mixture was stirred for an additional 15 minutes. Next, a 0.5M solution of ZnCl₂ (15.2 ml, 7.6 mmol) was added over 15 minutes and the reaction mixture was stirred for an additional 30 minutes. The reaction temperature was lowered to −70° C. and a solution of dithiocarbonic acid O-ethyl ester S-(3,3,3-trifluoro-2-oxo-propyl) ester (1.3 g, 5.59 mmol) in THF (1 ml) was added dropwise over 25-30 minutes. After 3 hours at −70OC, a solution of acetic acid (2.5 ml) in toluene (7.5 ml) was added and the reaction mixture was warmed to 0° C. The reaction mixture was diluted with H$_2$O (7.5 ml) and the organic layer separated, dried (MgSO$_4$), and concentrated providing a oily brown residue that was purified by silica-gel chromatography using a gradient of ethyl acetate/hexanes (0% to 100% ethyl acetate) to give the subtitle product as an oil (533 mg, 24%).

b.) 3-Trifluoromethyl-3b,6,6a,7-tetrahydro-4H-1-thia-5-aza-cyclopenta[α]pentalene-5-carboxylic acid ethyl ester Deoxygenated (N$_2$ sparge for 15 min) N-methylpiperazine (1.3 ml) was placed in a 5 dram vial and cooled to 0° C. Next, a solution of 4-(1-Ethoxythiocarbonylsulfanyl-methyl-2,2,2-trifluoro-1-hydroxy-ethyl)-5-oxo-hexahydro-cyclopenta[c]pyrrole-2-carboxylic acid ethyl ester (44 mg, 0.10 mmol) in CH$_2$Cl$_2$ (400 μl) was added dropwise over 15 minutes. After 3 hours, at 0° C., 12M HCl (10 ml) was added dropwise until pH 1-2 had been reached. The reaction was warmed to 22° C. and stirred for 1 hour. The reaction mixture was extracted with CH$_2$Cl$_2$ (3×20 ml) and H$_2$O (30 ml). The organic layer was dried (MgSO$_4$) and the crude oil was purified by flash chromatography (hexanes:EtOAc-7:3) providing the subtitle product as a clear oil (13.5 mg, 43%). $^1$H NMR (300 MHz, CDCl$_3$, ppm) 1.24 (t, J=7 Hz, 3H); 2.78 (br d, J=16 Hz, 1H); 3.14 (dd, J$_1$=16 Hz, J$_2$=8 Hz, 1H); 3.20-3.38 (br m, 1H); 3.48-3.62 (br m, 2H); 3.63-3.88 (m, 3H); 4.11 (q, J=7 Hz, 2H); 7.59 (s, 1H).

c.) 3-Trifluoromethyl-3b,4,5,6,6a,7-hexahydro-1-thia-5-aza-cyclopenta[α]pentalene The title compound was prepared by the method of Example 21, step d) using the product from step b) to give 7.3 mg (61%) of product. MS calculated for C10H10F3NS+H 234, observed 234.

Example 24

2-Chloro-7-methyl-3b,4,5,6,6a,7-hexahydro-1-thia-5-aza-cyclopenta[α]pentalene

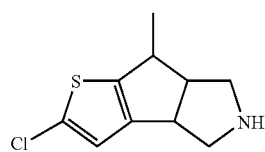

a.) 2-Chloro-7-methyl-3b,6,6a,7-tetrahydro-4H-1-thia-5-aza-cyclopenta[α]pentalene-5-carboxylic acid tert-butyl ester (Scheme 3)

A solution of the product from Example 35, step a) (51.9 mg, 0.186 mmol) in AcOH (420 μl) and CHCl$_3$ (420 μl) was treated with NCS (25.2 mg, 0.189 mmol) at 22OC for 16 hours. The reaction was carefully poured into sat. NaHCO$_3$ (25 ml) and extracted with EtOAc (2×25 ml). The combined organic layers were dried (MgSO$_4$) and the solvent evaporated leaving a residue that was purified by preparative TLC using 1:1 hexanes:EtOAc to give 32.9 mg (56%) of the subtitle compound.

b.) 2-Chloro-7-methyl-3b,4,5,6,6a,7-hexahydro-1-thia-5-aza-cyclopenta[α]pentalene The product of step a) (16 mg, 0.05 mmol) was treated by the method of Example 35, step c to give the title compound. $^1$H NMR (300 MHz, CDCl$_3$, ppm) 1.27 (d, J=7 Hz, 3H); 2.99-3.13 (m, 3H); 3.29-3.41 (m, 2H); 3.47-3.57 (m, 1H); 3.68-3.78 (m, 1H); 6.60 (s, 1H); 6.89 (br s, 1H); MS calculated for C10H12ClNS+H 214, observed 214.

Example 25

2-Iodo-7-methyl-3b,4,5,6,6a,7-hexahydro-1-thia-5-aza-cyclopenta[α]pentalene

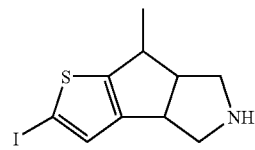

a.) 2-Iodo-7-methyl-3b,6,6a,7-tetrahydro-4H-1-thia-5-aza-cyclopenta[α]pentalene-5-carboxylic acid tert-butyl ester (Scheme 3)

A solution of the product from Example 35, step a) (49.3 mg, 0.176 mmol) in AcOH (420 μl) and CHCl$_3$ (420 μl) was treated with NIS (40.3 mg, 0.179 mmol) at 22° C. for 2 hours. The reaction was carefully poured into sat. NaHCO$_3$ (25 ml) and extracted with EtOAc (2×25 ml). The combined organic layers were dried (MgSO$_4$) and solvent evaporated in vacuo to give a residue that was purified by preparative TLC using 1:1 hexanes:EtOAc to give 51.9 mg (73%) of the subtitle compound.

b.) 2-Iodo-7-methyl-3b,4,5,6,6a,7-hexahydro-1-thia-5-aza-cyclopenta[α]pentalene

The product from step a) (17.8 mg, 0.04 mmol) was treated by the method of Example 35, step c) to give the title compound. $^1$H NMR (300 MHz, CDCl$_3$, ppm) 1.28 (d, J=7 Hz, 3H); 3.02-3.11 (m, 3H); 3.22-3.32 (m, 1H); 3.34-3.45 (m, 1H); 3.48-3.58 (m, 1H); 3.51-3.78 (m, 1H); 5.95 (br s, 1H); 6.90 (s, 1H); MS calculated for C10H12INS+H 306, observed 306.

Example 26

5-Chloro-6,7-dimethyl-1,2,3,3a,7,7a-hexahydro-4-thia-2-aza-cyclopenta[α]pentalene

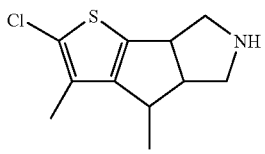

a.) 3-(4-Bromo-thiophen-2-yl)-acrylic acid methyl ester (Scheme 3)

[Bis-(2,2,2-trifluoro-ethoxy)-phosphoryl]-acetic acid methyl ester (9.25 g, 29.1 mmol) was dissolved in THF (400 ml) and 18-C-6 (13.9 g, 52.4 mmol) was added and the mixture was cooled to −78° C. Next, KHMDS (5.73 g, 28.8 mmol) was added and the reaction mixture was stirred for 30 minutes, after which 4-bromothiophene-2-carboxaldehyde (5.0 g, 26.2 mmol) was added and the reaction was stirred for an additional 3 hours. Saturated $NH_4Cl$ (100 ml) was added and the reaction was warmed to 22° C. The mixture was diluted with EtOAc (700 ml) and $H_2O$ (400 ml). The organic layer was washed 10% HCl (100 ml), brine (100 ml), and dried ($MgSO_4$). The solvent was evaporated in vacuo and the crude residue was purified by silica-gel chromatography (hexanes:EtOAc-10:1) providing 5.6 g (87%) of the subtitle product.

b.) 1-Benzyl-4-(4-bromo-thiophen-2-yl)-pyrrolidine-3-carboxylic acid methyl ester The product from step a) (3.9 g, 15.8 mmol) was treated by the method of Example 19, step b) to give 4.33 g (72%) of the subtitle compound.

c.) 1-Benzyl-4-(4-bromo-thiophen-2-yl)-pyrrolidine-3-carboxylic acid

The product of step b) (4.3 g, 11.3 mmol) was dissolved in 6M HCl and stirred at 85° C. for 16 hours. Next, the solvent was evaporated in vacuo providing the subtitle compound that was used without further purification. MS calculated for C16H16BrNO2S−H 364, observed 364, 366.

d.) 1-Benzyl-4-(4-bromo-thiophen-2-yl)-pyrrolidine-3-carbonyl chloride

A solution of the product from step c) (4.6 g, 12.6 mmol) in $CH_2Cl_2$ (63 ml) was treated with DMF (3-5 drops) and oxalyl chloride (2.4 g, 18.9 mmol) for 2 hours. Next, the solvent was evaporated in vacuo to give 4.04 g (100%) of the subtitle compound that was used without further purification.

e.) 2-Benzyl-6-bromo-Z3,3a,7a-tetrahydro-1H-4-thia-2-aza-cyclopenta[α]pentalen-7-one A solution of the product from step d) (4.04 g, 9.59 mmol) in $CH_2Cl_2$ (13.7 ml) was added dropwise to a slurry of $AlCl_3$ (3.83 g, 28.77 mmol) in $CH_2Cl_2$ (36 ml) at 22° C. After 45 minutes, the reaction mixture was poured into ice cold 2 M NaOH (100 ml) and extracted with $CH_2Cl_2$ (300 ml). The organic layer was dried ($MgSO_4$) and solvent evaporated in vacuo to give a residue that was purified by silica-gel chromatography using a ethyl acetate/hexanes gradient (0% to 50% ethyl acetate) to give the subtitle compound (2.4 g, 72%). MS calculated for C16H14BrNOS+H 348, observed 348, 350.

f.) 2-Benzyl-6-methyl-Z 3,3a,7a-tetrahydro-1H-4-thia-2-aza-cyclopen[α]pentalen-7-one A solution of the product from step e) (2.4 g, 6.89 mmol) in dioxane (34.5 ml) was treated with $Pd(dppf)_2Cl_2$ (337 mg, 0.41 mmol) and a 2M solution of dimethylzinc in toluene (6.89 ml, 13.78 mmol) at 102° C. for 1 hour. The reaction was cooled to 22° C. and carefully quenched with sat. $NH_4Cl$ (20 ml). After the effervescence subsided, the reaction was extracted with EtOAc (3×50 ml). The combined organic layers were dried ($MgSO_4$) and passed through a plug of silica-gel using 50:50 hexanes:EtOAc to give the subtitle compound (1.9 g, 97%). MS calculated for C17H17NOS+H 284, observed 284.

g.) 2-Benzyl-6-methyl-7-methylene-1,2Z3,3a,7,7a-hexahydro-4-thia-2-aza-cyclopenta[α]pentalene Methyltriphenylphosphonium bromide (9.6 g, 26.8 mmol) was dissolved in THF (67 ml), cooled to 0° C. and treated with potassium bis(trimethylsilyl)amide (KHMDS) (5.33 g, 26.8 mmol) producing a clear yellow solution. Next, a solution of the product from step f) (1.9 g mg, 6.70 mmol) in THF (33 ml) was added and the reaction was warmed to 22° C. After 1 hour, the reaction was diluted with $CH_2Cl_2$ (300 ml) and washed with brine (100 ml). The organic layer was dried ($MgSO_4$) and the solvent evaporated in vacuo to give the crude subtitle product (3.1 g) that was used without further purification.

h.) 2-Benzyl-6,7-dimethyl-1,2,3,3a,7,7a-hexahydro-4-thia-2-aza-cyclopenta[α]pentalene A solution of product from step g) (3.1 g) in MeOH (55 ml) was treated with 10% Pd/C (4.65 g) and a balloon of $H_2$ at 40° C. for 16 hours. The reaction mixture was filtered through a pad of celite, evaporated in vacuo and the residue purified by silica-gel chromatography using a ethyl acetate/hexanes gradient (0% to 50% ethyl acetate) to give 948 mg (49% over two steps) of the subtitle product. MS calculated for C18H21NS+H 284, observed 284.

i.) 6,7-Dimethyl-1,2,3,3a,7,7a-hexahydro-4-thia-2-aza-cyclopenta[α]pentalene

The product of step h) (948 mg, 3.35 mmol) in dichloroethane (17 ml) was treated with $K_2CO_3$ (1.85 g, 13.4 mmol) and Ace-Cl (1.45 ml, 13.4 mmol) at 80° C. for 16 hours. Next, the reaction mixture was filtered, concentrated and the residue was dissolved in anhydrous MeOH (25 ml) and stirred for 1 hour at 22° C. The MeOH was concentrated and triturated with ether producing 733 mg (95%) of the subtitle compound. $^1$H NMR (300 MHz, $d_6$-DMSO, ppm) 1.27 (d, J=7 Hz, 3H); 2.97-3.10 (m, 1H); 3.19-3.38 (m, 2H); 3.42-3.62 (m, 3H); 3.78-3.88 (m, 1H); 6.92 (d, J=5 Hz, 1H); 7.47 (d, J=5 Hz, 1H); 9.05 (br s, 1H); 9.38 (br s, 1H); MS calculated for C11H15NS+H 194, observed 194.

j.) 6,7-Dimethyl-3,3a,7,7a-tetrahydro-1H-4-thia-2-aza-cyclopenta[α]pentalene-2-carboxylic acid ethyl ester A solution of the product from step i) (733 mg) was treated by the method of Example 15, step a) to give 654 mg (77%) of the subtitle compound. MS calculated for C14H19NO2S+H 266, observed 266.

k.) 5-Chloro-6,7-dimethyl-3,3a,7,7a-tetrahydro-1H-4-thia-2-aza-cyclopenta[α]pentalene-2-carboxylic acid ethyl ester The product from step j) (316 mg, 1.19 mmol) was dissolved in $CHCl_3$ (6 ml) and a solution of $SO_2Cl_2$ (95.6 μl, 1.19 mmol) in $CHCl_3$ (1.6 ml) was added dropwise over 10 minutes. and the contents were stirred for 1 hour. Next, the mixture was diluted with $CH_2Cl_2$ (50 ml), washed with $H_2O$ (2×50 ml), sat. $NaHCO_3$ (50 ml) and dried ($MgSO_4$). The solvent was evaporated in vacuo and the crude product was purified by silica-gel chromatography (hexanes:EtOAc-1:3) to give the subtitle compound. MS calculated for C14H18ClNO2S+H 300, observed 300.

1.) 5-Chloro-6,7-dimethyl-1,2,3,3a,7,7a-hexahydro-4-thia-2-aza-cyclopenta[α]pentalene The product from step k) was treated by the method of Example 16, step b) to give the title compound. $^1$H NMR (300 MHz, d$_6$-DMSO, ppm) 1.25 (d, J=7 Hz, 3H); 3.02-3.19 (m, 2H); 3.22-3.32 (m, 1H); 3.35 (s, 3H); 3.42-3.58 (m, 3H); 3.84-3.94 (m, 1H); 9.30 (br s, 2H); MS calculated for C11H14ClNS+H 228, observed 228.

Example 27

6-Bromo-5,7-dimethyl-1,2,3,3a,7,7a-hexahydro-4-thia-2-aza-cyclopenta[α]pentalene

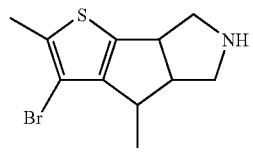

a.) 3-Thiophen-2-yl-acrylic acid methyl ester (Scheme 3)

Thiophene-2-carbaldehyde (4.0 g, 35.7 mmol) was treated by the method outlined in Example 26, step a) to afford the subtitle product (4.5 g, 75%). MS calculated for C$_8$H$_8$O$_2$S+H: 169, observed: 169.

b.) 1-Benzyl-4-thiophen-2-yl-pyrrolidine-3-carboxylic acid methyl ester

The product from step a) (4.5 g, 26.8 mmol) was treated by the method outlined in Example 19, step b) to afford the subtitle compound (5.85 g, 73%). MS calculated for C$_{17}$H$_{19}$NO$_2$S+H: 302, observed: 302.

c.) 1-Benzyl-4-thiophen-2-yl-pyrrolidine-3-carboxylic acid

The product from step b) (5.85 g, 19 mmol) was treated by the method outlined in Example 26, step c) to afford the subtitle compound (6.7 g, 100%). MS calculated for C$_{16}$H$_{17}$NO$_2$S+H: 288, observed: 288.

d.) 1-Benzyl-4-thiophen-2-yl-pyrrolidine-3-carbonyl chloride

The product from step c) (6.7 g, 20.8 mmol) was treated by the method outlined in Example 26, Step d) to afford the subtitle compound (6.09 g, 86%).

e.) 2-Benzyl-Z23,3a,7a-tetrahydro-1H-4-thia-2-aza-cyclopenta[α]pentalen-7-one The product from step d) (6.09 g, 17.9 mmol) was treated by the method outlined in Example 26, Step e) to afford the subtitle compound (1.92 g, 40%). MS calculated for C$_{16}$H$_{15}$NOS+H: 284, observed: 284.

f.) 2-Benzyl-7-methylene-1,2,3,3a,7,7a-hexahydro-4-thia-2-aza-cyclopenta[α]pentalene The product from step e) (822 mg, 3.06 mmol) was treated by the method outlined in Example 26, Step g) to afford the subtitle compound. MS calculated for C$_{17}$H$_{17}$NS+H: 268, observed: 268.

g.) 2-Benzyl-7-methyl-1,2,3,3a,7,7a-hexahydro-4-thia-2-aza-cyclopenta[α]pentalene The product from step f) (905 mg, 3.39 mmol) was treated by the method outlined in Example 26, step h) to afford the subtitle compound (410 mg, 45%). MS calculated for C$_{17}$H$_{19}$NS+H: 270, observed: 270.

h.) 7-Methyl-1,2Z3,3a,7,7a-hexahydro-4-thia-2-aza-cyclopenta[α]pentalene

The product from step g) (410 mg, 1.52 mmol) was treated by the method outlined in Example 26, Step i) to afford the subtitle compound (258 mg, 95%). MS calculated for C$_{10}$H$_{13}$NS+H: 180, observed: 180.

i.) 7-Methyl-3,3a,7,7a-tetrahydro-1H-4-thia-2-aza-cyclopenta[α]pentalene-2-carboxylic acid ethyl ester A 0° C. solution of the product from step h) (258 mg, 1.19 mmol) in CH$_2$Cl$_2$ (6 ml) was treated with triethylamine (497 µl, 3.57 mmol) and ethyl chloroformate (227 µl, 2.38 mmol) and the reaction was warmed to 22° C. Next, the reaction mixture was extracted with CH$_2$Cl$_2$ (50 ml) and brine (25 ml). The combined organic layers were dried (MgSO$_4$) and the crude product was purified by silica-gel chromatography (hexanes:EtOAc-50:50) to give the subtitle compound (204 mg, 68%). MS calculated for C13H17NO2S+H 252, observed 252.

j.) 5-Bromo-7-methyl-3,3a,7,7a-tetrahydro-1H-4-thia-2-aza-cyclopenta[α]pentalene-2-carboxylic acid ethyl ester A solution of the product from step i) (204 mg, 0.81 mmol) in AcOH (2 ml) and CHCl$_3$ (2 ml) was treated with NBS (152 mg, 0.85 mmol) at 22° C. for 30 minutes. Next, the reaction was carefully quenched with sat. NaHCO$_3$ (10 ml), extracted with EtOAc (2×75 ml) and the combined organic layers were dried (MgSO$_4$). The crude product was filtered through a plug of silica gel using hexanes:EtOAc (50:50) to give the subtitle compound. MS calculated for C13H16BrNO2S+H 330, observed 332.

k.) 5,7-Dimethyl-3,3a,7,7a-tetrahydro-1H-4-thia-2-aza-cyclopenta[α]pentalene-2-carboxylic acid ethyl ester A solution of the product step j) (284 mg, 0.86 mmol) in dioxane (4.3 ml) was treated with Pd(dppf)$_2$Cl$_2$ (42 mg, 0.051 mmol) and a 2M solution of dimethylzinc in toluene (0.86 ml, 1.72 mmol) at 102° C. for 1 hour. The reaction was cooled to 22° C. and carefully quenched with sat. NH$_4$Cl (3 ml). After the effervescence subsided, the reaction was extracted with EtOAc (3×50 ml). The combined organic layers were dried (MgSO$_4$) passed through a plug of silica-gel eluting with 50:50 hexanes:EtOAc to provide the subtitle compound (216 mg, 95% over 3-steps). MS calculated for C14H19NO2S+H 266, observed 266.

l) 6-Bromo-5,7-dimethyl-3,3a,7,7a-tetrahydro-1H-4-thia-2-aza-cyclopenta[α]pentalene-2-carboxylic acid ethyl ester A solution of the product from step k) (110 mg, 0.42 mmol) in AcOH (1 ml) and CHCl₃ (1 ml) was treated with hydroquinone (5 mg) and NBS (77.8 mg, 0.437 mmol) at 40° C. for 3 hours in the dark. Next, the reaction mixture was carefully quenched with sat. NaHCO₃ (5 ml) and extracted with EtOAc (3×20 ml). The combined organic extracts were dried (MgSO₄) and purified by preparative TLC hexanes:EtOAc (1:1) to give the subtitle compound (24.2 mg, 17%). MS calculated for C14H18BrNO2S+H 344, observed 344, 346.

m.) 6-Bromo-5,7-dimethyl-1,2,3,3a,7,7a-hexahydro-4-thia-2-aza-cyclopenta[α]pentalene The product from step l) (12.6 mg) was treated by the method of Example 16, step b) to give the title compound. ¹H NMR (300 MHz, d₆-DMSO, ppm) 1.31 (d, J=7 Hz, 3H); 2.32 (s, 3H); 3.09-3.21 (m, 2H); 3.22-3.38 (m, 2H); 3.40-3.60 (m, 2H); 3.87-3.98 (m, 1H); 9.00 (br s, 1H); 9.39 (br s, 1H); MS calculated for C11H14BrNS+H 272, observed 272, 274.

Example 28

2-Bromo-4,5,6,7,7a,8-hexahydro-3bH-1-thia-6-aza-cyclopenta[α]indene

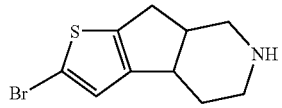

a.) 1-Benzyl-4-trifluoromethanesulfonyloxy-1,2,5,6-tetrahydro-pyridine-3-carboxylic acid ethyl ester (Scheme 5 & 6)

Sodium hydride (60% dispersion on oil, 1.43 g {861 mg}, 35.9 mmol) was washed with anhydrous hexane (2×25 ml) and then suspended in anhydrous ether (107 ml). At 0° C., a solution of 1-Benzyl-4-oxo-piperidine-3-carboxylic acid ethyl ester (7.8 g, 29.9 mmol) in ether (43 ml) was added dropwise and the mixture was stirred for 30 minutes and then cooled to −78° C. Next, triflic anhydride (6 ml, 35.9 mmol) was added and the reaction was slowly warmed to 22° C. over 16 hours. The reaction was quenched with H₂O (100 ml), washed with brine (100 ml) and dried (MgSO₄) providing 9.9 g (84%) of the subtitle compound that was used without further purification.

b.) 1-Benzyl-4-thiophen-3-yl-1,2,5,6-tetrahydro-pyridine-3-carboxylic acid ethyl ester A solution of the product from step a) (9.9 g, 25.2 mmol) was treated with thiophene-3-boronic acid (3.22 g, 25.2 mmol), K₂CO₃ (10.4 g, 75.6 mmol) and tetrakistriphenylphosphine (1.45 g, 1.26 mmol) in DME (126 ml) at 100° C. for 4 hours. Next, the reaction mixture was cooled to 22° C., diluted with H₂O (200 ml) and extracted with EtOAc (400 ml). The organic extract was dried (MgSO₄), concentrated and filtered through a plug of silica gel using hexanes:EtOAc (7:3) to give the subtitle compound (6.02 g, 73%) as an oil. MS calculated for C19H21NO2S+H 328, observed 328.

c.) 1-Benzyl-4-thiophen-3-yl-piperidine-3-carboxylic acid ethyl ester

A solution of the product from step b) (5.83 g, 18 mmol) was dissolved in EtOH (32.4 ml) and treated with 10% Pd/C (Wet Degussa type, 11.7 g) and heated to 40° C. for 2 days under H₂ (1 atm). Next, the Pd/C was removed by filtration through celite, replaced with fresh 10% Pd/C (11.7 g) and the reaction was continued for two more days. The Pd/C was filtered through celite and the EtOH was evaporated in vacuo to provide the subtitle compound (4.5 g, 76%) that was used without further purification. MS calculated for C19H23NO2S+H 330, observed 330.

d.) 1-Benzyl-4-thiophen-3-yl-piperidine-3-carboxylic acid

The product from step c) (4.5 g, 13.7 mmol) was treated with 4 M HCl at 1000C for 16 hours. Next, the reaction was evaporated to dryness, azeotrope with toluene (2×50 ml) and placed on the high vacuum to give the subtitle compound that was used without further purification. MS calculated for C17H19NO2S−H 300, observed 300.

e.) 1-Benzyl-4-thiophen-3-yl-piperidine-3-carbonyl chloride

A solution of the product from step d) (4.68 g, 13.8 mmol) in CH₂Cl₂ (77 ml) was treated with DMF (3-4 drops) and oxalyl chloride (2.72 ml, 31 mmol) at 220C for 1 hour. Next, the solvent was evaporated providing the subtitle compound (4.38 g) that was used without further purification.

f.) 6-Benzyl-3b,4,5,6,7,7a-hexahydro-1-thia-6-aza-cyclopenta[α]inden-8-one

A solution of the product from step e) (4.38 g, 12.3 mmol) in CH₂Cl₂ (18.5 ml) was added dropwise to a slurry of AlCl₃ (4.91 g, 36.9 mmol) in CH₂Cl₂ (42 ml) at 22° C. After 45 minutes, the reaction mixture was poured into ice cold 2 M NaOH (100 ml) and extracted with CH₂Cl₂ (300 ml). The organic extract was dried (MgSO₄) and purified by silica-gel chromatography using a ethyl acetate/hexanes gradient (0% to 50% ethyl acetate) to give the subtitle product (434 mg, 12%). MS calculated for C17H17NOS+H 284, observed 284.

g.) 6-Benzyl-4,5,6,7,7a, 8-hexahydro-3bH-1-thia-6-aza-cyclopenta[α]indene

A slurry of AlCl₃ (571 mg, 4.29 mmol) in CH₂Cl₂ (4 ml) was treated with tert-butylaminoborane (746 mg, 8.58 mmol) at 0° C. and stirred for 30 minutes. Next, a solution of the product from step f) (406 mg, 1.43 mmol) in CH₂Cl₂ (3 ml) was added dropwise to the AlCl₃/borane solution. After 2 hours at 0° C., the crude reaction mixture was poured into cold 10% HCl, treated with 2 M NaOH to pH 12 and extracted with CH₂Cl₂ (3×75 ml). The combined organic extracts were washed with brine (75 ml) and dried (MgSO₄). The solvent was evaporated in vacuo and the crude product was purified by silica-gel chromatography using a ethyl acetate/hexanes gradient (0% to 75% ethyl acetate) to give 279 mg (73%) of the subtitle compound. MS calculated for C17H19NS+H 270, observed 270.

h.) 4, 5, 6, 7,7a, 8-Hexahydro-3bH-1-thia-6-aza-cyclopenta[α]indene

The product from step g) (279 mg, 1.04 mmol) in dichloroethane (5.2 ml) was treated with K₂CO₃ (574 mg, 4.16 mmol) and Ace-Cl (451 μl, 4.16 mmol) at 800C for 16 hours. Next, the reaction mixture was filtered, concentrated and the residue was dissolved in anhydrous MeOH (25 ml) and stirred for 1 hour at 22° C. The MeOH was concentrated and triturated with ether to give 135 mg (60%) of the subtitle compound. MS calculated for C10H13NS+H 180, observed 180.

i) 3b,4,5,7,7a,8-Hexahydro-1-thia-6-aza-cyclopenta[α]indene-6-carboxylic acid tert-butyl ester To a solution of the product from step h) (135 mg, 0.63 mmol) in acetone (1.5 ml) and H₂O (1.5 ml) was added NaHCO₃ (106 mg, 1.26 mmol) and di-tert-butyl dicarbonate (151 mg, 0.69 mmol). The reaction mixture was stirred for 1 hour at room temperature. The reaction mixture was diluted with EtOAc (50 ml), washed with brine (20 ml), dried (MgSO₄), filtered, and evaporated to give the subtitle compound as a clear oil (169 mg, 97%). MS calculated for C15H21NO2S+H 280, observed M-tBu 224.

j.) 2-Bromo-3b,4,5,7,7a, 8-hexahydro-1-thia-6-aza-cyclopenta[α]indene-6-carboxylic acid tert-butyl ester A solution of the product from step i) (170 mg, 0.61 mmol) in AcOH (1.5 ml) and CHCl₃ (1.5 ml) was treated with NBS (110 mg, 0.62 mmol) at 22° C. for 30 minutes. Next, the reaction was carefully quenched with sat. NaHCO₃ (10 ml), extracted with EtOAc (2×75 ml) and the combined organic extracts were dried (MgSO₄) and solvent evaporated in vacuo. The crude product was purified by silica-gel chromatography using a ethyl acetate/hexanes gradient (10% to 50% ethyl acetate) to give the subtitle compound. ¹H NMR (300 MHz, CDCl₃, ppm) 1.45 (s, 9H); 1.50-1.70 (m, 2H); 1.90-2.02 (m, 1H); 2.48-2.62 (m, 1H); 2.88-3.01 (m, 1H); 3.12-3.48 (m, 3H); 3.52-3.63 (m, 1H) 6.78 (s, 1H); MS calculated for C15H20BrNO2S+H 358, observed M-tBu 302, 304.

k.) 2-Bromo-4,5,6,7,7a,8-hexahydro-3bH-1-thia-6-aza-cyclopenta[α]indene

The product from step j) was treated with 4M HCl in dioxane for 30 minutes. Next, the solvent was concentrated and the product was triturated with ether to give the title compound. MS calculated for C10H12BrNS+H 258, observed 258, 260.

Example 29

2-Bromo-4,5,6,7,7a,8-hexahydro-3bH-1-thia-5-aza-cyclopenta[α]indene

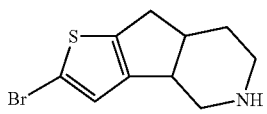

a.) 1-Benzyl-5-trifluoromethanesulfonyloxy-1,2,3,6-tetrahydro-pyridine-4-carboxylic acid ethyl ester
(Scheme 5 & 6)

Sodium hydride (60% dispersion on oil, 1.58 g {947 mg}, 39.5 mmol) was washed with anhydrous hexane (2×25 ml) and then suspended in anhydrous ether (118 ml). At 0° C., a solution of 1-Benzyl-4-oxo-piperidine-3-carboxylic acid ethyl ester (8.6 g, 32.9 mmol) in ether (47 ml) was added dropwise and the mixture was stirred for 30 minutes and then cooled to –78° C. Next, triflic anhydride (6.6 ml, 39.5 mmol) was added and the reaction mixture was slowly warmed to 22° C. over 16 hours. The mixture was quenched with H₂O (100 ml) and the organic layer washed with brine (100 ml), dried (MgSO₄), and solvent evaporated in vacuo to give 10.7 g (83%) of the subtitle compound that was used without further purification.

b.) 1-Benzyl-5-thiophen-3-yl-1,2,3,6-tetrahydro-pyridine-4-carboxylic acid ethyl ester A solution of the product from step a) (10.7 g, 27.2 mmol) was treated with thiophene-3-boronic acid (3.48 g, 27.2 mmol), K₂CO₃ (11.3 g, 81.6 mmol) and tetrakistriphenylphosphine (1.57 g, 1.36 mmol) in DME (136 ml) at 100° C. for 4 h. Next, the reaction mixture was cooled to 22° C., diluted with H₂O (200 ml) and extracted with EtOAc (400 ml). The organic extract was dried (MgSO₄), concentrated filtered through a plug of silica gel using hexanes:EtOAc (7:3) to give the subtitle compound (6.78 g, 76%) as an oil. MS calculated for C19H21NO2S+H 328, observed 328.

c.) 1-Benzyl-3-thiophen-3-yl-piperidine-4-carboxylic acid ethyl ester

A solution of the product from step b) (6.69 g, 20.4 mmol) was dissolved in EtOH (37 ml) and treated with 10% Pd/C (Wet Degussa type, 13.4 g) and heated to 40° C. for 2 days under H₂ (1 atm). Next, the Pd/C was removed by filtration through celite, replaced with fresh 10% Pd/C (13.4 g) and the reaction was continued for two more days. The Pd/C was removed by filtration through celite and the EtOH was evaporated in vacuo to provide the subtitle compound (4.78 g, 71%). MS calculated for C19H23NO2S+H 330, observed 330.

d.) 1-Benzyl-3-thiophen-3-yl-piperidine-4-carboxylic acid

The product from step c) (4.78 g, 14.5 mmol) was treated with 4 M HCl at 100° C. for 16 hours. Next, the reaction was evaporated to dryness, azeotroped with toluene (2×50 ml) and placed on the high vacuum to give the subtitle compound. MS calculated for C17H19NO2S–H 300, observed 300.

e.) 1-Benzyl-3-thiophen-3-yl-piperidine-4-carbonyl chloride

A solution of the product from step d) (4.9 g, 14.5 mmol) in CH₂Cl₂ (81 ml) was treated with DMF (3-4 drops) and oxalyl chloride (2.85 ml, 32.6 mmol) at 22° C. for 1 hour. Next, the solvent was evaporated providing the subtitle compound (4.9 g, 95%).

f.) 5-Benzyl-3b,4,5,6,7,7a-hexahydro-1-thia-5-aza-cyclopenta[α]inden-8-one

A solution of the product from step e) (4.9 g, 13.8 mmol) in CH₂Cl₂ (21 ml) was added dropwise to a slurry of AlCl₃ (5.51 g, 41.4 mmol) in CH₂Cl₂ (47 ml) at 22° C. After 45 minutes, the reaction mixture was poured into ice cold 2 M NaOH (100 ml) and extracted with CH₂Cl₂ (300 ml). The organic extract was dried (MgSO₄), solvent evaporated in vacuo and residue purified by silica-gel chromatography using a ethyl acetate/hexanes gradient (0% to 50% ethyl acetate) to give the subtitle compound (1.8 g, 46%). MS calculated for C17H17NOS+H 284, observed 284.

g.) 5-Benzyl-4,5,6,7,7a,8-hexahydro-3bH-1-thia-5-aza-cyclopenta[α]indene

A slurry of AlCl₃ (1.32 g, 9.96 mmol) in CH₂Cl₂ (6 ml) was treated with tert-butylaminoborane (1.73 g, 19.92 mmol) at 0° C. and stirred for 30 minutes. Next, a solution of the product from step f) (941 mg, 3.32 mmol) in CH₂Cl₂ (3 ml) was added dropwise to the AlCl₃/borane solution. After 2 hours at 0° C., the crude reaction mixture was poured into cold 10% HCl, treated with 2 M NaOH to pH 12 and extracted with CH₂Cl₂ (3×75 ml). The combined organic extracts were washed with brine (75 ml), dried (MgSO₄) and solvent evaporated invacuo. The crude product was purified by silica-gel chromatography using a ethyl acetate/hexanes gradient (0% to 75% ethyl acetate) to give the subtitle compound. MS calculated for C17H19NS+H 270, observed 270.

h.) 4,5,6,7,7a,8-Hexahydro-3bH-1-thia-5-aza-cyclopenta[α]indene

The product from step g) (963 mg, 3.58 mmol) in dichloroethane (18 ml) was treated with K₂CO₃ (1.97 g, 14.3 mmol) and Ace-Cl (1.54 ml, 14.3 mmol) at 80° C. for 16 hours. Next, the reaction mixture was filtered, concentrated and the residue was dissolved in anhydrous MeOH (25 ml) and stirred for 1 h at 22° C. The MeOH was concentrated and triturated with ether to give 467 mg (61%) of the subtitle compound. MS calculated for C10H13NS+H 180, observed 180.

i.) 3b,4,6,7,7a, 8-Hexahydro-1-thia-5-aza-cyclopenta[α]indene-5-carboxylic acid tert-butyl ester A solution of the product from step h) (467 mg, 2.17 mmol) in acetone (5.4 ml) and H₂O (5.4 ml) was treated with NaHCO₃ (364 mg, 4.34 mmol) and di-tert-butyl dicarbonate (521 mg, 2.39 mmol). The reaction mixture was stirred for 1 hour at room temperature. The reaction mixture was diluted with EtOAc (50 ml) and washed with brine (20 ml). The organic layer was dried (MgSO₄), filtered, solvent evaporated in vacuo to give the subtitled compound as an clear oil (529 mg, 87%). MS calculated for C15H21NO2S+H 280, observed M-tBu 224.

j.) 2-Bromo-3b,4,6,7,7a,8-hexahydro-1-thia-5-aza-cyclopenta[α]indene-5-carboxylic acid tert-butyl ester A solution of the product from step i) (529 mg, 1.90 mmol) in AcOH (4.75 ml) and CHCl₃ (4.75 ml) was treated with NBS (345 mg, 1.94 mmol) at 22° C. for 30 minutes. Next, the reaction was carefully quenched with sat. NaHCO₃ (10 ml), extracted with EtOAc (2×75 ml) and the organic layer was dried (MgSO₄). The crude product was purified by silica-gel chromatography using a ethyl acetate/hexanes gradient (10% to 50% ethyl acetate) to give the subtitle compound (202 mg, 30%). ¹H NMR (300 MHz, CDCl₃, ppm) 1.43 (s, 9H); 1.56-1.68 (m, 1H); 1.78-1.90 (m, 1H); 2.55-2.63 (m, 1H); 2.86-3.08 (m, 2H); 3.09-3.22 (m, 2H); 3.42-3.82 (m, 3H); 6.78 (s, 1H); MS calculated for C15H20BrNO2S+H 358, observed M-tBu 302, 304.

k.) 2-Bromo-4,5,6,7,7a,8-hexahydro-3bH-1-thia-5-aza-cyclopenta[α]indene

The product from step j) was treated with 4M HCl in dioxane for 30 minutes. Next, the solvent was concentrated and the product was triturated with ether to give the title compound. MS calculated for C10H12BrNS+H 258, observed 258, 260.

Example 30

2-Bromo-4,5,6,7,7a,8-hexahydro-3bH-3-thia-5-aza-cyclopenta[α]indene

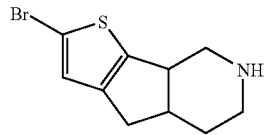

a.) 1-Benzyl-5-thiophen-2-yl-1,2,3,6-tetrahydro-pyridine-4-carboxylic acid ethyl ester (Scheme 5 & 6)

A solution of the product from Example 29, step a) (17.9 g, 45.5 mmol) was treated with thiophene-2-boronic acid (5.82 g, 45.5 mmol), K₂CO₃ (18.8 g, 136.5 mmol) and tetrakistriphenylphosphine (2.63 g, 2.27 mmol) in DME (227 ml) at 100° C. for 4 hours. Next, the reaction mixture was cooled to 22° C., diluted with H₂O (400 ml) and extracted with EtOAc (800 ml). The organic extract was dried (MgSO₄), concentrated and the crude was filtered through a plug of silica gel using hexanes:EtOAc (7:3) to give the subtitle compound (8.95 g, 60%) as an oil. MS calculated for C19H21NO2S+H 328, observed 328.

b.) 1-Benzyl-3-thiophen-2-yl-piperidine-4-carboxylic acid ethyl ester

A solution of the product from step a) (3.3 g, 10.1 mmol) was dissolved in EtOAc (50 ml) and treated with 10% Pd/C (Wet Degussa type, 6.6 g) under H₂ (52 psi). After 24 hours, the Pd/C was removed by filtration through celite, replaced with fresh 10% Pd/C (6.6 g) and the reaction was continued for 24 hours. Finally, the Pd/C was removed by filtration through Celite and the EtOH was evaporated in vacuo to provide the subtitle compound (2.9 g, 87%). MS calculated for C19H23NO2S+H 330, observed 330.

c.) 1-Benzyl-3-thiophen-2-yl-piperidine-4-carboxylic acid

The product from step b) (2.9 g, 8.8 mmol) was treated with 4 M HCl (200 ml) at 100° C. for 16 hours. Next, the reaction was evaporated to dryness, azeotroped with toluene (2×50 ml) and placed on the high vacuum to give the subtitle compound (2.9 g, 98%). MS calculated for C17H19NO2S–H 300, observed 300.

d.) 1-Benzyl-3-thiophen-2-yl-piperidine-4-carbonyl chloride

A solution of the product from step c) (2.9 g, 8.6 mmol) in $CH_2Cl_2$ (100 ml) was treated with DMF (4-5 drops) and oxalyl chloride (1.51 ml, 17.2 mmol) at 22° C. for 1 hour. Next, the solvent was evaporated in vacuo to give the subtitle compound that was used without further purification (2.9 g, 95%).

e.) 5-Benzyl-3b,4,5,6,7,7a-hexahydro-3-thia-5-aza-cyclopenta[α]inden-8-one

A solution of the product from step d) (2.9 g, 8.15 mmol) in $CH_2Cl_2$ (12 ml) was added dropwise to a slurry of $AlCl_3$ (3.26 g, 24.5 mmol) in $CH_2Cl_2$ (28 ml) at 220C. After 45 minutes, the reaction mixture was poured into ice cold 2 M NaOH (100 ml) and extracted with $CH_2Cl_2$ (300 ml). The organic extract was dried ($MgSO_4$), solvent evaporated in vacuo, and residue purified by silica-gel chromatography using a ethyl acetate/hexanes gradient (0% to 50% ethyl acetate) to give the subtitle compound (1.32 g, 57%). MS calculated for C17H17NOS+H 284, observed 284.

f) 5-Benzyl-4,5,6,7,7a,8-hexahydro-3bH-3-thia-5-aza-cyclopenta[α]indene

A slurry of $AlCl_3$ (946 mg, 7.11 mmol) in $CH_2Cl_2$ (7 ml) was treated with tert-butylaminoborane (1.24 g, 14.22 mmol) at 0° C. and stirred for 30 minutes. Next, a solution of the product from step e) (671 mg, 2.37 mmol) in $CH_2Cl_2$ (5 ml) was added dropwise to the $AlCl_3$/borane solution. After 2 hours at 0° C., the crude reaction mixture was poured into cold 10% HCl, treated with 2 M NaOH to pH 12 and extracted with $CH_2Cl_2$ (3×75 ml). The combined organic extracts were washed with brine (75 ml), dried ($MgSO_4$), and solvent evaporated in vacuo leaving the crude product that was purified by silica-gel chromatography using a ethyl acetate/hexanes gradient (0% to 75% ethyl acetate) to give the subtitle compound (409 mg, 64%). MS calculated for C17H19NS+H 270, observed 270.

g.) 4,5,6,7,7a,8-Hexahydro-3bH-3-thia-5-aza-cyclopenta[α]indene

The product from step f) (409 mg, 1.52 mmol) in dichloroethane (8 ml) was treated with $K_2CO_3$ (839 mg, 6.08 mmol) and Ace-Cl (658 μl, 6.08 mmol) at 80° C. for 16 hours. Next, the reaction mixture was filtered, concentrated and the residue was dissolved in anhydrous MeOH (25 ml) and stirred for 1 hour at 22° C. The MeOH was concentrated and triturated with ether producing to give 215 mg (66%) of the subtitle compound as its HCl salt. MS calculated for C10H13NS+H 180, observed 180.

h.) 3b,4,6,7,7a-Hexahydro-3-thia-5-aza-cyclopenta[α]indene-5-carboxylic acid tert-butyl ester A solution of the product from step g) (215 mg, 1 mmol) in acetone (2.75 ml) and $H_2O$ (2.75 ml) was treated with $NaHCO_3$ (168 mg, 2.0 mmol) and di-tert-butyl dicarbonate (240 mg, 1.1 mmol). The reaction mixture was stirred for 1 hour at room temperature. The reaction mixture was diluted with EtOAc (50 ml) and washed with brine (20 ml). The organic layer was dried ($MgSO_4$), filtered, and solvent evaporated in vacuo to give the subtitled compound 279 mg (100%) as a clear oil. MS calculated for Cl $5H_{21}NO2S+H$ 280, observed M-tBu 224.

i.) 2-Bromo-3b,4,6,7,7a,8-hexahydro-3-thia-5-aza-cyclopenta[α]indene-5-carboxylic acid tert-butyl ester A solution of the product from step h) (279 mg, 1.0 mmol) in AcOH (2.5 ml) and $CHCl_3$ (2.5 ml) was treated with NBS (182 mg, 1.02 mmol) at 220C for 30 minutes. Next, the reaction was carefully quenched with sat. $NaHCO_3$ (10 ml), extracted with EtOAc (2×75 ml) and the combined organic extracts were dried ($MgSO_4$) and the solvent evaporated in vacuo leaving the crude product that was purified by silica-gel chromatography using a ethyl acetate/hexanes gradient (10% to 50% ethyl acetate) to give the subtitle compound (182 mg, 51%). $^1H$ NMR (300 MHz, $CDCl_3$, ppm) 1.46 (s, 9H); 1.52-1.69 (m, 1H); 1.75-1.90 (m, 1H); 2.42-2.57 (m, 1H); 2.82-2.97 (m, 2H); 3.10-3.40 (m, 3H); 3.49 (m, 2H); 6.80 (s, 1H); MS calculated for C15H20BrNO2S+H 358, observed M-tBu 302, 304.

j.) 2-Bromo-4,5,6,7,7a,8-hexahydro-3bH-3-thia-5-aza-cyclopenta[α]indene

The product from step i) was treated with 4M HCl in dioxane for 30 minutes. Next, the solvent was concentrated and the product was triturated with ether to give the title compound. MS calculated for C10H12BrNS+H 258, observed M-tBu 258, 260.

Example 31

2-Bromo-4,5,6,7,7a,8-hexahydro-3bH-3-thia-6-aza-cyclopenta[α]indene

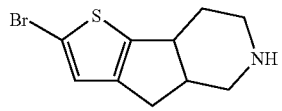

a.) 1-Benzyl-4-thiophen-2-yl-1,2,5,6-tetrahydro-pyridine-3-carboxylic acid ethyl ester (Scheme 5 & 6)

A solution of the product from example 28, step a) (34 g, 86.5 mmol) was treated with thiophene-2-boronic acid (11.1 g, 86.5 mmol), $K_2CO_3$ (35.8 g, 259.5 mmol) and tetrakistriphenylphosphine (5.01 g g, 4.34 mmol) in DME (400 ml) at 100° C. for 4 hours. Next, the reaction mixture was cooled to 22° C., diluted with $H_2O$ (400 ml) and extracted with EtOAc (800 ml). The organic extract was dried ($MgSO_4$), concentrated and the crude was filtered through a plug of silica gel using hexanes:EtOAc (7:3) to give the subtitle compound (17.6 g, 62%) as an oil. MS calculated for C19H21NO2S+H 328, observed 328.

b.) 1-Benzyl-4-thiophen-2-yl-piperidine-3-carboxylic acid ethyl ester

A solution of the product from step a) (17.6 g, 53.8 mmol) was dissolved in EtOAc (150 ml) and treated with 10% Pd/C (Wet Degussa type, 17.6 g) under $H_2$ (52 psi). After 24 hours, the Pd/C was removed by filtration through celite, replaced with fresh 10% Pd/C (17.6 g) and the reaction was continued for 24 hours. Finally, the Pd/C was removed by filtration through celite and the EtOH was evaporated in vacuo to give the subtitle compound (6.83 g, 38%). MS calculated for $C_{19}H_{23}NO_2S+H$ 330, observed 330.

c.) 1-Benzyl-4-thiophen-2-yl-piperidine-3-carboxylic acid

The product from step b) (6.83 g, 20.7 mmol) was treated with 4 M HCl (400 ml) at 100° C. for 16 hours. Next, the reaction was evaporated to dryness, azeotroped with toluene (2×50 ml) and placed on the high vacuum to give the subtitle compound (7 g, 100%). MS calculated for $C_{17}H_{19}NO_2S-H$ 300, observed 300.

d.) 1-Benzyl-4-thiophen-2-yl-piperidine-3-carbonyl chloride

A solution of the product from step c) (7 g, 20.7 mmol) in $CH_2Cl_2$ (100 ml) was treated with DMF (4-5 drops) and oxalyl chloride (3.61 ml, 41.4 mmol) at 22° C. for 1 hour. Next, the solvent was evaporated providing the subtitle compound (7.37 g, 100%) that was used without further purification.

e.) 6-Benzyl-3b,4,5,6,7,7a-hexahydro-3-thia-6-aza-cyclopenta[α]inden-8-one

A solution of the product from step d) (7.37 g, 20.7 mmol) in $CH_2Cl_2$ (103 ml) was added dropwise to a slurry of $AlCl_3$ (8.26 g, 62 mmol) in $CH_2Cl_2$ (28 ml) at 22° C. After 45 minutes, the reaction mixture was poured into ice cold 2 M NaOH (100 ml) and extracted with $CH_2Cl_2$ (300 ml). The organic extract was dried ($MgSO_4$) and purified by silica-gel chromatography using a ethyl acetate/hexanes gradient (0% to 50% ethyl acetate) to give 4 g (68%) of the subtitle compound. MS calculated for $C_{17}H_{17}NOS+H$ 284, observed 284.

f.) 6-Benzyl-4,5,6,7,7a, 8-hexahydro-3bH-3-thia-6-aza-cyclopenta[α]indene

A slurry of $AlCl_3$ (2.74 g, 20.76 mmol) in $CH_2Cl_2$ (21 ml) was treated with tert-butylaminoborane (3.57 g, 41.52 mmol) at 0° C. and stirred for 30 minutes. Next, a solution of the product from step e) (1.96 g, 6.92 mmol) in $CH_2Cl_2$ (15 ml) was added dropwise to the $AlCl_3$/borane solution. After 2 hours at 0° C., the crude reaction mixture was poured into cold 10% HCl, treated with 2 M NaOH to pH 12 and extracted with $CH_2Cl_2$ (3×75 ml). The combined organic extracts were washed with brine (75 ml), dried ($MgSO_4$), and the solvent evaporated in vacuo leaving the crude product that was purified by silica-gel chromatography using a ethyl acetate/hexanes gradient (0% to 75% ethyl acetate) to give 1.16 g (62%) of the subtitle compound. MS calculated for $C_{17}H_{19}NS+H$ 270, observed 270.

g.) 4,5,6,7,7a,8-Hexahydro-3bH-3-thia-6-aza-cyclopenta[α]indene

The product of step f) (1.16 g, 4.3 mmol) in dichloroethane (21 ml) was treated with $K_2CO_3$ (2.38 g, 17.2 mmol) and Ace-Cl (1.86 ml, 17.2 mmol) at 800C for 16 hours. Next, the reaction mixture was filtered, concentrated and the residue was dissolved in anhydrous MeOH (25 ml) and stirred for 1 hour at 22° C. The MeOH was concentrated and triturated with ether to give 874 mg (94%) of the subtitle compound. MS calculated for $C_{10}H_{13}NS+H$ 180, observed 180.

h.) 3b,4,5,17,7a,8-Hexahydro-3-thia-6-aza-cyclopenta[α]indene-6-carboxylic acid ethyl ester A 0° C. solution of the product from step g) (874 mg, 4.05 mmol) in $CH_2Cl_2$ (20 ml) was treated with triethylamine (1.69 ml, 12.15 mmol) and ethyl chloroformate (466 μl, 4.86 mmol) and the reaction was warmed to 220C. Next, the reaction mixture was diluted with $CH_2Cl_2$ (50 ml) and washed with brine (25 ml). The organic layer was dried ($MgSO_4$) and solvent evaporated in vacuo leaving the crude product that was purified by silica-gel chromatography (hexanes:EtOAc-50:50) to give 722 mg (71%) of the subtitle compound. MS calculated for $C_{13}H_{17}NO_2S+H$ 252, observed 252.

i.) 2-Bromo-3b,4,5,7,7a, 8-hexahydro-3-thia-6-aza-cyclopenta[α]indene-6-carboxylic acid ethyl ester A solution of the product from step h) (722 mg, 2.88 mmol) in AcOH (7.2 ml) and $CHCl_3$ (7.2 ml) was treated with NBS (529 mg, 2.97 mmol) at 22° C. for 30 minutes. Next, the reaction was carefully quenched with sat. $NaHCO_3$ (10 ml), extracted with EtOAc (2×75 ml) and the combined organic extracts were dried ($MgSO_4$) and solvent evaporated in vacuo leaving the crude product that was purified by silica-gel chromatography using a ethyl acetate/hexanes gradient (10% to 50% ethyl acetate) to give the subtitle compound. MS calculated for $C_{15}H_{20}BrNO_2S+H$ 358, observed M-tBu 302, 304.

j.) 2-Bromo-4,5,6,7,7a,8-hexahydro-3bH-3-thia-6-aza-cyclopenta[α]indene

The product from step i) was treated by the method of Example 16, step b) to give the title compound. MS calculated for $Cl H_{14}BrNS+H$ 272, observed 272, 274.

Example 32

1-Bromo-2-methyl-4,5,6,7,7a,8-hexahydro-3bH-3-thia-6-aza-cyclopenta[α]indene

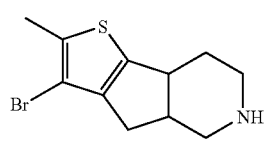

a.) 2-Methyl-3b,4,5,7,7a, 8-hexahydro-3-thia-6-aza-cyclopenta[α]indene-6-carboxylic acid ethyl ester (Scheme 7)

A solution of the product from Example 31, step i) (622 mg, 1.89 mmol) in dioxane (9.4 ml) was treated with Pd(dppf)

$_2Cl_2$ (92 mg, 0.113 mmol) and a 2M solution of dimethylzinc in toluene (1.89 ml, 3.78 mmol) at 102° C. for 1 hour. The reaction was cooled to 22° C. and carefully quenched with sat. $NH_4Cl$ (3 ml). After the effervescence subsided, the reaction was extracted with EtOAc (3×50 ml). The combined organic extracts were dried ($MgSO_4$), concentrated and eluted through a plug of silica gel using 50:50 hexanes:EtOAc to give 334 mg (66%) of the subtitle compound. MS calculated for C14H19NO2S+H 266, observed 266.

b.) 1-Bromo-2-methyl-3b,4,5,7,7a, 8-hexahydro-3-thia-6-aza-cyclopenta[α]indene-6-carboxylic acid ethyl ester A solution of the product from step a) (334 mg, 1.26 mmol) in AcOH (3 ml) and $CHCl_3$ (3 ml) was treated with hydroquinone (5 mg) and NBS (269 mg, 1.51 mmol) at 40° C. for 3 hour in the dark. Next, the reaction mixture was carefully quenched with sat. $NaHCO_3$ (5 ml) and extracted with EtOAc (3×20 ml). The combined organic extracts were dried ($MgSO_4$) and the solvent evaporated in vacuo leaving the crude product that was purified by preparative TLC (hexanes:EtOAc-1:1) to give the subtitle compound. MS calculated for C14H18BrNO2S+H 344, observed 344, 346.

c.) 1-Bromo-2-methyl-4,5,6,7,7a, 8-hexahydro-3bH-3-thia-6-aza-cyclopenta[α]indene The product from step b) treated by the method of Example 16, step b) to give the title compound.

Example 33

3-Bromo-2-methyl-4,5,6,7,7a,8-hexahydro-3bH-1-thia-5-aza-cyclopenta[α]indene

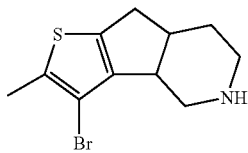

a.) 3b,4,6,7,7a,8-Hexahydro-1-thia-5-aza-cyclopenta[α]indene-5-carboxylic acid ethyl ester (Scheme 7)

A 0° C. solution of product from Example 29, step h) (885 mg, 4.1 mmol) in $CH_2Cl_2$ (20 ml) was treated with triethylamine (1.71 ml, 12.3 mmol) and ethyl chloroformate (472 μl, 4.92 mmol) and the reaction was warmed to 22° C. Next, the reaction mixture was diluted with $CH_2Cl_2$ (20 ml) and washed with brine (25 ml). The organic layer was dried ($MgSO_4$) and the solvent evaporated in vacuo to give the crude product that was purified by silica-gel chromatography (hexanes:EtOAc-50:50) to give 748 mg (73%) of the subtitle compound. MS calculated for C13H17NO2S+H 252, observed 252.

b.) 2-Bromo-3b,4,6,7,7a,8-hexahydro-1-thia-5-aza-cyclopenta[α]indene-5-carboxylic acid ethyl ester A solution of the product from step a) (748 mg, 2.98 mmol) in AcOH (7.5 ml) and $CHCl_3$ (7.5 ml) was treated with NBS (546 mg, 3.07 mmol) at 22° C. for 30 minutes. Next, the reaction was carefully quenched with sat. $NaHCO_3$ (10 ml), extracted with EtOAc (2×75 ml). The combined organic extracts were dried ($MgSO_4$) and solvent evaporated in vacuo leaving the crude product that was purified by silica-gel chromatography using ethyl acetate/hexanes gradient (10% to 50% ethyl acetate) to give 863 mg (88%) of the subtitle compound. MS calculated for C15H20BrNO2S+H 330, observed 330, 332.

c.) 2-Methyl-3b,4,6,7,7a,8-hexahydro-1-thia-5-aza-cyclopenta[α]indene-5-carboxylic acid ethyl ester A solution of the product from step b) (863 mg, 2.62 mmol) in dioxane (13.1 ml) was treated with $Pd(dppf)_2Cl_2$ (128 mg, 0.157 mmol) and a 2M solution of dimethylzinc in toluene (2.62 ml, 5.24 mmol) at 102° C. for 1 h. The reaction was cooled to 220C and carefully quenched with sat. $NH_4Cl$ (3 ml). After the effervescence subsided, the reaction was extracted with EtOAc (3×50 ml). The combined organic extracts were dried ($MgSO_4$), concentrated and eluted through a plug of silica-gel using 50:50 hexanes:EtOAc to give 411 mg (59%) of the subtitle compound. MS calculated for C14H19NO2S+H 266, observed 266.

d.) 3-Bromo-2-methyl-3b,4,6,7,7a,8-hexahydro-1-thia-5-aza-cyclopenta[α]indene-5-carboxylic acid ethyl ester A solution of the product from step c) (411 mg, 1.55 mmol) in AcOH (3.8 ml) and $CHCl_3$ (3.8 ml) was treated with hydroquinone (5 mg) and NBS (331 mg, 1.86 mmol) at 40° C. for 3 hours in the dark. Next, the reaction mixture was carefully quenched with sat. $NaHCO_3$ (5 ml) and extracted with EtOAc (3×20 ml). The combined organic extracts were dried ($MgSO_4$) and the solvent evaporated in vacuo leaving the crude product that was purified by preparative TLC (hexanes:EtOAc-1:1) to give the subtitle compound. MS calculated for C14H18BrNO2S+H 344, observed 344, 346.

e.) 3-Bromo-2-methyl-4,5,6,7,7a, 8-hexahydro-3bH-1-thia-5-aza-cyclopenta[α]indene The product from step d) was treated by the method of Example 16, step b) to give the title compound. MS calculated for C11H14BrNS+H 272, observed 272, 274.

Example 34

7-Methyl-3b,4,5,6,6a-7-hexahydro-1-thia-5-aza-cyclopenta[α]pentalene

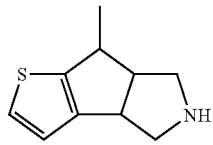

a.) 3-Thiophen-3-yl-acrylic acid ethyl ester (Scheme 3)

Potassium bis(trimethylsilyl)amide (3.92 g, 19.7 mol) was added to a solution of 18-Crown-6 (9.95 g, 37.6 mmol) and [Bis-(2,2,2 trifluoro-ethoxy)-phosphoryl]-acetic acid ethyl ester (6.54 g, 19.7 mmol) in dry THF (200 mL) at −78° C. After 30 minutes of stirring at this temperature, thiophene-3-carbaldehyde (2.0 g, 19.7 mmol) was added and the reaction was stirred for 3 hours at −780C after which the reaction was quenched with saturated ammonium chloride (200 mL). The reaction mixture was allowed to come to room temperature and was extracted with ethyl acetate (3×250 mL) and the combined organic extracts were washed with 10% HCl (200 mL), brine (200 mL) and dried with MgSO$_4$ Evaporation of the solvent in vacuo gave the crude product that was purified by silica-gel chromatography using a 0-40% ethylacetate-hexane gradient to afford the subtitle compound (2.7 g, 82.7%). MS calculated for $C_9H_{10}O_2S$+H: 183, observed: 183; $^1$H NMR (300 MHz, CDCl$_3$, ppm) 1.31 (t, J=7 Hz, 3H); 4.22 (q, J=7 Hz, 2H); 5.83 (d, J=13 Hz, 1H); 6.87 (d, J=7 Hz, 1H); 7.24-7.28 (m, 1H); 7.54 (dd, J$_1$=5 Hz, J$_2$=1 Hz, 1H); 8.07 (br d, J=3 Hz, 1H).

b.) 1-(1-Phenyl-ethyl)-4-thiophen-3-yl-pyrrolidine-3-carboxylic acid ethyl ester (S)-(-)-N-methoxymethyl-N-(trimethylsilyl)methyl-1-phenylethylamine(4.47 g, 17.8 mmol) was added to a solution of the product from step a) (2.70 g, 14.8 mmol) in 150 mL of dichloromethane at 0° C. Trifluoroacetic acid (0.169 g, 1.48 mmol) in 2 mL of dichloromethane was added dropwise and the reaction mixture was allowed to come room temperature and was stirred overnight. Next, the reaction mixture was quenched with 50 mL of saturated NaHCO$_3$. The organic phase was washed with brine, dried (MgSO$_4$), and solvent evaporated in vacuo to give the crude product that was purified by silica-gel chromatography using a ethyl acetate/hexanes gradient (2% to 45% ethyl acetate) to give diastereomer 1 (R$_{f(Diastereomer\ 1)}$: 0.40, TLC-9:1/hexane:ethylacetate) and diastereomer 2 (R$_{f(Diastereomer\ 2)}$: 0.33, TLC-9:1/hexane:ethylacetate). MS calculated for $C_{19}H_{23}NO_2S$+H: 330, observed: 330. The two diastereomers were individually carried through the following synthetic steps to give enantiomers 1 and 2 (synthesis of enantiomer 1 shown below).

c.) 1-(1-Phenyl-ethyl)-4-thiophen-3-yl-pyrrolidine-3-carboxylic acid

The product from step b), diastereomer 1 (1.4 g, 4.3 mmol) was dissolved in 12 M HCl (10 mL) and was stirred at 80° C. for 12 hours. The reaction mix then was cooled to room temperature and evaporated to dryness to afford the subtitle compound. MS calculated for $C_{17}H_{19}NO_2S$+H: 302, observed: 302.

d.) 1-(1-Phenyl-ethyl)-4-thiophen-3-yl-pyrrolidine-3-carbonyl chloride

The product from step c) (1064 mg, 3.53 mmol) was dissolved in 20 mL of dichloromethane and cooled to 0° C. under N$_2$ atmosphere and oxalyl chloride (1345 mg, 10.59 mmol) was added, followed by 2 drops of DMF. The reaction was stirred at 0° C. for 15 minutes and was allowed to come to room temperature. The reaction mixture was stirred for 1.5 hours and was evaporated to dryness to give the subtitle compound as a solid. MS calculated for $C_{17}H_{18}ClNOS$+H: 320, observed as methyl ester [dissolved in methanol]+H: 316.

e.) 5-(1-Phenyl-ethyl)-4,5,6,6a-tetrahydro-3bH-1-thia-5-azacyclopenta[a]-pentalen-7-one The product from step d) (1162 mg, 3.64 mmol) dissolved in 20 mL of dichloromethane was added dropwise to a vigorously stirred suspension of AlCl$_3$ (1456 mg, 10.92 mmol) in 20 mL of dichloromethane at 0° C. The reaction mixture was stirred at 0° C. for 30 minutes and was quenched with saturated NaHCO$_3$, filtered through Celite and the filtrate was extracted with dichloromethane (3×50 mL). The combined organic extracts were dried (MgSO$_4$) and solvent evaporated in vacuo to give the crude product that was purified by silica-gel chromatography using 5-70% ethylacetate-hexane gradient to afford the subtitled compound (303 mg, yield: 30.6% over two steps). MS calculated for $C_{17}H_{17}NOS$+H: 284, observed: 284.

f.) 7-Methylene-5-(1-phenyl-ethyl)-3b, 4,5,6,6a,7-hexahydro-1-thia-5-aza-cyclopenta[a]pentatene Potassium bis(trimethylsilyl)amide (308 mg, 1.55 mmol) was added to a solution of methyl triphenylphosphonium bromide (575 mg, 1.61 mmol) in 7 mL of THF at 0° C. After 30 minutes of stirring at 0° C., the product from step e) (303 mg, 1.07 mmol) dissolved in 2 mL of THF was added to the reaction mixture and was allowed to come to room temperature over 1 hour. The reaction mixture was diluted with dichloromethane (30 mL) and was washed with brine, dried (MgSO$_4$) and concentrated to an oil. The crude was purified by column chromatography (SiO$_2$) using 5-55% ethylacetate-hexane gradient to afford the subtitle compound (226 mg, yield: 74.8%). MS calculated for $C_{18}H_{19}NS$+H: 282, observed: 282.

g.) 7-Methyl-5-(1-phenyl-ethyl)-3b,4,5,6,6a,7-hexahydro-1-thia-5-aza-cyclopenta[a]pentalene The product of step f) (226 mg, 0.80 mmol) was added to a suspension of 10% Pd/C (339 mg) in 8 mL of methanol. The reaction chamber was evacuated from air and was filled with H$_2$ (1 atm). The reaction mixture was stirred under H$_2$ for 12 hours at 35° C. The reaction mixture was filtered through Celite and evaporated in vacuo to give the subtitle compound as an oil (165 mg, 72.5%). MS calculated for $C_{18}H_{21}NS$+H: 284, observed: 284.

h.) 7-Methyl-3b,4,5,6,6a,7-hexahydro-1-thia-5-aza-cyclopenta[a]pentalene

K$_2$CO$_3$ (320 mg, 2.32 mmol) was added to a solution of the product from step g) (165 mg, 0.58 mmol) in 6 mL followed by the addition of 2-chloroethylchloroformate (332 mg, 2.32 mmol) under vigorous stirring at room temperature. Next, the reaction was stirred for two hours at 75° C. after which the reaction mixture was cooled, filtered and the solvent was evaporated to leave an oily residue that was then dissolved in dry methanol (10 mL) and was stirred at room temperature for one hour. The solvent was evaporated and the residue was triturated in diethyl ether (5 mL) to give the subtitle compound as its HCl salt. MS calculated for $C_{10}H_{13}NS$+H: 180, observed: 180. $^1$H NMR (CDCl$_3$300 MHz) δ 1.32 (d, 3H), 1.93 (s, 1H), 3.04 (m, 1H), 3.18 (m, 2H), 3.47 (m, 3H), 3.78 (m, 1H), 6.83 (d, 1H), 7.21 (d, 1H) ppm.

Example 35

2-Bromo-7-methyl-3b,4,5,6,6a,7-hexahydro-1-thia-
5-aza-cyclopenta[α]pentalene

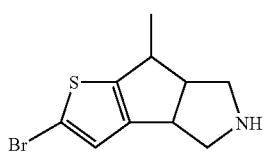

a.) 7-Methyl-3b,6,6a,7-tetrahydro-4H-1-thia-5-aza-cyclopenta[α]pentalene-5-carboxylic acid tert-butyl ester (Scheme 3)

NaHCO₃ (64 mg, 0.76 mmol) was added to a solution of 1:1 acetone:water (2 mL) at 0° C. followed by the addition of the product from Example 34, step h) (77 mg, 0.36 mmol) and di-tert-butyl dicarbonate (87 mg, 0.40 mmol). The stirred mixture was allowed to warm to room temperature over 3 hours. The reaction mixture was extracted with ethylacetate (2×8 mL), and the combined organic extracts were washed with brine (5 mL), dried (MgSO₄), and solvent evaporated in vacuo to give the crude product that was purified by column chromatography (SiO₂) using 0-50% ethylacetate-hexane gradient to afford the subtitle compound (87 mg, 86.1%). MS calculated for $C_{15}H_{21}NO_2S$+H: 280, observed: 280.

b.) 2-Bromo-7-methyl-3b,6,6a,7-tetrahydro-4-H-1-thia-5-aza-cyclopenta[α]-pentalene-5-carboxylic acid tert-butyl ester N-bromosuccinimide (59 mg, 0.33 mmol) was added to a solution of the product from step a) (87 mg, 0.31 mmol) in 2 mL of 1:1 acetic acid:chloroform at room temperature. The reaction mixture was stirred for 30 minutes after which it was quenched with saturated NaHCO₃ (2 mL). The reaction mixture was extracted with ethylacetate (3×5 mL) and the combined ethyl acetate extracts were dried with MgSO₄. The ethyl acetate was evaporated leaving yellow oil that was purified by column chromatography (SiO₂) using 5-50% ethyl acetate-hexane gradient. MS calculated for $C_{15}H_{20}BrNO_2S$+H: 358, observed: 258 and 260.

c.) 2-Bromo-7-methyl-3b,4,5,6,6a,7-hexahydro-1-thia-5-aza-cyclopenta[α]pentalene The product from step b) (50 mg, 0.14 mmol) was dissolved in 2 mL of 4M HCl/dioxane and stirred at room temperature for one hour. The solvent was evaporated leaving a solid that was purified by preparative LC/MS. MS calculated for $C_{10}H_{12}BrNS$+H: 258, observed: 258 and 260. ¹H NMR (CDCl₃ 300 MHz) δ 1.29 (d, 3H), 1.98 (s, 1H), 3.14 (m, 3H), 3.32 (m 2H), 3.50 (m, 1H), 3.70 (m, 1H), 6.74 (s, 1H) ppm.

Example 36

5-Bromo-7-methyl-1,2,3,3a,7,7a-hexahydro-4-thia-
2-aza-cyclopenta[α]pentalene

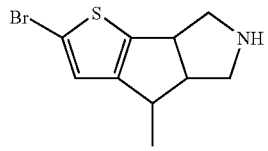

a.) 3-Thiophen-2-yl-acrylic acid ester (Scheme 3)

Thiophene-2-carbaldehyde (4.00 g, 35.7 mol) was treated by the method outlined in Example 34, step a) to afford the subtitle compound (4.5 g, yield: 75%). MS calculated for $C_9H_{10}O_2S$+H: 183, observed: 183.

b.) 1-(1-Phenyl-ethyl)-4-thiophen-2-yl-pyrrolidine-3-carboxylic acid ethyl ester The product from step a) (4.5 g, 0.027 mol) was treated by the method outlined in Example 34, step b) except the crude product was purified by silica-gel chromatography using a ethyl acetate/hexanes gradient (2% to 45% ethyl acetate) to give diastereomer 1 ($R_{f(Diastereomer\ 1)}$: 0.44, TLC-9:1/hexane:ethylacetate) and diastereomer 2 ($R_{f(Diastereomer\ 2)}$: 0.33, TLC-9:1/hexane:ethylacetate) of the subtitle compound (5.8 g, combined yield: 73%). MS calculated for $C_{19}H_{23}NO_2S$+H: 330, observed: 330. The two diastereomers were individually carried through the following synthetic steps to give enantiomers 1 and 2.

c.) 1-(1-Phenyl-ethyl)-4-thiophen-2-yl-pyrrolidine-3-carboxylic acid

The product from step b), diastereomer 1 (5.8 g, 0.019 mol) was treated by the method outlined in Example 34, step c) to afford the subtitle compound that was used in the next step without further purification. MS calculated for $C_{17}H_{19}NO_2S$+H: 302, observed: 302.

d.) 1-(1-Phenyl-ethyl)-4-thiophen-2-yl-pyrrolidine-3-carbonyl chloride

The product from step c) (6.7 g, 0.021 mol) was treated by the method outlined in Example 34, step d) to afford the subtitle compound that was used in the next step without further purification. MS calculated for $C_{17}H_{18}ClNOS$+H: 320, observed: as methyl ester in methanol: 316.

e.) 2-(1-Phenyl-ethyl)-2,3,3a,7a-tetrahydro-1H-4-thia-2-aza-cyclopenta[α]-pentalen-7-one The product from step d) (6.1 g, 0.018 mol) was treated by the method outlined in Example 34, step e) to afford the subtitle compound (1.9 g, yield: 40%). MS calculated for $C_{17}H_{17}NOS$+H: 284, observed: 284.

f.) 7-Methylene-2-(1-Phenyl-ethyl)-1,2,3,3a,7,7a-hexahydro-4-thia-2-aza-cyclopenta[α]pentalene The product from step e) (822 mg, 3.1 mmol) was treated by the method outlined in Example 34, step f) except the crude product was used in the next step without purification. MS calculated for $C_{18}H_{19}NS+H$: 282, observed: 282.

g.) 7-Methyl-2-(1-phenyl-ethyl) 1,2,3,3a,7,7a-hexahydro-4-thia-2-aza-cyclopenta[α]pentalene The product from step f) (905 mg, 3.4 mmol) was treated by the method outlined in Example 34, step g) except the crude product was purified by column chromatography ($SiO_2$) using 5-65% ethylacetate-hexane gradient to give the subtitle compound (410 mg, yield: 65%). MS calculated for $C_{18}H_{21}NS+H$: 284, observed: 284.

h.) 7-Methyl-1,2,3,3a,7,7a-hexahydro-4-thia-2-aza-cyclopenta[α]pentalene

The product from step g) (410 mg, 1.5 mmol) was treated by the method outlined in Example 34, step h) to afford the subtitle compound. MS calculated for $C_{10}H_{13}NS+H$: 180, observed: 180.

i.) 7-Methyl-3,3a7,7a-tetrahydro-1H-4-thia-2-aza-cyclopenta[α]pentalene-2-carboxylic acid tert-butyl ester The product from step h) (22 mg, 0.10 mmol) was treated by the method outlined in Example 35, step a) to afford the subtitle compound. MS calculated for $C_{15}H_{21}NO_2S+H$: 280, observed: 180.

j.) 5-Bromo-7-methyl-3,3a,7,7a-tetrahydro-1H-4-thia-2-aza-cyclopenta[α]-pentalene-2-carboxylic acid tert-butyl ester The product from step i) (39 mg, 0.14 mmol) was treated by the method outlined in Example 35, step b) to afford the subtitle compound. MS calculated for $C_{15}H_{20}BrNO_2S+H$: 358, observed: 258 and 260.

k.) 5-Bromo-7-methyl-1,2,3,3a,7,7a-hexahydro-4-thia-2-aza-cyclopenta-[α]pentalene The product from step j) (35 mg, 0.098 mmol) was treated by the method outlined in Example 35, step c) to afford the title compound. MS calculated for $C_{10}H_{12}BrNS+H$: 258, observed: 258 and 260. $^1$H NMR ($CDCl_3$ 300 MHz) δ 1.29 (d, 3H), 1.95 (s, 1H), 3.16 (m, 3H), 3.36 (m, 3H), 3.87 (m, 1H), 6.74 (s, 1H) ppm.

Example 37

6-Bromo-1,2,3,3a,7,7a-hexahydro-4-thia-2-aza-cyclopenta[α]pentalene

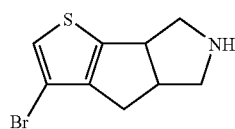

a.) 3-(4-Bromo-thiophen-2-yl)-acrylic acid methyl ester (Scheme 3)

4-Bromo-thiophene-2-carbaldehyde (44 g, 0.23 mol) and [Bis-(2,2,2-trifluoro-ethoxy)-phosphoryl]-acetic methyl ester (80.6 g, 0.253 mol) were treated by the method outlined in Example 34, step a) to afford the subtitle compound that was purified by column chromatography ($SiO_2$) using a 0-60% ethylacetate-hexane gradient (46.22 g, yield: 78%). MS calculated for $C_8H_7BrO_2S+H$: 247, observed: 247 249.

b.) 4-(4-Bromo-thiophen-2-yl)-1-(1-phenyl-ethyl)-pyrrolidine-3-carboxylic acid methyl ester The product of step a) (36 g, 0.146 mol) was treated by the method outlined in Example 34, step b) to afford the crude product that was purified by silica-gel chromatography using a ethyl acetate/hexanes gradient (0% to 30% ethyl acetate) to give diastereomer 1 ($R_{f(Diastereomer\ 1)}$: 0.44, TLC-8:2/hexane:ethylacetate) and diastereomer 2 ($R_{f(Diastereomer2)}$: 0.33, TLC-8:2/hexane:ethylacetate). MS calculated $C_{18}H_{20}BrNO_2S+H$: 395, observed: 395 and 397. The two diastereomers (15 g/diastereomer, total yield: 30 g, 52%) were individually carried through the following synthetic steps to give enantiomers 1 and 2 (synthesis of enantiomer 1 shown below).

c.) 4-(4-Bromo-thiophen-2-yl)-1-(1-phenyl-ethyl)-pyrrolidine-3-carboxylic acid.

The product of step b), diastereomer 1 (15 g, 0.038 mol) was treated by the method outlined in Example 34, step c) to afford the subtitle compound (14.7 g, yield: 100%). MS calculated for $C_{17}H_{18}BrNO_2S+H$: 380, observed 380 and 383.

d.) 4-(4-Bromo-thiophen-2-yl)-1-(1-phenyl-ethyl)-pyrrolidine-3-carbonyl chloride The product from step c) (14.7 g, 38.8 mmol) was treated by the method outlined in Example 34, step d) to afford the subtitle compound. MS calculated for $C_{17}H_{17}BrClNOS+H$: 398, observed: 398 and 400.

e.) 6-Bromo-2-(1-phenyl-ethyl)-2,3,3a,7a-tetrahydro-1H-4-thia-2-aza-cyclopenta[α]pentalen-7-one The product from step d) (11.1 g, 0.0280 mol) was treated by the method of Example 34, step e) except the reaction was run at room temperature to give the crude product that was purified by column chromatography ($SiO_2$) using 5-70% ethylacetate-hexane gradient to afford the subtitle compound (6.3 g, yield: 62%). MS calculated for $C_{17}H_{16}BrNOS+H$: 362, observed: 362 and 364.

f.) 6-Bromo-2-(1-phenyl-ethyl)-1,2,3,3a,7,7a-hexahydro-4-thia-2-aza-cyclopenta[α]pentalene t-Butylaminoborane (1080 mg, 12.42 mmol) was added to a suspension of $AlCl_3$ (828 mg, 6.21 mmol) in 30 mL of dichloromethane at 0° C. and the reaction mixture was allowed to come to room temperature and stirred for 30 minutes. The product from step e) (746 mg, 2.07 mmol) dissolved in 10 mL dichloromethane was added to the borane/$AlCl_3$ reaction mixture and stirred at room temperature for 12 hours. The reaction was quenched with 2 N NaOH to pH=12. The organic phase was separated washed with brine and dried with $MgSO_4$. The solvent was evaporated leaving a white solid. The crude was purified by column chromatography (SiO$_2$) using 5-50% ethylacetate-hexane gradient to afford the subtitle compound (536 mg, yield: 74.6%). MS calculated for C$_{17}$H$_{18}$BrNS+H: 348, observed: 348 and 350.

g.) 6-Bromo-1,2,3,3a,7,7a-hexahydro-4-thia-2-aza-cyclopenta[α]pentalene.

The product from step f) was treated by the method outlined in Example 34, step h) to give the crude product that was purified by preparative LC/MS to give the title compound. MS calculated for C$_9$H$_{10}$BrNS+H: 244, observed: 244 and 246. $^1$H NMR (CDCl$_3$ 300 MHz) δ 2.70 (m, 2H), 3.14 (m, 3H), 3.60 (m, 4H), 7.40 (s, 1H) ppm.

Example 38

5-Bromo-1,2,3,3a,7,7a-hexahydro-4-thia-2-aza-cyclopenta[α]pentalene

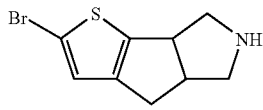

a.) 3-Thiophen-2-yl-acrylic acid methyl ester (Scheme 3)

Thiophene-2-carbaldehyde (4.00 g, 35.7 mmol) and [bis-(2,2,2-trifluoro-ethoxy)-phosphoryl]-acetic acid methyl ester (12.5 g, 39.3 mmol) were treated by the method outlined in Example 34, step a to afford the subtitle compound (4.5 g, yield: 75%). MS calculated for C$_8$H$_8$O$_2$S+H: 169, observed: 169.

b.) 1-Benzyl-4-thiophen-2-yl-pyrrolidine-3-carboxylic acid methyl ester

The product from step a) (4.5 g, 0.0268 mol) and benzyl-methoxymethyl-trimethylsilanylmethyl-amine (7.62 g, 0.032 mol) was treated by the method outlined in Example 34, step b) to afford the subtitle compound (5.8 g, yield: 73%). MS calculated for C$_{17}$H$_{19}$NO$_2$S+H: 302, observed: 302.

c.) 1-Benzyl-4-thiophen-2-yl-pyrrolidine-3-carboxylic acid

The product from step b) (5.8 g, 0.019 mol) was treated by the method outlined in Example 34, step c) to afford the subtitle compound (6.7 g, quantitative conversion). MS calculated for C$_{16}$H$_{17}$NO$_2$S+H: 288, observed: 288.

d.) 1-Benzyl-4-thiophen-2-yl-pyrrolidine-3-carbonyl chloride

The product from step c) (6.7 g, 0.021 mol) was treated by the method of Example 34, step d) to afford the subtitle compound (6.1 g, yield: 86%). MS calculated for C$_{16}$H$_{16}$ClNOS+H: 306, observed: 302 as methyl ester in methanol.

e.) 2-Benzyl-Z 3,3a,7,7a-tetrahydro-1H-4-thia-2-aza-cyclopenta[α]pentalen-7-one The product from step d) (6.1 g, 0.018 mol) was treated by the method outlined in Example 34, step e to afford the subtitle compound (1.9 g, yield: 40%). MS calculated for C$_{16}$H$_{15}$NOS+H: 270, observed: 270.

f.) 2-Benzyl-1,2,3,3a,7,7a-hexahydro-4-thia-2-aza-cyclopenta[α]pentalen-7-ol NaBH$_4$ (1664 mg, 44 mmol) was added in portions to a solution of the product of step e) (1183 mg, 4.40 mmol) in methanol at 0° C. The reaction mixture was allowed to come to room temperature and was stirred overnight. The solvent was evaporated and the residue was diluted with brine (50 ml) and extracted with ethyl acetate (2×50 mL). The combined organic extracts were dried with MgSO$_4$ and solvent evaporated in vacuo to afford the subtitle compound (1192 mg, quantitative conversion) that was used without further purification. MS calculated for C$_{16}$H$_{17}$NOS+H: 272, observed: 272.

g.) 2-Benzyl-1,2,3,3a,7,7a-hexahydro-4-thia-2-aza-cyclopenta[α]pentalene

Indiumtrichloride (973 mg, 4.40 mmol) and chlorodiphenylsilane (2888 mg, 13.20 mmol) were added to a solution of the product from step f) (1192 mg, 4.40 mmol) in 20 mL of dichloroethane. The reaction mixture was heated at 60° C. overnight and then was cooled to room temperature and quenched with saturated NaHCO$_3$ (50 ml). The reaction mixture was extracted with ethylacetate (2×50 mL). The combined organic extracts were washed with brine (50 ml), dried with MgSO$_4$ and solvent evaporated in vacuo to afford the subtitle compound (638 mg, yield: 57%) that was used without further purification. MS calculated C$_{16}$H$_{17}$NS+H: 256, observed: 256.

h.) 1,2,3,3a,7,7a-Hexahydro-4-thia-2-aza-cyclopenta[α]pentalene

The product from step g) (638 mg, 2.50 mmol) was treated by the method outlined in Example 34, step h) to afford the subtitle compound (493 mg, yield: 98%). MS calculated for C$_9$H$_{11}$NS+H: 166, observed: 166.

i) 3,3a,7,7a-Tetrahydro-1H-4-thia-2-aza-cyclopenta[α]pentalene-2-carboxylic acid ethyl ester Triethylamine (741 mg, 7.32 mmol) was added to a solution of the product from step h) (493 mg, 2.44 mmol) in 12 mL of CH$_2$Cl$_2$ at ° C. followed by the addition of ethyl chloroformate (529 mg, 4.88 mmol). The reaction was allowed to come to room temperature and was stirred for two hours. The reaction mixture was diluted with brine (15 mL) and extracted with dichloromethane (3×15 mL). The combined organic extracts were dried with MgSO$_4$ and the solvent was evaporated in vacuo give the crude product that was purified by column chromatography (SiO$_2$) using a 0-30% ethyl acetate-hexane gradient to give the subtitle compound. MS calculated for C$_{12}$H$_{15}$NO$_2$S+H: 238, observed: 238.

j.) 5-Bromo-3,3a,7,7a-tetrahydro-1H-4-thia-2-aza-cyclopenta[α]pentalene-2-carboxylic acid ethyl ester The product of step i) (148 mg, 0.62 mmol) was treated by the method outlined in Example 35, step b) to afford the subtitle compound. MS calculated for $C_{12}H_{14}BrNO_2S+H$: 316, observed 316 and 318.

k.) 5-Bromo-1,2,3,3a,7,7a-hexahydro-4-thia-2-aza-cyclopenta[α]pentalene

The product of step j) was treated by the method of Example 16, step b) to give the title compound. MS calculated for $C_9H_{10}BrNS+H$: 244, observed: 244 and 246.

Example 39

6-Bromo-5-trifluoromethyl-1,2,3,3a,7,7a-hexahydro-4-thia-2-aza-cyclopenta[α]pentalene

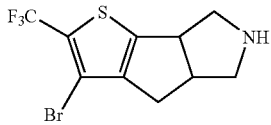

a.) 6-Bromo-3,3a,7,7a-tetrahydro-1-H-4-thia-2-aza-cylopenta[α]pentalene-2-carboxylic acid tert-butyl ester (Scheme 3)

The product of Example 37, step g) (600 mg, 2.16 mmol) was treated by the method of Example 35, step a) to afford the subtitle compound. MS calculated for $C_{14}H_{18}BrNO_2S+H$: 344, observed: 244 and 246.

b.) 6-Bromo-5-iodo-3,3a,7,7a-tetrahydro-1H-4-thia-2-aza-cyclopenta[α]-35 pentalene-2-carboxylic acid tert-butyl ester N-iodosuccinimide (156 mg, 0.69 mmol) was added to a solution of the product from step a) (227 mg, 0.66 mmol) in 3 mL of a 1:1 mixture of $CHCl_3$/acetic acid at room temperature and the reaction mixture was stirred for 30 minutes. The reaction was quenched with saturated $NaHCO_3$ (3 mL) and extracted with dichloromethane (3×5 mL). The combined organic extracts were washed with saturated $NaHCO_3$ (3 ml), 5% $NaSO_3$ (3 mL), dried ($MgSO_4$), and solvent evaporated to give the crude product that was purified by column chromatography ($SiO_2$) using a 5-50% ethylacetate-hexane gradient to afford the subtitle compound (178 mg, 58%). MS calculated for $C_{14}H_{17}BrINO_2S+H$: 470, observed: 470 and 472.

c.) 6-Bromo-5-trifluoromethyl-3,3a,7,7a-tetrahydro-1H-4-thia-2-aza-cyclopenta[α]pentalene-2-carboxylic acid tert-butyl ester Dipyridyl (31 mg, 0.20 mmol), CuI (34 mg, 0.18 mmol) and KF (10 mg, 0.18 mmol) were added to a solution of the product from step b) (78 mg, 0.17 mmol) in 1.6 mL of 1:1 DMF/1-methyl-2-pyrollidinone. The reaction mixture was stirred for 1 hour at 80° C. and then cooled to room temperature. Next, trifluoromethyl trimethylsilane (118 mg, 0.83 mmol) was added and the reaction mixture was heated to 800C for 12 hours. The reaction was cooled to room temperature and filtered through a silica plug eluting with $CH_2Cl_2$(10 ml). The organic mixture was washed with brine (2×3 mL), dried with $MgSO_4$, and was concentrated to a dark oil that was purified by preparative LC/MS to give the subtitle compound. MS calculated for $C_{15}H_{17}BrF_3NO_2S+H$: 412, observed: 413.

d.) 6-Bromo-5-trifluoromethyl-1,2,3,3a,7,7a-hexahydro-4-thia-2-aza-cyclopenta[α]penatlene The product from step c) (30 mg, 0.073 mmol) was treated by the method of Example 35, step c) to afford the title compound. MS calculated for $C_{10}H_9BrF_3NS+H$: 312, observed: 312 and 314.

Example 40

6-Methyl-5-trifluoromethyl-1,2,3,3a,7,7a-hexahydro-4-thia-2-aza-cyclopenta[α]pentalene

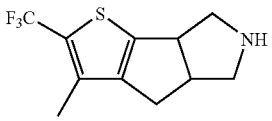

a.) 6-Methyl-3,3a,7,7a-tetrahydro-1H-4-thia-2-aza-cyclopenta[α]pentalene-2-carboxylic acid tert-butyl ester (Scheme 3)

[1,1'-Bis(diphenylphosphino)-ferrocene]dichloropalladium(II) complex in $CH_2Cl_2$ (35 mg, 0.043 mmol) was added to a solution of the product from Example 39, step a) (245 mg, 0.72 mmol) in 2 mL of dioxane, followed by the addition of 2.0 M dimethylzinc in toluene (0.72 mL, 1.43 mmol). The reaction mixture was stirred for 3 hours at 110° C. under a $N_2$ atmosphere. Next, the reaction mixture was cooled to room temperature and quenched with saturated ammonium chloride. The reaction mixture was diluted with brine (3 mL) and was extracted with ethyl acetate (2×8 mL). The combined organic extracts were dried with $MgSO_4$ and the solvent was evaporated to give the crude product that was used without further purification. MS calculated for $C_{15}H_{21}NO_2S+H$: 280, observed: 280.

b.) 5-Iodo-6-methyl-3,3a,7,7a-tetrahydro-1H-4-thia-2-aza-cyclopenta[α]-pentalene-2-carboxylic acid tert-butyl ester The product from step a) (62 mg, 0.22 mmol) was treated by the method outlined in Example 39, step b to afford the subtitle compound (35 mg, yield: 39% over two-steps). MS calculated for $C_{15}H_{20}INO_2S+H$: 405, observed: 408.

c.) 6-Methyl-5-trifluoromethyl-3,3a,7,7a-tetrahydro-1H-4-thia-2-aza-cyclopenta[α]pentalene-2-carboxylic acid tert-butyl ester The product from step b) (35 mg, 0.086 mmol) was treated by the method outlined in Example 39, step c to afford the subtitle compound. MS calculated for $C_{16}H_{20}F_3NO_2S+H$: 348, observed: 348.

d.) 6-Methyl-5-trifluoromethyl-1,2,3,3a,7,7a-hexahydro-4-thia-2-aza-cyclopenta[α]pentalene The product from step c) (25 mg, 0.072 mmol) was treated by the method outlined in Example 35, step c) to afford the title compound. MS calculated for $C_{11}H_{12}F_3NS+H$: 248, observed: 248.

Example 41

6-Methoxy-5-trifluoromethyl-1,2,3,3a,7,7a,-hexahydro-4-thia-2-aza-cyclopenta[α]pentalene

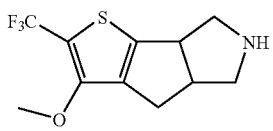

a.) 6-Bromo-3,3a,7,7a-tetrahydro-1H-4-thia-2-aza-cyclopenta[α]pentalene-2-carboxylic acid ethyl ester (Scheme 3)

The product from Example 37, step g) (300 mg, 1.08 mmol) was treated by the method outlined in Example 38, step i) to afford the subtitle compound. (255 mg, yield: 75%). MS calculated for $C_{12}H_{14}BrNO_2S+H$: 316, observed: 316 and 318.

b.) 6-Methoxy-1,2,3,3a,7,7a-hexahydro-4-thia-2-aza-cyclopenta[α]pentalene

A pressure tube was charged with the product from step a) (255 mg, 0.81 mmol) dissolved in 4 mL of dry methanol. To this solution CuO (64 mg, 0.81 mmol), NaOCH₃ (320 mg, 4.86 mmol) and KI (5 mg) were added. The reaction chamber was sealed airtight and the reaction mixture was stirred and heated at 150° C. for 72 hours. The reaction was cooled to room temperature and filtered through Celite, diluted with 10 mL of water and extracted with dichloromethane (2×15 mL). The combined organic extracts were dried with MgSO₄, filtered and the solvent was evaporated to give the crude subtitle compound as a dark oil that was used without further purification. MS calculated for $C_{10}H_{13}NOS+H$: 196, observed: 196.

c.) 6-Methoxy-3,3a,7,7a-tetrahydro-1H-4-thia-2-aza-cyclopenta[α]pentalene-2-carboxylic acid tert-butyl ester The product from step b) (151 mg, 0.77 mmol) was treated by the method outlined in Example 35, step a) to afford the subtitle compound. MS calculated $C_{15}H_{21}NO_3S+H$: 296, observed: 196 (M-BOC+2H).

d.) 5-Iodo-6-methoxy-3,3a,7,7a-tetrahydro-1H-4-thia-2-aza-cyclopenta[α]-pentalene-2-carboxylic acid tert-butyl ester The product from step c) (32 mg, 0.11 mmol) was treated by the method outlined in Example 39, step b) to afford the subtitle compound. MS calculated for $C_{15}H_{20}INO_3S+H$: 422, observed: 322 (M-BOC+2H).

e.) 6-Methoxy-5-trifluoromethyl-3,3a,7,7a-tetrahydro-1H-4-thia-2-aza-cyclopenta[α]pentalene-2-carboxylic acid tert-butyl ester The product from step d) (23 mg, 0.055 mmol) was treated by the method outlined in Example 39, step c) to afford the subtitle compound. MS calculated for $C_{16}H_{20}F_3NO_3S+H$: 364, observed: 264 (M-BOC+2H).

f.) 6-Methoxy-5-trifluoromethyl-1,2,3,3a,7,7a-hexahydro-4-thia-2-aza-cyclopenta[α]pentalene The product from step e) (3 mg, 0.008 mmol) was treated by the method outlined in Example 35, step c) to afford the title compound. MS calculated for $C_{11}H_{12}F_3NOS+H$: 264, observed: 264.

Example 42

5-Chloro-6-methoxy-1,2,3,3a,7,7a-hexahydro-4-thia-2-aza-cyclopenta[α]pentalene

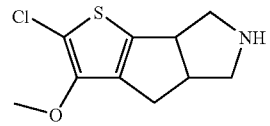

a.) 5-Chloro-6-methoxy-3,3a,7,7a-tetrahydro-1H-4-thia-2-aza-cyclopenta[α]-pentalene-2-carboxylic acid tert-butyl ester (Scheme 3)

Sulfurylchloride (5.5 mg, 0.041 mmol) was added to a solution of the product from example 41, step c) (10 mg, 0.034 mmol) in 1 mL of CHCl₃ at room temperature. The reaction mixture was stirred for 30 minutes, quenched with 1 mL of brine, and extracted with dichloromethane (2×2 mL). The combined organic extracts were dried (MgSO₄) and solvent evaporated in vacuo to give the subtitle compound that was used without further purification. MS calculated for $C_{15}H_{20}ClNO_3S+H$: 330, observed: 230 (M-BOC+2H).

b.) 5-Chloro-6-methoxy-1,2,3,3a,7,7a-hexahydro-4-thia-2-aza-cyclopenta[α]-pentalene The product from step a) (10 mg, 0.030 mmol) was treated by the method outlined in Example 35, step c) to afford the subtitle compound. MS calculated for $C_{10}H_{12}ClNOS+H$: 230, observed: 230.

Example 43

1-(6-Bromo-1,2,3,3a,7,7a-hexahydro-4-thia-2-aza-cyclopenta[α]-pentalen-5-yl)-2,2-dimethyl-propan-1-one

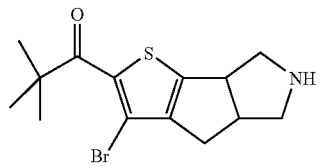

a.) 5,6-Dibromo-3,3a,7,7a-tetrahydro-1H-4-thia-2-aza-cyclopenta[α]pentalene-2-carboxylic acid tert-butyl ester (Scheme 3)

The product from Example 39, step a) (127 mg, 0.37 mmol) was treated by the method outlined in Example 35, step b) to afford the subtitle compound. MS calculated for $C_{14}H_{17}Br_2NO_2S+H$: 423, observed: 323 (M-BOC+2H).

b.) 6-Bromo-5-(2,2-dimethyl-propionyl)-3,3a,7,7a-tetrahydro-1H-4-thia-2-aza-cyclopenta[α]pentalene-2-carboxylic acid tert-butyl ester 1.6 M nBuLi (0.069 mL, 0.11 mmol) was added to a solution of the product from step a) (43 mg, 0.10 mmol) in 2 mL of THF at −78OC under $N_2$ atmosphere. The reaction mixture was stirred for 20 minutes after which trimethylacetyl chloride (36 mg, 0.3 mmol) was added and the reaction mixture stirred for an additional 5 minutes at −78° C. The reaction mixture was allowed to warm to room temperature and was stirred for 15 minutes. The reaction mixture was diluted with 2 mL of brine and was extracted with dichloromethane (2×3 mL). The combined organic extracts were dried with $MgSO_4$ and concentrated in vacuo to give the crude subtitle compound that was used without further purification. MS calculated for $C_{19}H_{26}BrNO_3S+H$: 428, observed: 328 and 330 (M-BOC+2H).

c.) 1-(6-Bromo-1,2,3,3a,7,7a-hexahydro-4-thia-2-aza-cyclopenta[α]pentalene-5-yl)-Z2-dimethyl-propan-1-one The product from step b) (20 mg, 0.05 mmol) was treated by the method outlined in Example 35, step c to afford the title compound. MS calculated for $C_{14}H_{18}BrNOS+H$: 328, observed: 328 and 330. $^1H$ NMR ($CDCl_3$ 300 MHz) □1.35 (s, 9H), 1.99 (s, 1H), 2.60 (m, 1H), 2.90 (m, 1H), 3.05 (m, 2H), 3.24 (m, 2H), 3.47 (m, 2H) ppm.

Example 44

Benzo[b]-7-Methyl-1,2,3,3a,7,7a-hexahydro-4-thia-2-aza-cyclopenta-[α]pentalene

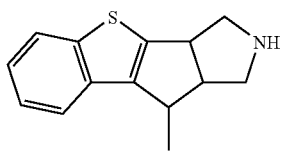

a.) 3-Benzo[b]thiophen-2-yl-acrylic acid tert-butyl ester (Scheme 3)

Potassium bis(trimethylsilyl)amide (5.4 g, 0.027 mol) was added to a solution of 18-Crown-6 (13.7 g, 0.052 mol) and (diphenoxy-phosphoryl)-acetic acid tert-butyl ester (9.4 g, 0.027 mol) in dry THF (120 mL) at −78OC. After 30 minutes of stirring at this temperature, benzo[b]thiophene-2-carbaldehyde (4.0 g, 0.024 mol) was added and the reaction was stirred for 3 hours at −78OC after which the reaction was quenched with saturated ammonium chloride (200 mL). The reaction mix was allowed to come to room temperature and was extracted with ethyl acetate (3×200 mL) and the combined organic extracts were washed with 10% HCl (200 mL), brine (200 mL), and dried over $MgSO_4$. The solvent was evaporated in vacuo leaving the crude product that was purified by column chromatography ($SiO_2$) using a 5-40% ethylacetate-hexane gradient to afford the subtitle compound (4.64 g, yield: 74%). MS calculated for $C_{15}H_{16}O_2S+H$: 261, observed: 261.

b.) 4-Benzo[b]thiophen-2-yl-1-(1-phenyl-ethyl)-pyrrolidine-3-carboxylic acid tert-butyl ester The product from step a) (4.64 g, 0.018 mol) was treated by the method outlined in Example 34, step b) except the crude subtitle compound (mixture of diastereomers) was used in the next step without further purification. MS calculated for $C_{25}H_{29}NO_2S+H$: 408, observed: 408.

c.) 4-Benzo[b]thiophen-2-yl-1-(1-phenyl-ethyl)-pyrrolidine-3-carboxylic acid The product from step b) (2.0 g, 0.0077 mol) was dissolved in 20 mL dichloromethane and was treated with 10 mL of TFA and stirred for 2 hours at room temperature. The solvent was evaporated in vacuo to give the crude subtitle compound that was used in the next step without further purification. MS calculated for $C_{21}H_{21}NO_2S+H$: 352, observed: 352.

d.) 4-Benzo[b]thiophen-2-yl-1-(1-phenyl-ethyl)-pyrrolidine-3-carbonyl chloride The product from step c) (1.6 g, 0.0047 mol) was treated by the method outlined in Example 34, step d) the subtitle compound that was used without further purification. MS calculated for $C_{21}H_{20}ClNOS+H$: 370, observed: 370.

e.) 4-Benzo[b]-2-(1-Phenyl-ethyl)-23,3a,7,7a-tetrahydro-1H-4-thia-2-aza-cyclopenta[α]pentalen-7-one The product from step d) (1.7 g, 0.0047 mol) was treated by the method outlined in Example 34, step e) to afford the subtitle compound. MS calculated for $C_{21}H_{21}NOS+H$: 334, observed: 334.

f.) 4-Benzo[b]-7-methylene-2-(1-phenyl-ethyl)-1,2,3,3a,7,7a-hexahydro-4-thia-2-aza-cyclopenta[α]pentalene The product from step e) (475 mg, 1.43 mmol) was treated by the method outlined in Example 34, step f) to afford the subtitle compound. MS calculated for $C_{22}H_{21}NS+H$: 332, observed: 332.

g.) 4-Benzo[b]-7-methyl-2-(1-phenyl-ethyl)-1,2,3,3a,7,7a-hexahydro-4-thia-2-aza-cyclopenta[α]pentalene The product from step f) (474 mg, 1.43 mmol) was treated by the method outlined in Example 34, step g) to afford the subtitle compound. MS calculated for $C_{22}H_{23}NS+H$: 334, observed: 334.

h.) 4-Benzo[b]-7-methyl-1,2,3,3a,7,7a-hexahydro-4-thia-2-aza-cyclopenta[α]pentalene The product of step g) (217 mg, 0.65 mmol) was treated by the method outlined in Example 34, step h) to afford the title compound. MS calculated for $C_{14}H_{15}NS+H$: 230, observed: 230 i.) 4-Benzo[b]-7-methyl-3,3a,7,7a-tetrahydro-1H-4-thia-2-aza-cyclopenta-[α]pentalene-2-carboxylic acid ethyl ester The product from step h) (112 mg, 0.42 mmol) was treated by the method outlined in Example 38, step i) to afford the subtitle compound. MS calculated for $C_{17}H_{19}NO_2S+H$: 302, observed: 302 and 304.

j.) 4-Benzo[b]-7-methyl-1,2,3,3a,7,7a-hexahydro-4-thia-2-aza-cyclopenta-[α]pentalene The product from step i) (30 mg, 0.10 mmol) was treated by the method outlined in Example 38, step k) to afford the title compound. MS calculated for $C_{14}H_{15}NS+H$: 230, observed 230. $^1$HNMR (CDCl$_3$ 300 MHz) δ 1.54 (d, 3H), 3.37 (m, 2H), 3.45 (d, 1H), 3.58 (m, 1H). 4.11 (m, 1H), 3.69 (m, 2H), 7.38 (m, 2H), 7.82 (m, 2H) ppm.

Example 45

4-Benzo[b]-1,2,3,3a,7,7a-Hexahydro-4-thia-2-aza-cyclopenta[α]-pentalene

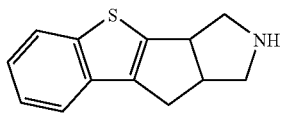

a.) 4-Benzo[b]-2-(1-Phenyl-ethyl)-1,2,3,3a,7,7a-hexahydro-4-thia-2-aza-cyclopenta[α]pentalen-7-ol (Scheme 3)

The product from Example 44, step e) (345 mg, 1.04 mmol) was treated by the method outlined in Example 38, step f) to afford the subtitle compound (269 mg, 77%) that was used without further purification. MS calculated for $C_{21}H_{21}NOS+H$: 336, observed: 336.

b). 4-Benzo[b]-2-(1-phenyl-ethyl)-1,2,3,3a,7,7a-hexahydro-4-thia-2-aza-cyclopenta[α]pentalene The product from step a) (269 mg, 0.80 mmol) was treated by the method outlined in Example 38, step g) to afford the subtitle compound that was used in the next step without further purification. MS calculated for $C_{21}H_{21}NS+H$: 320, observed: 320.

c.) 4-Benzo[b]-1,2,3,3a,7,7a-Hexahydro-4-thia-2-aza-cyclopenta[α]-pentalene

The product from step, b) (357 mg, 0.80 mmol) was treated by the method outlined in Example 34, step h) except the crude product was purified by preparative LC/MS to afford the subtitle compound. MS calculated for $C_{13}H_{13}NS+H$: 216, observed: 216.

d.) 4-Benzo[b]-3,3a,7,7a-tetrahydro-1H-4-thia-2-aza-cyclopenta[α]pentalene-2-carboxylic acid ethyl ester The product from step c) (40 mg, 0.19 mmol) was treated by the method outlined in Example 38, step i) to afford the subtitle compound. MS calculated for $C_{16}H_{17}NO_2S+H$: 288, observed: 288.

e.) 4-Benzo[b]-1,2,3,3a,7,7a-Hexahydro-4-thia-2-aza-cyclopenta[α]-pentalene

The product from step d) (10 mg, 0.035 mmol) was treated by the method outlined in Example 38, step k) to afford the subtitle compound. MS calculated for $C_{13}H_{13}NS+H$: 216, observed: 216.

Example 46

7-Bromo-8-methyl-2,3,3A,4,5,8b-hexahydro-1H-6-thia-2-aza-as-indacene

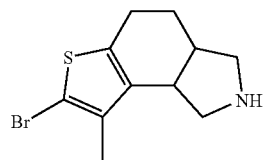

a.) 2-Benzyl-octahydro-isoindol-4-one (Scheme 8)

Benzyl-methoxymethyl-trimethylsilanylmethyl-amine (29.6 g, 0.12 mol) was added to a solution of cyclohex-2-enone (10 g, 0.104 mol) in 500 mL of dichloromethane at 0° C. followed by the dropwise addition of 10 mol % TFA dissolved in 2 mL of dichloromethane. The reaction mixture was stirred at room temperature overnight and was quenched with 50 mL of saturated NaHCO$_3$. The organic layer was washed with 500 mL of brine, dried with MgSO$_4$ and solvent was evaporated in vacuo to give the crude product that was purified by column chromatography (SiO$_2$) using a 2-45% ethylacetate-hexane gradient to afford the subtitle compound. (13.8 g, 60%). MS calculated for $C_{15}H_{19}NO+H$: 230, observed: 230.

b.) Octahydro-isoindol-4-one

The product of step a) (13.8 g, 0.060 mol) was treated by the method of Example 34, step h) to give the subtitle compound as its HCl salt. MS calculated for $C_8H_{13}NO+H$: 140, observed: 140.

c.) 4-Oxo-octahydro-isoindol-2-carboxylic acid tert-butyl ester

The product from step b) (8.3 g, 0.060 mol) was treated by the method outlined in Example 35, step a) to afford the subtitle compound (11.7 g, yield: 98%). MS calculated for $C_{13}H_{21}NO_3+H$: 240, observed: 240.

d.) 7-Amino-1,3,3a,4,5,8b-hexahydro-6-thia-2-aza-as-indacene-2,8-dicarboxylic acid 2-tert-butyl ester 8-ethyl ester Ethylcyanoacetate (6.67 g, 0.059 mmol) and sulfur (1.89 g, 0.059 mol) were added to the product of step c) (11.7 g, 0.059 mol) dissolved in 100 mL of DMF. Piperidine (5.02 g, 0.059 mol) was added and the reaction mixture was stirred at 600C for 3.5 hours. The reaction mixture was cooled to room temperature, diluted with 40 mL of brine and was extracted with ethyl acetate (3×100 mL). The combined ethyl acetate extracts were dried with MgSO$_4$ and the solvent was evaporated in vacuo to give the subtitle compound that was used without further purification. MS calculated for $C_{18}H_{26}N_2O_4S$+H: 367, observed: 367.

e.) 1,3,3,3a,4,5,8b-Hexahydro-6-thia-2-aza-as-indacene-2,8-dicarboxylic acid 2-tert-butyl ester 8-ethyl ester Tert-butylnitrite (7.09 g, 0.069 mol) was added to the product of step d) (16.8 g, 0.046 mol) dissolved in 200 mL of ethanol followed by the addition of copper diacetate (12.5 g, 0.069 mol). The reaction mixture was heated for one hour at 60° C., cooled to room temperature, diluted with 200 mL of water and extracted with ethyl acetate (3×200 mL). The combined organic extracts were dried (MgSO$_4$) and solvent evaporated in vacuo to give the crude product that was purified by column chromatography (SiO$_2$) using a 5-50% ethylacetate-hexane gradient to afford the subtitle compound (5.8 g, yield: 36%). MS calculated for $C_{18}H_{25}NO_4S$+H: 352, observed: 352.

f.) 8-Hydroxymethyl-1,3,3a, 4,5,8b-hexahydro-6-thia-2-aza-as-indacene-2-carboxylic acid tert-butyl ester Lithium chloride (2.77 g, 0.066 mol) was added to the product of step e) (5.8 g, 0.016 mol) in 200 mL of THF followed by the addition of 2.0 M lithium borohydride (58 mL, 0.115 mol). The reaction was stirred overnight at 60° C. and was then cooled to room temperature. The reaction mixture was filtered through Celite, diluted with 100 mL of water and was extracted with ethyl acetate (3×150 mL). The combined ethyl acetate extracts were dried (MgSO$_4$) and the solvent evaporated in vacuo to give the subtitle compound that was used without further purification. MS calculated for $C_{16}H_{23}NO_3S$+H: 310, observed: 310.

g.) 8-Methyl-2,3,3a,4,5,8b-hexahydro-1H-6-thia-2-aza-as-indacene

The product from step f) was treated by the method outlined in Example 37, step f) to give the subtitle compound that was used in the next step without further purification. MS calculated for $C_{11}H_{15}NS$+H: 194, observed: 194.

h.) 8-Methyl-1,3,3a,4,5,8b-hexahydro-6-thia-2-aza-as-indacene-2-carboxylic acid ethyl ester The product from step g) (1.7 g, 0.0055 mol) was treated by the method outlined in Example 38, step i) except the crude product was purified by column chromatography (SiO$_2$) using a 5-50% ethyalacetate-hexane gradient to give the subtitle compound. MS calculated for $C_{14}H_{19}NO_2S$+H: 266, observed: 266.

i.) 7-Bromo-8-methyl-1,3,3a,4,5,8b-hexahydro-6-thia-2-aza-as-indacene-2-carboxylic acid ethyl ester The product from step h) (40 mg, 0.15 mmol) was treated by the method outlined in Example 35, step j) except the crude product was purified by preparative TLC (SiO$_2$) (20:80% ethylacetate-hexane) to give the subtitle compound (42 mg, 81 mmol). MS calculated for $C_{14}H_{18}BrNO_2S$+H: 344, observed: 344 and 346.

j.) 7-Bromo-8-methyl-2,3,3a,4,5,8b-hexahydro-1H-6-thia-2-aza-as-indacene

The product from step i) was treated by the method outlined in Example 38, step k) to afford the title compound. MS calculated for $C_{11}H_{14}BrNS$+H: 272, observed: 272 and 274.

Example 47

3-Bromo-5,5a,6,7,8,8a-hexahydro-4H-1-thia-7-aza-as-indacene

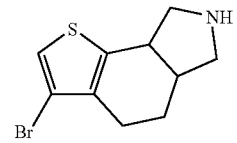

a.) 1-Benzyl-4-(4-bromo-thiophen-2-yl)-pyrrolidine-3-carboxylic acid methyl ester (Scheme 9)

The product from Example 37, step a) (40.4 g, 0.164 mol) and benzyl-methoxymethyl-trimethylsilanylmethyl-amine (41.2 g, 0.164 mol) were treated by the method outlined in Example 34, step b except the crude product was purified by column chromatography (SiO$_2$) using 5-50% ethylacetate-hexane gradient to give the subtitle compound (43 g, yield: 68%). MS calculated for $C_{17}H_{18}BrNO_2S$+H: 380, observed: 380 and 382.

b.) [1-Benzyl-4-(4-bromo-thiophen-2-yl)-pyrrolidin-3-yl]-methanol

The product of step a) (16.7 g, 0.042 mol) dissolved in 150 mL of THF was added dropwise to 1M lithium aluminum-hydride (42 mL, 0.042 mol) dissolved in 150 mL of THF at 0° C. The reaction was stirred at 0° C. for 5 minutes and for two hours at room temperature. The reaction mixture was cooled to 0° C. and quenched with 3 mL of water, 5 mL of 2 N NaOH and 50 mL of water. The organic layer was separated and was filtered through Celite and the solvent was evaporated in vacuo. The crude product was purified by column chromatography (SiO$_2$) using 10-70% ethyl acetate-dichloromethane gradient to give the subtitle compound (9.1 g, yield: 61%). MS calculated for $C_{16}H_{18}BrNOS$+H: 352, observed: 352 and 354.

c.) Toluene-4-sulfonic acid 1-benzyl-4-(4-bromo-thiophen-2-yl)-pyrrolidine-3-yl-methyl ester Diisopropylethylamine (20.2 g, 0.156 mol), dimethyl aminopyridine (320 mg, 2.6 mmol) and TsCl were (9.88 g, 0.052 mol) were added, respectively, to the product of step b) (9.1 g, 0.026 mol) in 150 mL of dichloromethane at 0° C. The reaction mixture was stirred overnight at room temperature and then was quenched with 75 mL of 1 M HCl and extracted with dichloromethane (3×100 mL). The combined organic extracts were washed with brine (100 mL), dried with MgSO$_4$ and evaporated in vacuo to give the crude product that was purified by column chromatography (SiO$_2$) using a 0-50% methanol-dichloromethane gradient to give the subtitle compound (6.7 g, yield: 51%). MS calculated for $C_{23}H_{24}BrNO_3S_2$+H: 506, observed: 506 and 508.

d.) [1-Benzyl-4-(4-bromo-thiophen-2-yl)-pyrrolidin-3-yl]-acetonitrile

18-Crown-6 (5.3 g, 0.020 mol) and potassium cyanide (1.3 g, 0.020 mol) were added, respectively, to a solution of the product from step c) (6.7 g, 0.013 mol) in 50 mL of DMSO. The reaction mixture was heated at 80° C. overnight, cooled to room temperature, diluted with water (150 mL) and extracted with ethylacetate (3×150 mL). The combined organic extracts were washed with brine (200 mL), dried with $MgSO_4$, and evaporated in vacuo to give the crude product that was purified by column chromatography ($SiO_2$) using 1-100% ethylacetate-hexane gradient to give the subtitle compound (2.1 g, yield: 44%). MS calculated for $C_{17}H_{17}BrN_2S+H$: 361, observed: 361 and 363.

e.) [1-Benzyl-4-(4-bromo-thiophen-2-yl)-pyrrolidin-3-yl]-acetic acid

The product from step d) (2.1 g, 5.8 mmol) was treated by the method outlined in Example 34, step c) to afford the subtitle compound that was used in the next step without further purification. MS calculated for $C_{17}H_{18}BrNO_2S+H$: 380, observed: 380 and 382.

f.) [1-Benzyl-4-(4-bromo-thiophen-2-yl)-pyrrolidin-3-yl]-acetyl chloride

The product from step e) (2.7 g, 0.0071 mol) was treated by the method outlined in Example 34, step d) to afford the subtitle compound that was used in the next step without further purification. MS calculated for $C_{17}H_{17}BrClNOS+H$: 398, observed: 398 and 400.

g.) 7-Benzyl-3-bromo-5,5a, 6,7,8,8a-hexahydro-1-thia-7-aza-as-indacene-4-one The product from step f) (3.6 g, 9.1 mmol) was treated by the method outlined in Example 34, step e) except the crude product was purified by column chromatography ($SiO_2$) using 8-70% ethylacetate-hexane gradient to give the subtitle compound (2.2 g, yield: 67%). MS calculated for $C_{17}H_{16}BrNOS+H$: 362, observed: 362 and 364.

h.) 7-Benzyl-3-bromo-5,5a,6,7,8,8a-hexahydro-4H-1-thia-7-aza-as-indacene

The product from step g) (392 mg, 1.1 mmol) was treated by the method outlined in Example 37, step f) to afford the subtitle compound (360 mg, yield: 95%). MS calculated for $C_{17}H_{18}BrNS+H$: 348, observed: 348 and 350.

i.) 3-Bromo-5,5a, 6,7,8,8a-hexahydro-4H-1-thia-7-aza-as-indacene

The product from step h) (360 mg, 1.0 mmol) was treated by the method outlined in Example 34, step h) to afford the subtitle compound. MS calculated for $C_{10}H_{12}BrNS+H$: 258, observed: 258 and 260. $^1H$ NMR ($CDCl_3$ 300 MHz) δ 1.76 (m, 2H), 1.94 (m, 1H), 2.13 (m, 1H), 2.54 (m, 2H), 2.94 (m, 2H), 3.45 (m, 3H), 7.05 (s, 1H) ppm.

Example 48

2-Bromo-3-methyl-5,5a,6,7,8,8a-hexahydro-4H-1-thia-7-aza-as-indacene

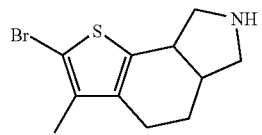

a.) 7-Benzyl-3-methyl-5,5a, 6,7,8,8a-hexahydro-1-thia-7-aza-as-indacen-4-one (Scheme 9)

The product from Example 47, step g) (1399 mg, 3.88 mmol) was treated by the method outlined in Example 40, step a) except the crude product was purified by column chromatography ($SiO_2$) using 5-100% ethylacetate-hexane gradient to give the subtitle compound (612 mg, yield: 53%). MS calculated for $C_{18}H_{19}NOS+H$: 298, observed: 298.

b.) 7-Benzyl-3-methyl-5,5a,6,7,8,8a-hexahydro-4H-1-thia-7-aza-as-indacene

The product from step a) (612 mg, 2.1 mmol) was treated by the method outlined in Example 37, step f) except the crude product was purified by column chromatography ($SiO_2$) using 5-70% ethylacetate-hexane gradient to give the subtitle compound (385 mg, 66%). MS calculated for $C_{18}H_{21}NS+H$: 284, observed: 284.

c.) 7-Benzyl-2-bromo-3-methyl-5,5a, 6,7,8,8a-hexahydro-4H-1-thia-7-aza-as-indacene The product from step b) (385 mg, 1.36 mmol) was treated by the method outlined in Example 35, step j) to afford the subtitle compound (338 mg, yield: 69%). MS calculated for $C_{18}H_{20}BrNS+H$: 362, observed: 362 and 364.

d.) 2-Bromo-3-methyl-5,5a,6,7,8,8a-hexahydro-4H-1-thia-7-aza-as-indacene

The product from step c) (338 mg, 0.94 mmol) was treated by the method outlined in Example 34, step h) to afford the title compound. MS calculated for $C_{11}H_{14}BrNS+H$: 272, observed 272 and 274.

Example 49

Compounds that were separated into their respective diastereomers that were used to derive enantiomers.

| Compound | TLC Solvent System (silica-gel chromatography conditions) | $R_f$ | Diastereomer | Enantiomerically pure Final Product(s) Derived from Diastereomers* |
|---|---|---|---|---|
| Example 34, Step b) | 9:1 Hexane-Ethyl acetate (2-45% EtOAc/Hexanes-gradient) | 0.40 0.33 | 1 2 | 34, 35 34, 35 |

-continued

| Compound | Rf | Diastereomer | TLC Solvent System (silica-gel chromatography conditions) | Enantiomerically pure Final Product(s) Derived from Diastereomers* |
|---|---|---|---|---|
| Example 36 Step b) | 0.44 0.33 | 1 2 | 9:1 Hexane-Ethyl acetate (2-45% EtOAc/ Hexanes-gradient) | 36 36 |
| Example 37 Step b) | 0.44 0.33 | 1 2 | 8:2 Hexane-Ethyl acetate (0-30% EtOAc/ Hexanes-gradient) | 37 37, 39, 40, 41, 42, 43 |

*Diastereomer 1 results in enantiomer 1 and diastereomer 2 results in enantiomer 2.

Example 50

Separation of enantiomers for select compounds of the invention.

The following compounds were separated into their respective enantiomers using a 5 micron, 20 mm×250 mm Chiral Pak AD-RH chiral column running a mobile phase of 100% methanol at 10 mL/minute flow rate.

| Compound | Enantiomer | Retention Time (minutes) | Final Product Derived from Enantiomer |
|---|---|---|---|
| Example 16, Step a) | 1 2 | 10.3 16.5 | 16 16 |
| Example 17, Step e) | 1 2 | 9.8 11.6 | 17 17 |
| Example 18, Step b) | 1 2 | 10.0 12.2 | 18 18 |
| Example 26, Step k) | 1 2 | 9.1 10.0 | 26 26 |
| Example 27, Step l) | 1 2 | 9.9 10.7 | 27 27 |
| Example 28, Step j) | 1 2 | 8.8 9.4 | 28 28 |
| Example 29, Step j) | 1 2 | 8.3 11.2 | 29 29 |
| Example 30, Step l) | 1 2 | 8.4 10.0 | 30 30 |
| Example 32, Step b) | 1 2 | 11.1 12.9 | 32 32 |
| Example 33, Step d) | 1 2 | 11.9 13.6 | 33 33 |
| Example 38, Step j) | 1 2 | 10.4 16.5 | 38 38 |

| Compound | Enantiomer | Retention Time (minutes) | Final Product Derived from Enantiomer |
|---|---|---|---|
| Example 44, Step i) | 1 2 | 10.4 14.5 | 44 44 |
| Example 45, Step d) | 1 2 | 12.9 35.6 | 45 45 |
| Example 46, Step i) | 1 2 | 10.5 11.6 | 46 46 |
| Example 47, Step i) | 1 2 | 5.9 9.8 | 47 47 |
| Example 48, Step d) | 1 2 | 6.1 9.1 | 48 48 |

The following procedure was utilized to evaluate representative compounds of the present invention as $5HT_{2c}$ receptor agonists. The results of this assay are set forth in Table 1.

Cell Culture

HEK 293 EBNA expressing the human 5HT2c receptor (VNV Isoform) (Burns et al., NATURE 387:30308, 1997 Fitzgerald et al., NEUROPSYCHO-PHARMACOLOGY 21:825-905, 1999) were grown in DMEM containing 10% dialysed FBS, 9 μg/ml blasticidin at 37° C. in 5% $CO_2$ atmosphere.

Calcium Mobilization

HEK 293 EBNA cells expressing human $5HT2_c$ receptor ($2\times10^4$/well) were seeded in black 384-well collagen coated plates and incubated overnight at 37° C. in a 5% CO2/95% atmosphere. After removing medium, cells were treated with HBSS buffer (137 mM NaCl, 5.4 mM KCl, 5.5 mM Glucose, 20 mM Hepes, pH 7.5, 2.1 mM $MgCl_2$, 0.3 mM $CaC_2$, 0.02 mM $MgSO_4$, 3.0 mM $NaHCO_3$, and 0.64 mM $KH_2PO_4$) containing the Calcium3 dye (Molecular Device, CA), 2.5 mM probenecid and 0.08% pluronic acid for 60 minutes according to manufacture's instruction. Compounds were diluted in CsCl Ringers buffer (58.3 mM CsCl, 5.4 mM KCl, 5.5 mM Glucose, 20 mM Hepes, pH 7.5, 2.1 mM $MgCl_2$, 1.2 mM $CaCl_2$). 5HT was utilized as a positive control. Ligand-induced calcium release and consequent fluorescence was measured on a Fluorometric Imaging Plate Reader (FLIPR, Molecular Device, CA).

Data Analysis

All data were analyzed by nonlinear least square curve fitting using Prism 4.0 software. Agonist stimulation of calcium-induced fluorescence in FLIPR was fitted to sigmoidal dose response using equation Y=Bottom+(Top-Bottom)/(1+ 10^((LogEC50-X))), where X is the logarithm of concentration of compounds and Y is the fluorescent response.

| Example Number | Molecule | 5-HT2c EC50 (hVSV, μM) |
|---|---|---|
| 1 | 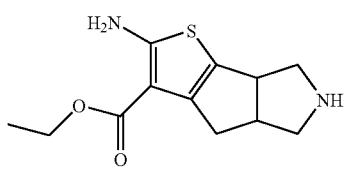 | <0.1 |

-continued

| Example Number | Molecule | 5-HT2c EC50 (hVSV, μM) |
|---|---|---|
| 2 | ethyl 2-bromo-thieno-cyclopenta-pyrrole carboxylate | <0.1 |
| 3 | ethyl thieno-cyclopenta-pyrrole carboxylate | <0.1 |
| 4 | ethyl 2-chloro-thieno-cyclopenta-pyrrole carboxylate | <0.1 |
| 5 | 2-amino-3-(3-trifluoromethylbenzoyl)-thieno-cyclopenta-pyrrole | <10 |
| 6 | 2-amino-3-(4-methylbenzoyl)-thieno-cyclopenta-pyrrole | <1 |
| 7 | 2-amino-3-(4-chlorobenzoyl)-thieno-cyclopenta-pyrrole | <10 |
| 8 | methyl thieno-cyclopenta-pyrrole-2-carboxylate | <10 |
| 9 | thieno-cyclopenta-pyrrole | >10 |
| 10 | 2-chloro-3-cyano-thieno-cyclopenta-pyrrole | <10 |

-continued

| Example Number | Molecule | 5-HT2c EC50 (hVSV, μM) |
|---|---|---|
| 11 | | <10 |
| 12 | | <0.1 |
| 13 | | <0.1 |
| 14 | | <1 |
| 15 | | <0.1 |
| 16<br>16, Enantiomer 1<br>16, Enantiomer 2 | | <0.1<br><0.1<br><0.1 |
| 17<br>17, Enantiomer 1<br>17, Enantiomer 2 | | <0.1 |
| 18<br>18, Enantiomer 1<br>18, Enantiomer 2 | | <0.1<br><0.1<br><0.1 |
| 19 | | <1 |
| 20 | | <1 |
| 21 | | <0.1 |

-continued

| Example Number | Molecule | 5-HT2c EC50 (hVSV, μM) |
|---|---|---|
| 22 | (structure: dibromo thieno-cyclopenta-pyrrolidine) | <0.1 |
| 23 | (structure: CF3 thieno-cyclopenta-pyrrolidine) | <1 |
| 24 | (structure: Cl, methyl thieno-cyclopenta-pyrrolidine) | <1 |
| 25 | (structure: I, methyl thieno-cyclopenta-pyrrolidine) | <1 |
| 26<br>26, Enantiomer 1<br>26, Enantiomer 2 | (structure: Cl, dimethyl thieno-cyclopenta-pyrrolidine) | <1<br><1<br><0.1 |
| 27, Enantiomer 1<br>27, Enantiomer 2 | (structure: methyl, Br, methyl thieno-cyclopenta-pyrrolidine) | <1<br><0.1 |
| 28<br>28, Enantiomer 1<br>28, Enantiomer 2 | (structure: Br thieno-cyclopenta-piperidine) | <1<br><10<br><1 |
| 29<br>29, Enantiomer 1<br>29, Enantiomer 2 | (structure: Br thieno-cyclopenta-piperidine isomer) | <1<br><1<br><10 |
| 30<br>30, Enantiomer 1<br>30, Enantiomer 2 | (structure: Br thieno-cyclopenta-piperidine) | <1<br><1<br>>10 |
| 31 | (structure: Br thieno-cyclopenta-piperidine) | <1 |

-continued
| Example Number | Molecule | 5-HT2c EC50 (hVSV, μM) |
|---|---|---|
| 32, Enantiomer 1 | 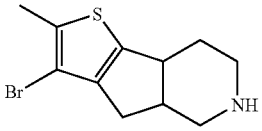 | <10 |
| 32, Enantiomer 2 | | <10 |
| 33, Enantiomer 1 | 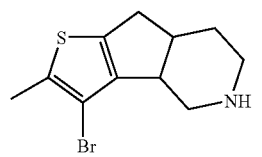 | <1 <10 |
| 33, Enantiomer 2 | | |
| 34 | 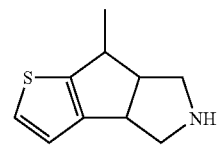 | >10 |
| 34, Enantiomer 1 | | <10 |
| 34, Enantiomer 2 | | >10 |
| 35 | 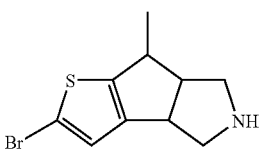 | <1 |
| 35, Enantiomer 1 | | <1 |
| 35, Enantiomer 2 | | <1 |
| 36, Enantiomer 1 | 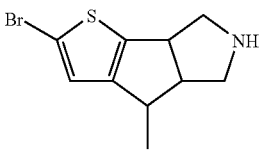 | <1 |
| 36, Enantiomer 2 | | <10 |
| 37 | 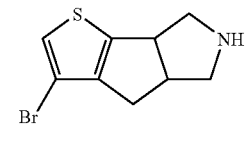 | <0.1 |
| 37, Enantiomer 1 | | <1 |
| 37, Enantiomer 2 | | <0.1 |
| 38 | 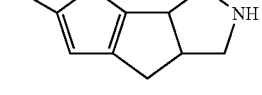 | <1 |
| 38, Enantiomer 1 | | <0.1 |
| 38, Enantiomer 2 | | <1 |
| 39, Enantiomer 2 | 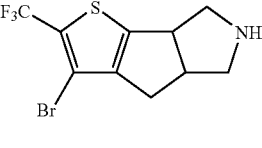 | <0.1 |
| 40, Enantiomer 2 | 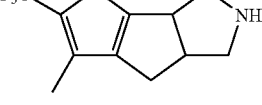 | <0.1 |
| 41, Enantiomer 2 | 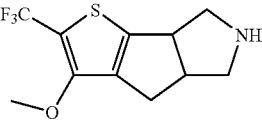 | <0.1 |

-continued

| Example Number | Molecule | 5-HT2c EC50 (hVSV, μM) |
|---|---|---|
| 42, Enantiomer 2 | | <10 |
| 43, Enantiomer 2 | | <1 |
| 44 | | <1 |
| 44, Enantiomer 1 | | <1 |
| 44, Enantiomer 2 | | <1 |
| 45 | | <0.1 |
| 45, Enantiomer 1 | | <0.1 |
| 45, Enantiomer 2 | | <1 |
| 46 | | <10 |
| 46, Enantiomer 1 | | <10 |
| 46, Enantiomer 2 | | <1 |
| 47 | | <1 |
| 47, Enantiomer 1 | | <1 |
| 47, Enantiomer 2 | | <1 |
| 48 | | <1 |
| 48, Enantiomer 1 | | <1 |
| 48, Enantiomer 2 | | <1 |

The invention claimed is:

1. A compound of the formula

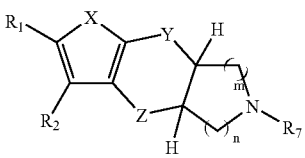

where
X is S or O;
m is 1 or 2;
n is 1 or 2;
m+n is ≧2;
Y is $CR_3R_{3a}$ and Z is a covalent bond or $CR_4R_{4a}$,
Y is a covalent bond and Z is $CH_2CH_2$ or $CR_4R_{4a}$ or
Y or $CH_2CH_2$ and Z is a covalent bond;

$R_1$ and $R_2$ are independently selected from the group consisting of H, halogen, $C_{1-10}$alkyl, $C_{2-10}$alkenyl, $C_{2-10}$alkynyl, perhaloalkyl, CN, $OR_5$, $SR_5$, $N(R_5)_2$, $COOR_5$, $COR_6$, $CON(R_5)_2$, $NR_5COR_6$, $NR_5CO_2R_6$, $NR_5SO_2R_6$, aryl, heteroaryl, $C_{1-10}$alkylaryl, and $C_{1-10}$alkylheteroaryl, wherein said aryl or heteroaryl can be optionally substituted;

$R_1$ and $R_2$ taken together can form a 5- or 6-member aryl or heteroaryl ring that is optionally substituted;

$R_3$ is selected from the group consisting of H, halogen, $C_{1-10}$alkyl, $C_{2-10}$alkenyl, $C_{2-10}$alkynyl, perhaloalkyl, CN, $OR_5$, $SR_5$, $N(R_5)_2$, $OCOR_6$, $COOR_5$, $COR_6$, $CON(R_5)_2$, $NR_5COR_6$, $NR_5CO_2R_6$, $NR_5SO_2R_6$, aryl, heteroaryl, $C_{1-10}$alkylaryl, and $C_{1-10}$alkylheteroaryl, wherein said aryl or heteroaryl can be optionally substituted;

$R_{3a}$ is H or $R_3$ and $R_{3a}$ taken together are —$CH_2CH_2$— or carbonyl;

$R_4$ is selected from the group consisting of H, halogen, $C_{1-10}$alkyl, $C_{2-10}$alkenyl, $C_{2-10}$alkynyl, perhalo alkyl, CN, $OR_5$, $SR_5$, $N(R_5)_2$, $OCOR_6$, $COOR_5$, CON, CON $(R_5)_2$, $NR_5COR_6$, $NR_5CO_2R_6$, $NR_5SO_2R_6$, aryl, heteroaryl, $C_{1-10}$alkylaryl, and $C_{1-10}$alkylheteroaryl, wherein said aryl or heteroaryl can be optionally substituted;

$R_{4a}$ is H or $R_4$ and $R_{4a}$ taken together are —$CH_2CH_2$— or carbonyl;

$R_5$ is selected from the group consisting of H, $C_{1-10}$alkyl, $C_{2-10}$alkenyl, $C_{2-10}$alkynyl, perhaloalkyl, $C_{1-10}$alkyl-O—$C_{1-10}$alkyl, aryl, heteroaryl, $C_{1-10}$alkyl-O-aryl, $C_{1-10}$alkyl-O-heteroaryl, $C_{1-10}$alkylaryl, and $C_{1-10}$alkylheteroaryl, wherein said aryl or heteroaryl can be optionally substituted;

$R_6$ is selected from the group consisting of $C_{1-10}$alkyl, $C_{2-10}$alkenyl, $C_{2-10}$alkynyl, perhaloalkyl, $C_{1-10}$alkyl-O—$C_{1-10}$alkyl, aryl, heteroaryl, $C_{1-10}$alkyl-O-aryl, $C_{1-10}$alkyl-O-heteroaryl, $C_{1-10}$alkylaryl, and $C_{1-10}$alkylhetroaryl, wherein said aryl or heteroaryl can be optionally substituted, and $R_7$ is selected from the group consisting of H, $C_{1-10}$alkyl, $C_{2-10}$alkenyl, $C_{2-10}$alkynyl, $C_{1-10}$alkyl-O—$C_{1-10}$alkyl, $COOR_5$, $COR_6$, $CON(R_5)_2$, aryl, heteroaryl, $C_{1-10}$alkyl-O-aryl, $C_{1-10}$alkyl-O-heteroaryl, $C_{1-10}$alkylaryl, and $C_{1-10}$alkylheteroaryl, wherein said aryl or heteroaryl can be optionally substituted, and the pharmaceutically acceptable salts thereof.

2. A compound as in claim 1 wherein X is S; Y is a bond or $CR_3R_{3a}$; Z is $CR_4R_{4a}$ or a bond; $R_1$, and $R_2$ are halogen, $C_{1-10}$alkyl, O—$C_{1-10}$alkyl or $CF_3$; $R_3$ is $C_{1-10}$alkyl; $R_{3a}$ is H; $R_4$ is $C_{1-10}$alkyl; $R_{4a}$ is H and $R_7$ is H.

3. A compound as in claim 1 selected from the group consisting of 5-Chloro-1,2,3,3a,7,7a-hexahydro-4-thia-2-aza-cyclopenta[α]pentalene-6-carbonitrile, 5-Bromo-1,2,3,3a,7,7a-hexahydro-4-thia-2-aza-cyclopenta[α]pentalene-6-carbonitrile, 6-Chloro-5-methyl-1,2,3,3a,7,7a-hexahydro-4-thia-2-aza-cyclopenta[α]pentalene, 6-Bromo-5-methyl-3,3a,7,7a-tetrahydro-1H-4-thia-2-aza-cyclopenta[α]pentalene, 5-Chloro-6-methyl-1,2,3,3a,7,7a-hexahydro-4-thia-2-aza-cyclopenta[α]pentalene, 5-Bromo-6-methyl-1,2,3,3a,7,7a-hexahydro-4-thia-2-aza-cyclopenta[α]pentalene, 2-Bromo-3b,4,5,6,6a,7-hexahydro-1-thia-5-aza-cyclopenta[α]pentalene, 5-Chloro-6,7-dimethyl-1,2,3,3a,7,7a-hexahydro-4-thia-2-aza-cyclopenta[α]pentalene, 6-Bromo-1,2,3,3a,7,7a-hexahydro-4-thia-2-aza-cyclopenta[α]pentalene, 5-Bromo-1,2,3,3a,7,7a-hexahydro-4-thia-2-aza-cyclopenta[α]pentalene, 6-Bromo-5-trifluoromethyl-1,2,3,3a,7,7a-hexahydro-4-thia-2-aza-cyclopenta[α]pentalene, 6-Methyl-5-trifluoromethyl-1,2,3,3a,7,7a-hexahydro-4-thia-2-aza-cyclopenta[α]pentalene, 6-Methoxy-5-trifluoromethyl-1,2,3,3a,7,7a,-hexahydro-4-thia-2-aza-cyclopenta[α]pentalene and 4-Benzo[b]-1,2,3,3a,7,7a-Hexahydro-4-thia-2-aza-cyclopenta[α]-pentalene.

4. A pharmaceutical composition comprising at least one compound of claim 1 and a pharmaceutically acceptable carrier.

* * * * *

UNITED STATES PATENT AND TRADEMARK OFFICE
CERTIFICATE OF CORRECTION

PATENT NO. : 7,423,056 B2
APPLICATION NO. : 11/217991
DATED : September 9, 2008
INVENTOR(S) : Bennani et al.

It is certified that error appears in the above-identified patent and that said Letters Patent is hereby corrected as shown below:

Column 93, line 3, delete the first instance of "CON" and insert --$COR_6$--.

Signed and Sealed this

Thirty-first Day of August, 2010

David J. Kappos
*Director of the United States Patent and Trademark Office*